United States Patent
Karra et al.

(10) Patent No.: US 9,546,166 B2
(45) Date of Patent: Jan. 17, 2017

(54) INDOLIZINE DERIVATIVES AND THEIR USE IN NEURODEGENERATIVE DISEASES

(71) Applicant: Merck Patent GmbH, Darmstadt (DE)

(72) Inventors: Srinivasa R. Karra, Pembroke, MA (US); Andreas Goutopoulos, Boston, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/814,659

(22) Filed: Jul. 31, 2015

(65) Prior Publication Data

US 2016/0031879 A1    Feb. 4, 2016

Related U.S. Application Data

(60) Provisional application No. 62/031,237, filed on Jul. 31, 2014.

(51) Int. Cl.
 *A61K 31/44*   (2006.01)
 *C07D 471/04*   (2006.01)

(52) U.S. Cl.
 CPC .................. *C07D 471/04* (2013.01)

(58) Field of Classification Search
 USPC .......................................... 514/299; 546/112
 See application file for complete search history.

(56) References Cited

FOREIGN PATENT DOCUMENTS

| WO | 0209706 A1 | 2/2002 |
|---|---|---|
| WO | 2007/095223 A2 | 8/2007 |
| WO | 2012080727 A2 | 6/2012 |

OTHER PUBLICATIONS

Ito N, Tamano S, Shirai T. A medium-term rat liver bioassay for rapid in vivo detection of carcinogenic potential of chemicals. Cancer Sci. Jan. 2003;94(1):3-8.*
Berge, Pharmaceutical Salts, Journal of Pharmaceutical Sciences, 1977, 66(1): 1-19.
Deuchars et al., Neuronal P2X7 Receptors are Targeted to Presynaptic Terminals in the Central and Peripheral Nervous Systems, J. Neuroscience, 2001, 21(18): 7143-7152.
Foster, Deuterium Isotope Effects in the Metabolism of Drugs and Xenobiotics: Implications for Drug Design, Advances in Drug Research, 1985, 14: 1-40.
Gillette et al., Theory for the Observed Isotope Effects on the Formation of Multiple Products by Different Kinetic Mechanisms of Cytochrome P450 Enzymes, Biochemistry,1994, 33(10): 2927-2937.
Griffiths et al., ATP Induces the Release of IL-1 from LPS-Primed Cells in Vivo, J. of Immun., 1995, 154: 2821-2828.
Hanzlik et al., Active Site Dynamics of Toluene Hydroxylation by Cytochrome P-450, J. Org. Chem., 1990, 55: 3992-3997.
Jarman et al., The deuterium isotope effect for the alpha-hydroxylation of tamoxifen by rat liver microsomes accounts for the reduced genotoxicity of D5-ethyl]taxoxifen, Carcinogenesis, 1995, 16(4): 683-688.
Kanjhan et al., Distribution of the P2X2 Receptor Subunit of the ATP-Gated Ion Channels in the Rat Central Nervous System, J. Comp. Neurol., 1999, 407:11-32.
Le et al., Sensory Presynaptic and Widespread Somatodendritic Immunolocalization of Central Ionotropic P2x ATP Receptors, Neuroscience, 1998, 83(1): 177-190.
Reider et al., Synthesis of (R)-Serine-2-d and Its Conversion to the Broad Spectrum Antibiotic Fludalanine, J. Org. Chem., 1987, 52: 3326-3334.
March's Advanced Organic Chemistry, 5th Ed., Ed.: Smith, M.B. and March, J., John Wiley & Sons, New York: 2001.
Organic Chemistry, Thomas Sorrell, University Science Books, Sausalito, 1999.
Solles et al., Altered Cytokine Production in Mice Lacking P2X7 Receptors, J. of Biol. Chem., 2001, 276(1): 125-132.
American Psychiatric Association: Diagnostic and Statistical Manual of Mental Disorders (DSM-IV-TR), Fourth Edition, Text Revision. Washington, D.C., American Psychiatric Association, pp. 345-428, 2000.
XP002744037; Database Registry (Online) Chemical Abstracts Service, (Jul. 11, 2000).

* cited by examiner

*Primary Examiner* — Rei-Tsang Shiao
(74) *Attorney, Agent, or Firm* — Dwight D. Kim; EMD Serono Research and Development Institute

(57) ABSTRACT

The present invention relates to indolizine compounds, and pharmaceutically acceptable compositions thereof, useful as antagonists of P2X7, and for the treatment of P2X7-related disorders.

16 Claims, No Drawings

US 9,546,166 B2

INDOLIZINE DERIVATIVES AND THEIR USE IN NEURODEGENERATIVE DISEASES

RELATED APPLICATION

This application claims the benefit of U.S. Provisional application 62/031,237, filed on Jul. 31, 2014, the content of which is incorporated by reference in its entirety.

TECHNICAL FIELD OF THE INVENTION

The present invention relates to indolizine compounds useful as antagonists of P2X7. The invention also provides pharmaceutically acceptable compositions comprising compounds of the present invention and methods of using said compositions in the treatment of various disorders.

BACKGROUND OF THE INVENTION

The P2X7 receptor is a ligand-gated ion channel that belongs to the Purinergic Receptor Family. The receptor is expressed on many cell types related to the immune and nervous systems. In the nervous system P2X7 is expressed on microglia, oligodendrocytes and astrocytes. Brief activation of the P2X7 receptor channel with its endogenous ligand ATP leads to several downstream events including the processing and release of the proinflammatory cytokine IL1-β from monocytes and macrophages. P2X7 activation also plays an important role in regulating the glutamate release/uptake in astrocytes.

P2X7 receptors are ionotropic receptors activated by ATP, which may regulate neurotransmission in the CNS by activating presynaptic and/or postsynaptic P2X7 receptors on central and peripheral neurons and glia (Deuchars S. A. et al., J. Neurosci. 21:7143-7152, (2001), Kanjhan R. et al., J. Comp. Neurol. 407:11-32 (1997), Le K. T. et al., Neuroscience 83:177-190 (1998)). Activation of the P2X7 receptor on cells of the immune system (macrophages, mast cells and lymphocytes) leads to release of interleukin-1β (IL-1β), giant cell formation, degranulation, and L-selectin shedding. ATP is able to increase local release and process of IL-1 in rats through a P2X7receptor mediated mechanism following lipopolysaccharide (LPS) intraperitoneal injections (Griffiths et al., J. Immunology Vol. 154, pages 2821-2828 (1995); Solle et al., J. Biol. Chemistry, Vol. 276, pages 125-132, (2001)).

Antagonism of the P2X7 receptor is considered to be an attractive therapeutic approach for the treatment of multiple sclerosis and Alzheimer's disease, due to its significant role in dampening the CNS inflammation and supporting neuroprotection.

SUMMARY OF THE INVENTION

It has now been found that compounds of this invention, and pharmaceutically acceptable compositions thereof, are effective as antagonists of P2X7. Such compounds have general formula I:

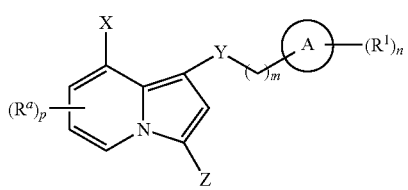

or a pharmaceutically acceptable salt thereof, wherein each of Ring A, X, Y, Z, $R^1$, $R^a$, m, n, and p, is as defined and described in embodiments herein.

Compounds of the present invention, and pharmaceutically acceptable compositions thereof, are useful for treating a variety of diseases, disorders or conditions, associated with P2X7 activity. Such diseases, disorders, or conditions include those described herein.

DETAILED DESCRIPTION OF CERTAIN EMBODIMENTS

1. General Description of Compounds of the Invention

In certain embodiments, the present invention provides antagonists of P2X7. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl) alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group. The term "alkynylene" refers to a bivalent alkynyl group. A substituted alkynylene chain is a group containing at least one triple bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydropyranyl, tetrahydrothiophenyl pyrrolidinyl, piperidinyl, pyrrolinyl, morpholinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

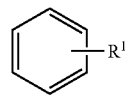

refers to at least

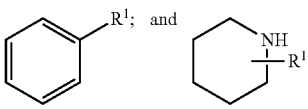

refers to at least

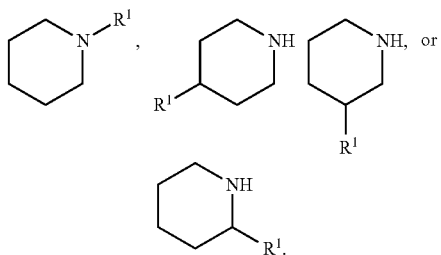

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which are optionally substituted with R°; —$(CH_2)_{0-1}O(CH_2)_{0-1}Ph$ which is optionally substituted with R°; —CH=CHPh, which is optionally substituted with R°; —$(CH_2)_{0-4}O(CH_2)_{0-1}$-pyridyl which is optionally substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, SC(S)SR°; —$(CH_2)_{0-4}SC(O)R°$; —$(CH_2)_{0-4}C(O)NR°_2$; —C(S)NR°_2; —C(S)SR°; —SC(S)SR°, —$(CH_2)_{0-4}OC(O)NR°_2$; —C(O)N(OR°)R°; —C(O)C(O)R°; —C(O)CH_2C(O)R°; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —S(O)_2NR°_2; —$(CH_2)_{0-4}S(O)R°$; —$N(R°)S(O)_2NR°_2$; —$N(R°)S(O)_2R$; —N(OR°)R°; —C(NH)NR°_2; —P(O)_2R°; —P(O)R°_2; —OP(O)R°_2; —OP(O)(OR°)_2; SiR°_3; —$(C_{1-4}$ straight or branched alkylene)O—N(R°)_2; or —$(C_{1-4}$ straight or branched alkylene)C(O)O—N(R°)_2, wherein each R° is optionally substituted as defined below and is independently hydrogen, $C_{1-6}$ aliphatic, —$CH_2Ph$, —$O(CH_2)_{0-1}Ph$, —$NH(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —$(CH_2)_{0-2}R^•$, -(haloR^•), —$(CH_2)_{0-2}OH$, —$(CH_2)_{0-2}OR^•$, —$(CH_2)_{0-2}CH(OR^•)_2$; —O(haloR^•), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —C(O)SR^•, —$(C_{1-4}$ straight or branched alkylene)C(O)OR^•, or —SSR^• wherein each R^• is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*_2, =NNHC(O)R*, =NNHC(O)OR*, =NNHS(O)_2R*, =NR*, =NOR*, —O(C(R*_2))_{2-3}O—, or —S(C(R*_2))_{2-3}S—, wherein each independent occurrence of R* is selected from hydrogen, $C_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*_2)_{2-3}O—, wherein each independent occurrence of R* is selected from hydrogen, $C_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R^•, -(haloR^•), —OH, —OR^•, —O(haloR^•), —CN, —C(O)OH, —C(O)OR^•, —$NH_2$, —NHR^•, —NR^•_2, or —$NO_2$, wherein each R^• is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R^†, —NR^†_2, —C(O)R^†, —C(O)OR^†, —C(O)C(O)R^†, —C(O)CH_2C(O)R^†, —S(O)_2R^†, —S(O)_2NR^†_2, —C(S)NR^†_2, —C(NH)NR^†_2, or —N(R^†)S(O)_2R^†; wherein each R^† is independently hydrogen, $C_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R^†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R^† are independently halogen, —R^•, -(haloR^•), —OH, —OR*, —O(haloR^•), —CN, —C(O)OH, —C(O)OR^•, —$NH_2$, —NHR^•, —NR^†_2, or —$NO_2$, wherein each R^• is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—$NO_2$, —CN, $CF_3$, $N_3$,

—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O— cycloalkyl, —O-aryl, —O-heteroaryl, —O-heterocyclic, —C(O)-alkyl, —C(O)-alkenyl, —C(O)-alkynyl, —C(O)-carbocyclyl, —C(O)-aryl, —C(O)— heteroaryl, —C(O)-heterocyclyl, —$CONH_2$, —CONH-alkyl, —CONH-alkenyl, —CONH-alkynyl, —CONH-carbocyclyl, —CONH-aryl, —CONH-heteroaryl, —CONH-heterocyclyl, —$OCO_2$-alkyl, —$OCO_2$-alkenyl, —$OCO_2$-alkynyl, —$OCO_2$-carbocyclyl, —$OCO_2$-aryl, —$OCO_2$-heteroaryl, —$OCO_2$-heterocyclyl, —$OCONH_2$, —OCONH-alkyl, —OCONH-alkenyl, —OCONH-alkynyl, —OCONH-carbocyclyl, —OCONH-aryl, —OCONH-heteroaryl, —OCONH-heterocyclyl, —NHC(O)-alkyl, —NHC(O)-alkenyl, —NHC(O)-alkynyl, —NHC(O)-carbocyclyl, —NHC(O)-aryl, —NHC(O)-heteroaryl, —NHC(O)-heterocyclyl, —$NHCO_2$-alkyl, —$NHCO_2$-alkenyl, —$NHCO_2$-alkynyl, —$NHCO_2$-carbocyclyl, —$NHCO_2$-aryl, —$NHCO_2$-heteroaryl, —$NHCO_2$-heterocyclyl, —$NHC(O)NH_2$, —NHC(O)NH-alkyl, —NHC(O)NH-alkenyl, —NHC(O)NH-alkenyl, —NHC(O)NH-carbocyclyl, —NHC(O)NH-aryl, —NHC(O)NH-heteroaryl, —NHC(O)NH—heterocyclyl, $NHC(S)NH_2$, —NHC(S)NH-alkyl, —NHC(S)NH-alkenyl, —NHC(S)NH-alkynyl, —NHC(S)NH-carbocyclyl, —NHC(S)NH-aryl, —NHC(S)NH-heteroaryl, —NHC(S)NH-heterocyclyl, —$NHC(NH)NH_2$, —NHC(NH)NH-alkyl, —NHC(NH)NH-alkenyl, —NHC(NH)NH-alkenyl, —NHC(NH)NH-carbocyclyl, —NHC(NH)NH-aryl, —NHC(NH)NH-heteroaryl, —NHC(NH)NH-heterocyclyl, —NHC(NH)-alkyl, —NHC(NH)-alkenyl, —NHC(NH)-alkenyl, —NHC(NH)-carbocyclyl, —NHC(NH)-aryl, —NHC(NH)-heteroaryl, —NHC(NH)-heterocyclyl, —C(NH)NH-alkyl, —C(NH)NH-alkenyl, —C(NH)NH-alkynyl, —C(NH)NH-carbocyclyl, —C(NH)NH-aryl, —C(NH)NH-heteroaryl, —C(NH)NH-heterocyclyl, —S(O)-alkyl, —S(O)-alkenyl, —S(O)-alkynyl, —S(O)-carbocyclyl, —S(O)-aryl, —S(O)-heteroaryl, —S(O)-heterocyclyl —$SO_2NH_2$, —$SO_2NH$-alkyl, —$SO_2NH$-alkenyl, —$SO_2NH$-alkynyl, —$SO_2NH$-carbocyclyl, —$SO_2NH$-aryl, —$SO_2NH$-heteroaryl, —$SO_2NH$-heterocyclyl, —$NHSO_2$-alkyl, —$NHSO_2$-alkenyl, —$NHSO_2$-alkynyl, —$NHSO_2$-carbocyclyl, —$NHSO_2$-aryl, —$NHSO_2$-heteroaryl, —$NHSO_2$-heterocyclyl,

—$CH_2NH_2$, —$CH_2SO_2CH_3$,

-mono-, di-, or tri-alkyl silyl,

-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, tautomers, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms.

For example, compounds having the present structures including the replacement of hydrogen by deuterium or tritium, or the replacement of a carbon by a $^{13}C$- or $^{14}C$- enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3H$ or $^{14}C$, has been incorporated, is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant. Compounds of the invention may be substituted by $^{18}F$, for use as PET imaging agents.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concen-tra-tion at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 μM. In certain embodiments, a modulator has an $IC_{50}$ and/or binding constant of less than about 5 μM. In certain embodiments, a modulator has an $IC_{50}$ and/or binding constant of between about 1 to about 5 μM. In certain embodiments, a modulator has an $IC_{50}$ and/or binding constant of less than about 1 μM. In certain embodiments, a modulator has an $IC_{50}$ and/or binding constant of between about 500 to about 1000 nM. In certain embodiments, a modulator has an $IC_{50}$ and/or binding constant of less than about 500 nM. In certain embodiments, a modulator has an $IC_{50}$ and/or binding constant of between about 100 to about 500 nM. In certain embodiments, a modulator has an $IC_{50}$ and/or binding constant of less than about 100 nM. In certain embodiments, a modulator has an $IC_{50}$ and/or binding constant of between about 10 to about 100 nM. In certain embodiments, a modulator has an $IC_{50}$ and/or binding constant of less than about 10 nM.

The terms "measurable affinity" and "measurably inhibit," as used herein, means a measurable change in P2X7 activity between a sample comprising a compound of the present invention, or composition thereof, and P2X7, and an equivalent sample comprising P2X7, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

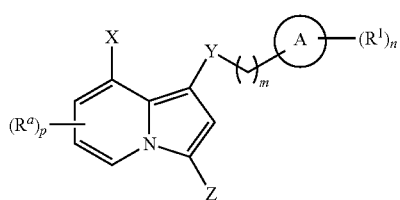

I or a pharmaceutically acceptable salt thereof, wherein:

X is -halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$; or X is a C$_{1-6}$ aliphatic, C$_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

Y is O, S, SO$_2$, SO, C(O), CO$_2$, C(O)N(R), NRC(O), NRC(O)N(R), NRSO$_2$, or N(R);

Ring A is C$_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; or a 6-18 membered bicyclic, fused bicyclic, spiro bicyclic, or polycyclic ring having 0-4 heteroatoms independently selected from nitrogen, oxygen, or sulfur, each of which is optionally substituted;

each R$^1$ is independently —R, halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$; or two R$^1$ groups, together with the atom or atoms to which each is attached, may form a fused or spiro ring selected from C$_{5-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

Z is —R, halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

each R$^a$ is independently —R, halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

each R is independently hydrogen, C$_{1-6}$ aliphatic, C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

m is 1 or 2;

n is 0, 1, 2, or 3; and p is 0, 1, or 2.

In certain embodiments, X is -halogen, -haloalkyl, —OR, —C(O)R, —CO$_2$R, —C(O)N(R)$_2$, —NRC(O)R, —NRSO$_2$R, or —N(R)$_2$; or X is an optionally substituted C$_{1-6}$ aliphatic.

In certain embodiments, X is -halogen, -haloalkyl, or an optionally substituted C$_{1-6}$ aliphatic.

In certain embodiments, X is F, Cl, Br, I, CF$_3$, methyl, ethyl, n-propyl, i-propyl, n-butyl, s-butyl, t-butyl, straight chain or branched pentyl, straight chain or branched hexyl.

In certain embodiments, X is Cl, Me, or CF$_3$.

In certain embodiments, Y is O, C(O), CO$_2$, C(O)N(R), NRC(O), NRSO$_2$, or N(R).

In certain embodiments, Y is O, C(O), CO$_2$, C(O)NH, NHC(O), NHSO$_2$, or NH.

In certain embodiments, Y is C(O), CO$_2$, C(O)NH, NHC(O), or NHSO$_2$.

In certain embodiments, Y is

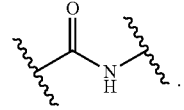

In certain embodiments, Ring A is an optionally substituted C$_{5-10}$ aryl. In certain embodiments, Ring A is an optionally substituted 3-8 membered saturated or partially unsaturated carbocyclic ring. In certain embodiments, Ring A is an optionally substituted 3-7 membered heterocylic ring having 1-4 heteroatoms independently selected from nitrogen, oxygen, or sulphur. In certain embodiments, Ring A is an optionally substituted 5-6 membered monocyclic heteroaryl ring having 1-4 heteroatoms independently selected from nitrogen, oxygen, or sulfur.

In certain embodiments, Ring A is an optionally substituted $C_{5-10}$ aryl or an optionally substituted 3-8 membered saturated or partially unsaturated carbocyclic ring.

In certain embodiments, Ring A is phenyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl.

In certain embodiments, Ring A is phenyl, cyclopropyl, cyclobutyl, cyclopentyl, cyclohexyl, or cycloheptyl.

In certain embodiments, Ring A is

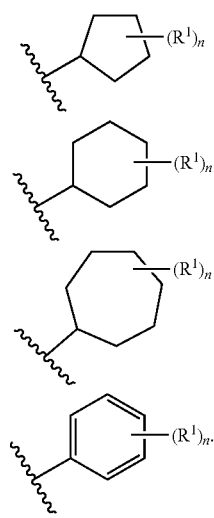

In certain embodiments, each $R^1$ is independently H.

In certain embodiments, each $R^1$ is independently —R, halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^1$ is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^1$ is independently halogen, -haloalkyl, -hydroxyalkyl, —OR, —C(O)R, —CO$_2$R, —C(O)N(R)$_2$, —NRC(O)R, —NRSO$_2$R, or —N(R)$_2$.

In certain embodiments, each $R^1$ is independently methyl, ethyl, n-propyl, i-propyl, n-butyl, s-butyl, t-butyl, straight chain or branched pentyl, straight chain or branched hexyl, OH, F, Cl, Br, I, or CF$_3$.

In certain embodiments, two $R^1$ groups, together with the atom or atoms to which each is attached, may form a fused or spiro ring selected from an optionally substituted 3-8 membered saturated or partially unsaturated carbocyclic ring, or a an optionally substituted 3-7 membered heterocylic ring having 1-4 heteroatoms independently selected from nitrogen, oxygen, or sulfur.

In certain embodiments, two $R^1$ groups, together with the atom or atoms to which each is attached, may form a fused or spiro ring selected from cyclopropyl, cyclobutyl, cyclopentyl, cyclohexyl, and cycloheptyl.

In certain embodiments, Ring A is

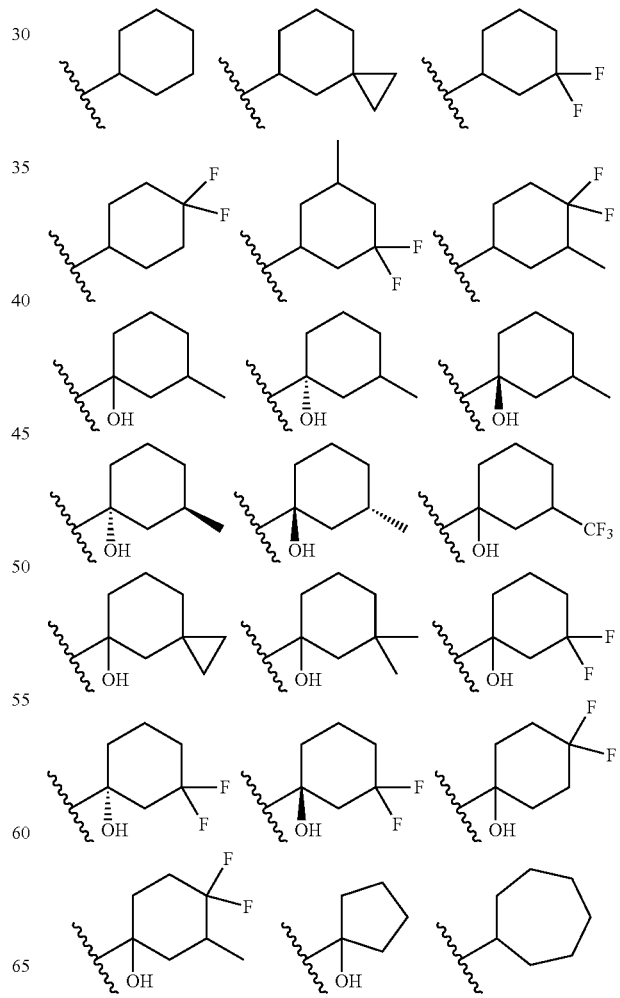

-continued

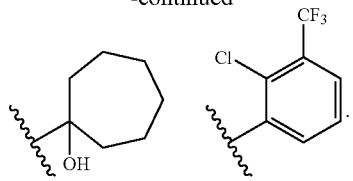

In certain embodiments, Z is H.

In certain embodiments, Z is —R, halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, Z is halogen. In certain embodiments, Z is I.

In certain embodiments, Z is C$_{1-6}$ aliphatic, C$_3$-10 aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, Z is C$_{1-6}$ aliphatic, a 3-8 membered saturated or partially unsaturated carbocyclic ring, or a 3-7 membered heterocyclic ring having 1-4 heteroatoms independently selected from nitrogen, oxygen, or sulfur; each of which is optionally substituted.

In certain embodiments, Z is

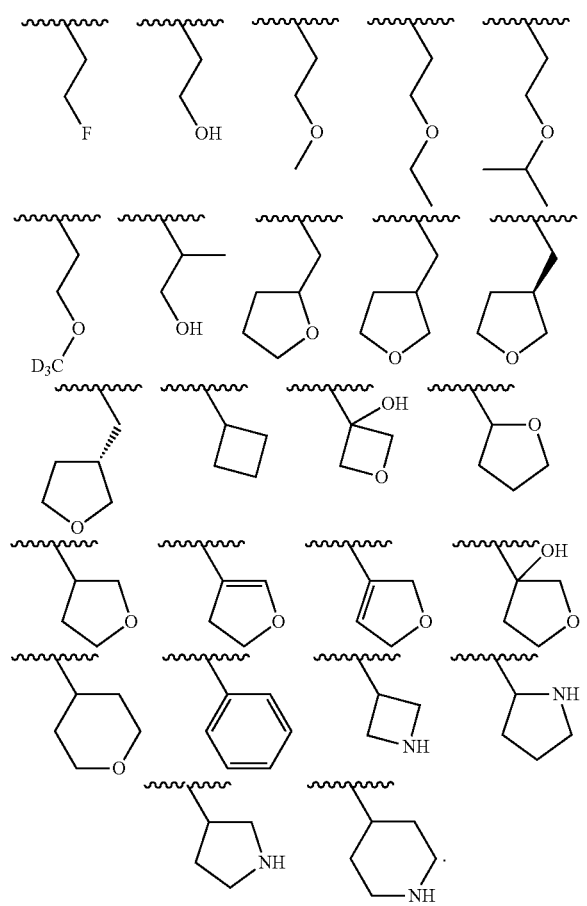

In certain embodiments, m is 1. In certain embodiments, m is 2.

In certain embodiments, n is 0. In certain embodiments, n is 1. In certain embodiments, n is 2.

In certain embodiments, p is 0. In certain embodiments, p is 1. In certain embodiments, p is 2.

In certain embodiments, each of Ring A, X, Y, Z, R$^1$, R$^a$, m, n, and p, is as defined above and described in embodiments, classes and subclasses above and herein, singly or in combination.

In certain embodiments, the present invention provides a compound of formula II,

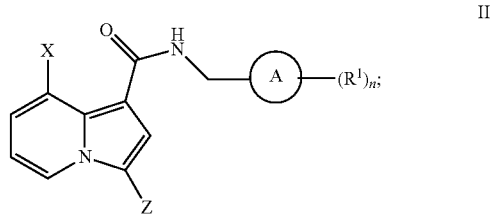

II or a pharmaceutically acceptable salt thereof, wherein each of Ring A, X, Z, R$^1$, and n is as defined above and described in embodiments, classes and subclasses above and herein, singly or in combination.

In certain embodiments, the present invention provides a compound of formula III:

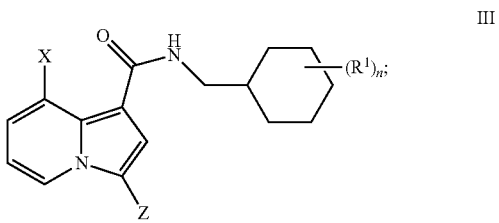

III or a pharmaceutically acceptable salt thereof, wherein each of X, Z, R$^1$, and n is as defined above and described in embodiments, classes and subclasses above and herein, singly or in combination.

In certain embodiments, the present invention provides a compound of formula IV:

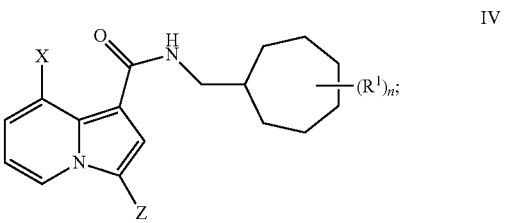

IV or a pharmaceutically acceptable salt thereof, wherein each of X, Z, R$^1$, and n, is as defined above and described in embodiments, classes and subclasses above and herein, singly or in combination.

In certain embodiments, the present invention provides a compound of formula V:

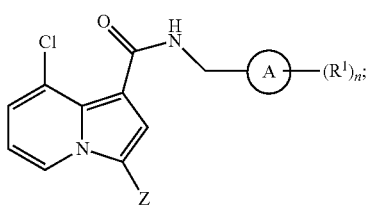

V or a pharmaceutically acceptable salt thereof, wherein each of Ring A, Z, R¹, and n, is as defined above and described in embodiments, classes and subclasses above and herein, singly or in combination.

In certain embodiments, the present invention provides a compound of formula VI:

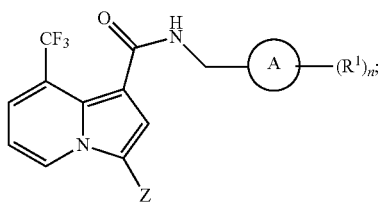

VI or a pharmaceutically acceptable salt thereof, wherein each of Ring A, Z, R¹, and n, is as defined above and described in embodiments, classes and subclasses above and herein, singly or in combination.

In certain embodiments, the invention provides a compound selected from Table 1:

TABLE 1

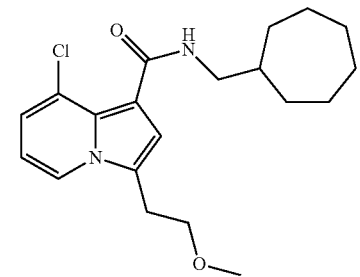 [SMILES: COCCc1cc(C(=O)NCC2CCCCCC2)c2c(Cl)cccn12]

1

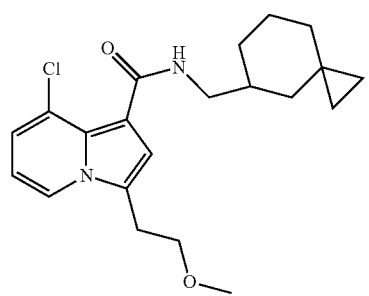 [SMILES: COCCc1cc(C(=O)NCC2CCCC3(CC3)C2)c2c(Cl)cccn12]

2

TABLE 1-continued

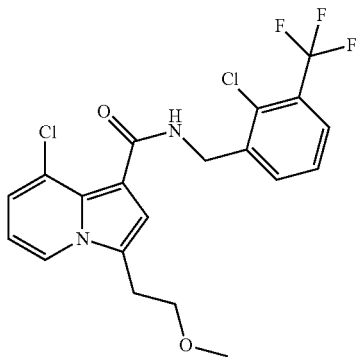 [SMILES: COCCc1cc(C(=O)NCc2cccc(C(F)(F)F)c2Cl)c2c(Cl)cccn12]

3

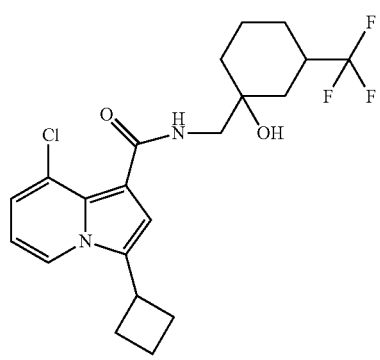 [SMILES: O=C(NCC1(O)CCCC(C(F)(F)F)C1)c1cc(C2CCC2)n2cccc(Cl)c12]

4

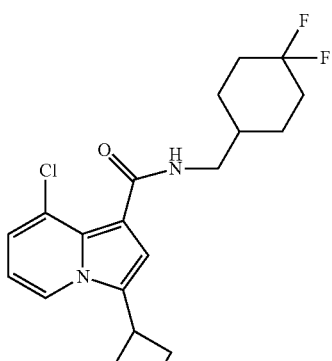

5

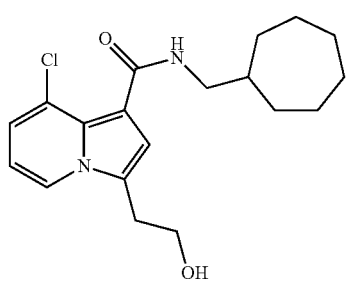 [SMILES: O=C(NCC1CCCCCC1)c1cc(CCO)n2cccc(Cl)c12]

6

TABLE 1-continued
7
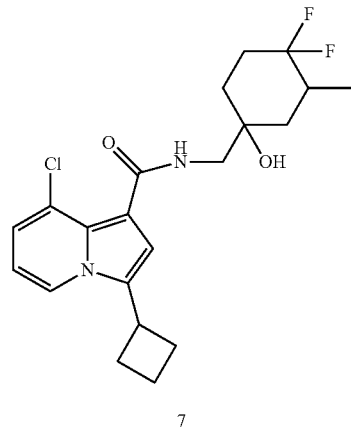
8
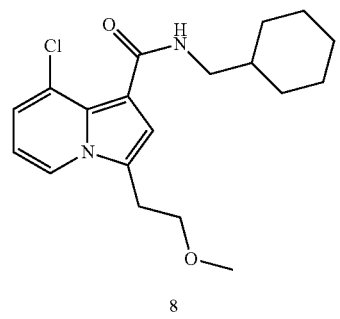
9
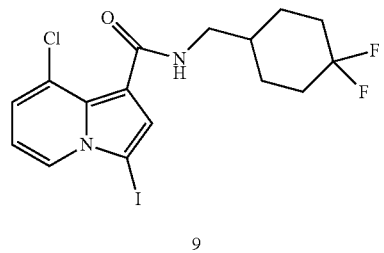
10
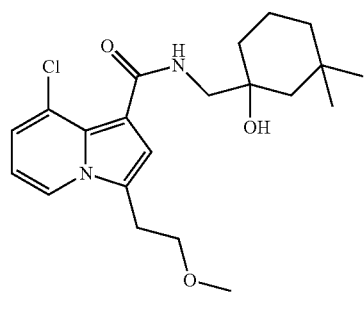 [SMILES: COCCc1cc(C(=O)NCC2(O)CCCC(C)(C)C2)c2c(Cl)cccn12]
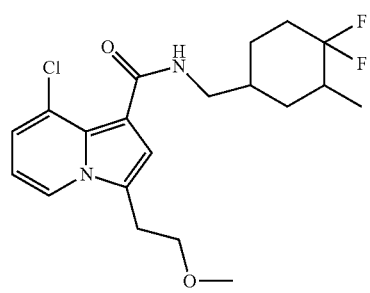 [SMILES: COCCc1cc(C(=O)NCC2CCC(F)(F)C(C)C2)c2c(Cl)cccn12]
TABLE 1-continued
11
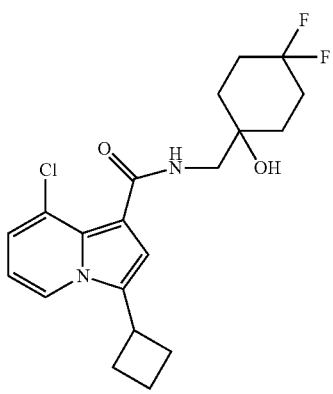 [SMILES: O=C(NCC1(O)CCC(F)(F)CC1)c1cc(C2CCC2)n2cccc(Cl)c12]
12
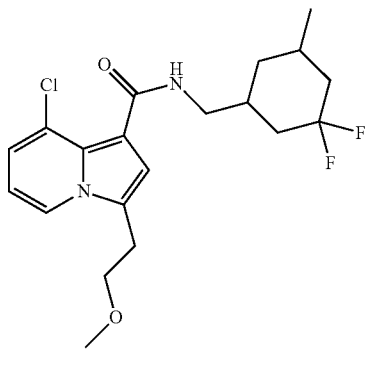 [SMILES: COCCc1cc(C(=O)NCC2CC(C)CC(F)(F)C2)c2c(Cl)cccn12]
13
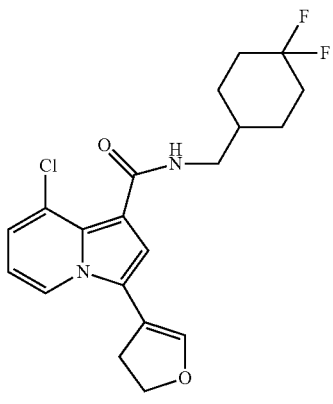 [SMILES: O=C(NCC1CCC(F)(F)CC1)c1cc(C2=COCC2)n2cccc(Cl)c12]
14
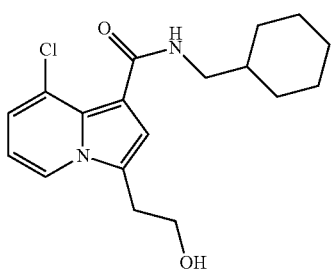 [SMILES: O=C(NCC1CCCCC1)c1cc(CCO)n2cccc(Cl)c12]
15

TABLE 1-continued
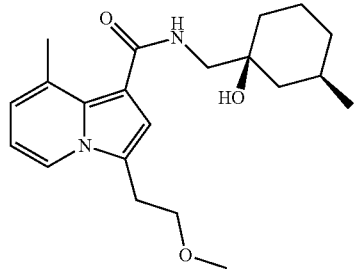 [SMILES: COCCc1cc(C(=O)NC[C@]2(O)CCC[C@@H](C)C2)c2c(C)cccn12]
16
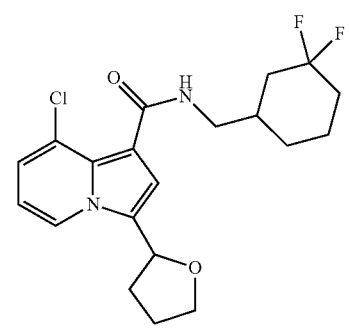 [SMILES: O=C(NCC1CCCC(F)(F)C1)c1cc(C2CCCO2)n2cccc(Cl)c12]
17
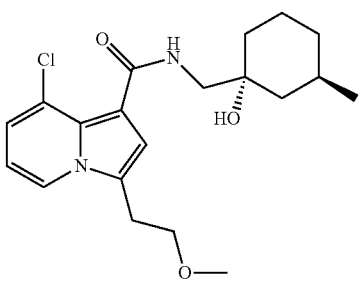 [SMILES: COCCc1cc(C(=O)NC[C@@]2(O)CCC[C@@H](C)C2)c2c(Cl)cccn12]
18
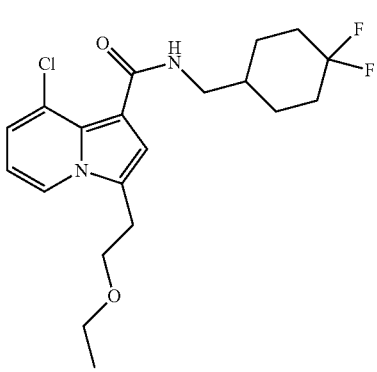 [SMILES: CCOCCc1cc(C(=O)NCC2CCC(F)(F)CC2)c2c(Cl)cccn12]
19
TABLE 1-continued
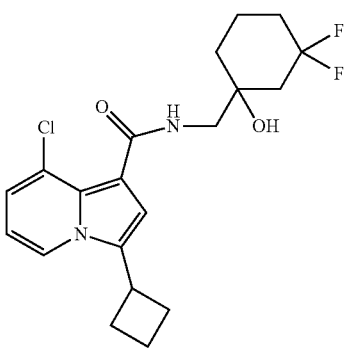 [SMILES: O=C(NCC1(O)CCCC(F)(F)C1)c1cc(C2CCC2)n2cccc(Cl)c12]
20
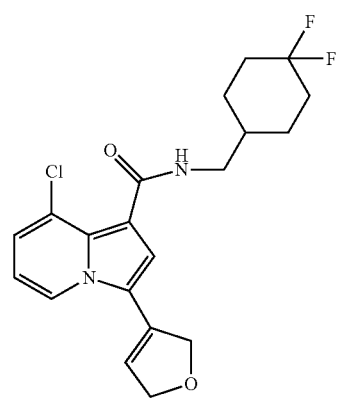 [SMILES: O=C(NCC1CCC(F)(F)CC1)c1cc(C2=CCOC2)n2cccc(Cl)c12]
21
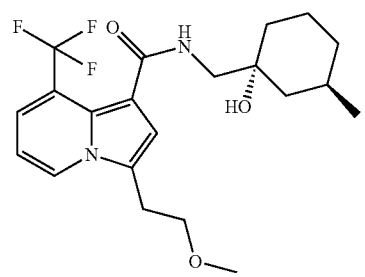 [SMILES: COCCc1cc(C(=O)NC[C@@]2(O)CCC[C@@H](C)C2)c2c(C(F)(F)F)cccn12]
22
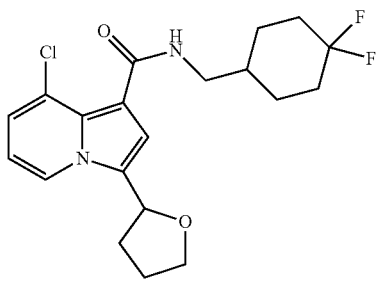 [SMILES: O=C(NCC1CCC(F)(F)CC1)c1cc(C2CCCO2)n2cccc(Cl)c12]
23

TABLE 1-continued
24
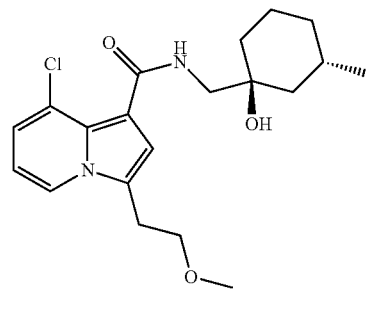 [SMILES: COCCc1cc(C(=O)NC[C@]2(O)CCC[C@H](C)C2)c2c(Cl)cccn12]
25
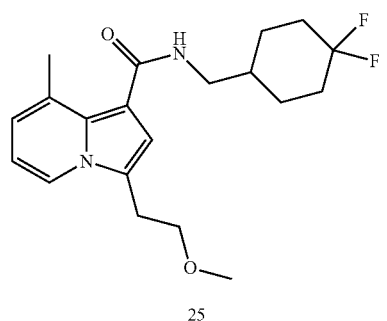
26
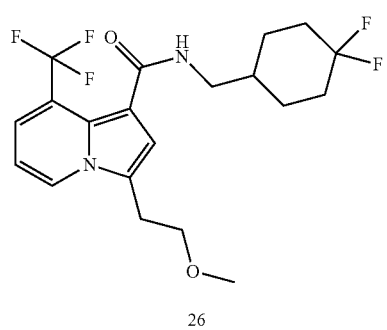
27
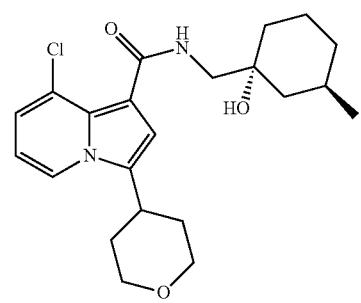 [SMILES: C[C@@H]1CCC[C@](O)(CNC(=O)c2cc(C3CCOCC3)n3cccc(Cl)c23)C1]
28
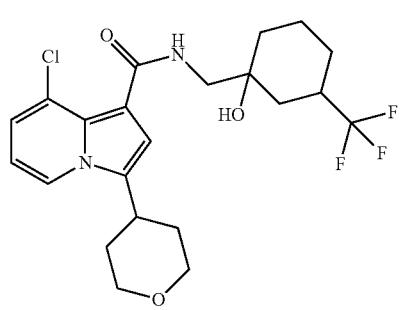 [SMILES: O=C(NCC1(O)CCCC(C(F)(F)F)C1)c1cc(C2CCOCC2)n2cccc(Cl)c12]
TABLE 1-continued
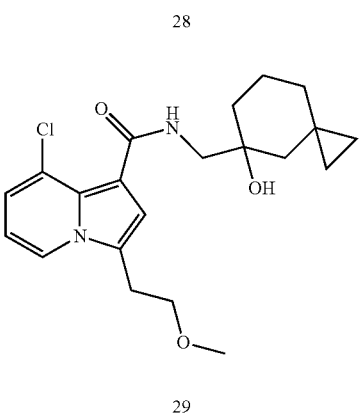
29
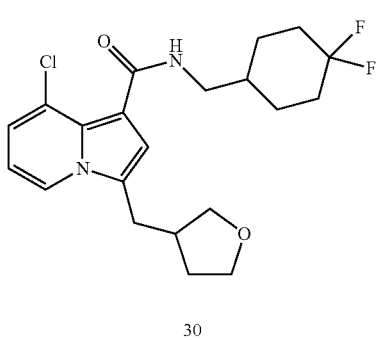
30
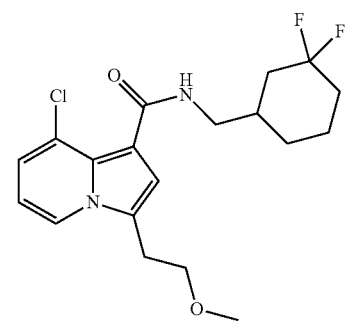 [SMILES: COCCc1cc(C(=O)NCC2CCCC(F)(F)C2)c2c(Cl)cccn12]
31
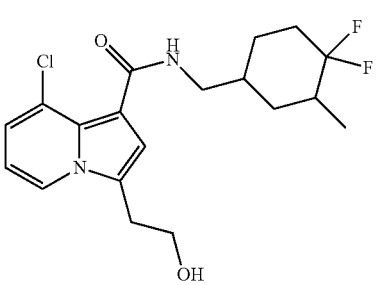 [SMILES: CC1CC(CNC(=O)c2cc(CCO)n3cccc(Cl)c23)CCC1(F)F]
32

TABLE 1-continued
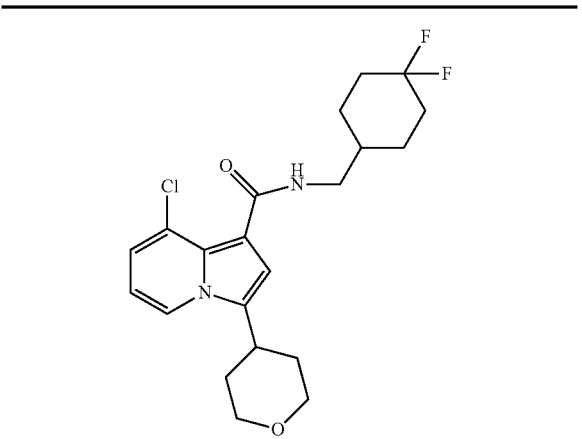
33
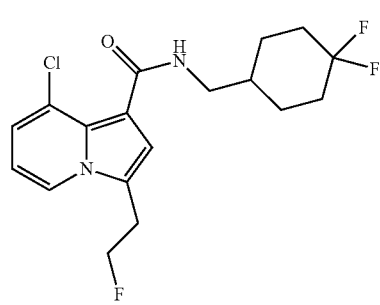 [SMILES: O=C(NCC1CCC(F)(F)CC1)c1cc(CCF)n2cccc(Cl)c12]
34
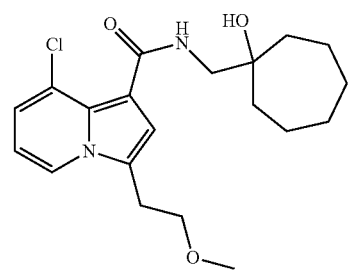 [SMILES: COCCc1cc(C(=O)NCC2(O)CCCCCC2)c2c(Cl)cccn12]
35
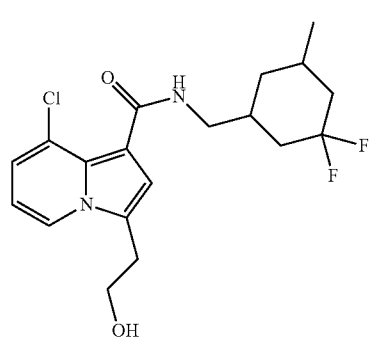 [SMILES: CC1CC(CNC(=O)c2cc(CCO)n3cccc(Cl)c23)CC(F)(F)C1]
36
TABLE 1-continued
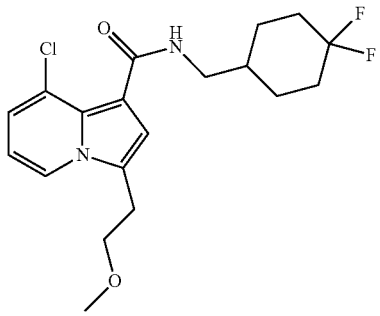 [SMILES: COCCc1cc(C(=O)NCC2CCC(F)(F)CC2)c2c(Cl)cccn12]
37
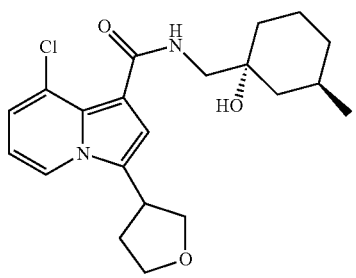 [SMILES: C[C@@H]1CCC[C@](O)(CNC(=O)c2cc(C3CCOC3)n3cccc(Cl)c23)C1]
38
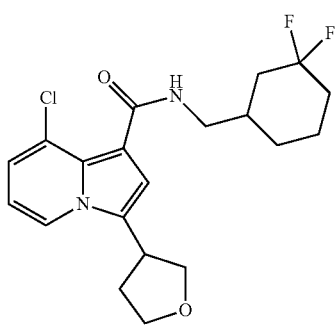 [SMILES: O=C(NCC1CCCC(F)(F)C1)c1cc(C2CCOC2)n2cccc(Cl)c12]
39
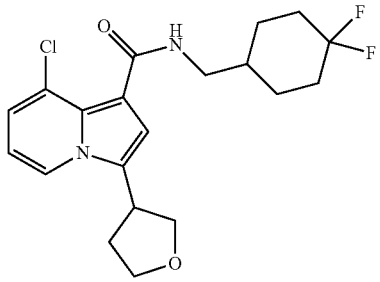 [SMILES: O=C(NCC1CCC(F)(F)CC1)c1cc(C2CCOC2)n2cccc(Cl)c12]
40

TABLE 1-continued
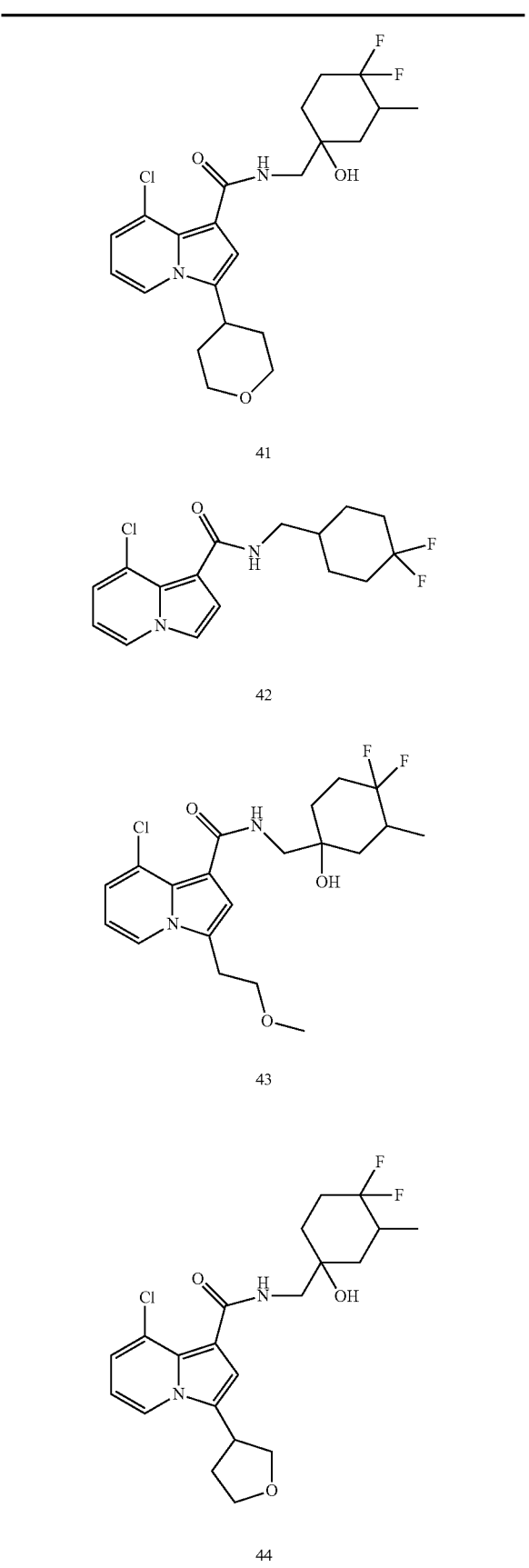
41
42
43
44
TABLE 1-continued
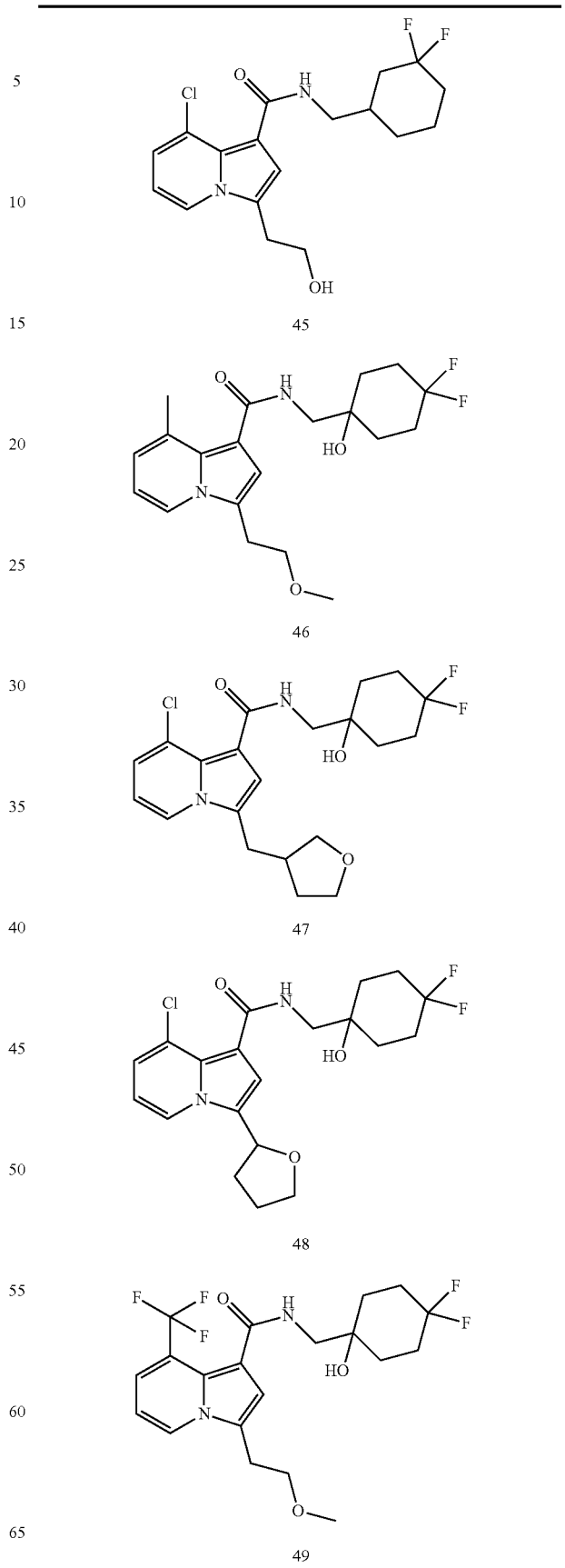
45
46
47
48
49

TABLE 1-continued
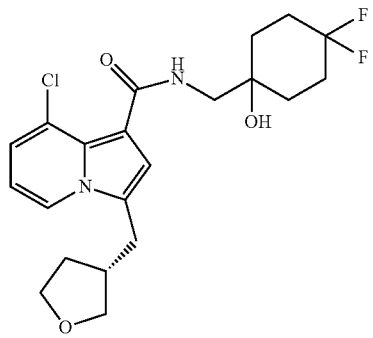 [SMILES: O=C(NCC1(O)CCC(F)(F)CC1)c1cc(C[C@H]2CCOC2)n2cccc(Cl)c12]
50
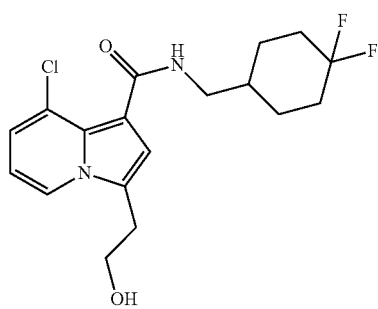 [SMILES: O=C(NCC1CCC(F)(F)CC1)c1cc(CCO)n2cccc(Cl)c12]
51
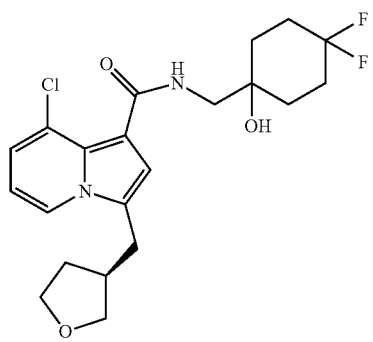 [SMILES: O=C(NCC1(O)CCC(F)(F)CC1)c1cc(C[C@@H]2CCOC2)n2cccc(Cl)c12]
52
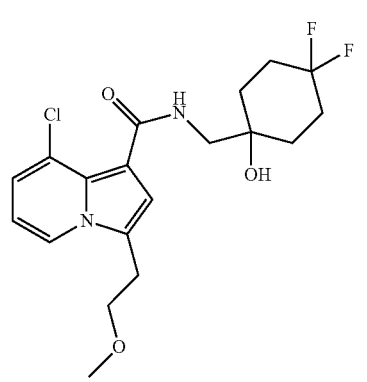 [SMILES: COCCc1cc(C(=O)NCC2(O)CCC(F)(F)CC2)c2c(Cl)cccn12]
53
TABLE 1-continued
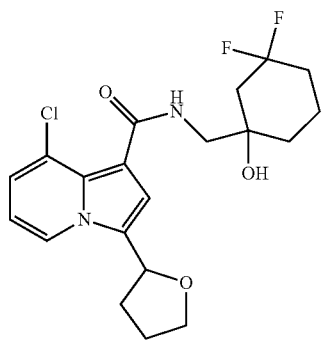 [SMILES: O=C(NCC1(O)CCCC(F)(F)C1)c1cc(C2CCCO2)n2cccc(Cl)c12]
54
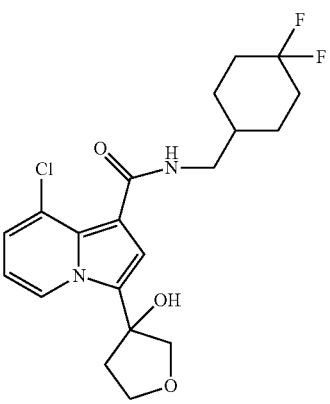 [SMILES: O=C(NCC1CCC(F)(F)CC1)c1cc(C2(O)CCOC2)n2cccc(Cl)c12]
55
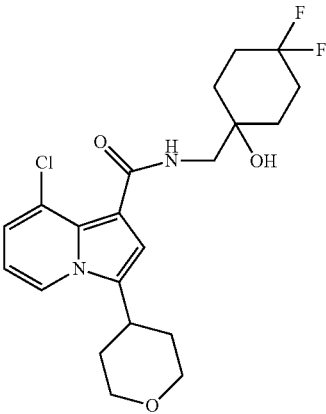 [SMILES: O=C(NCC1(O)CCC(F)(F)CC1)c1cc(C2CCOCC2)n2cccc(Cl)c12]
56
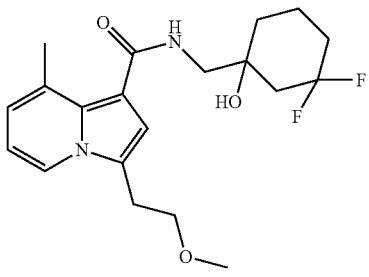 [SMILES: COCCc1cc(C(=O)NCC2(O)CCCC(F)(F)C2)c2c(C)cccn12]
57

TABLE 1-continued
58
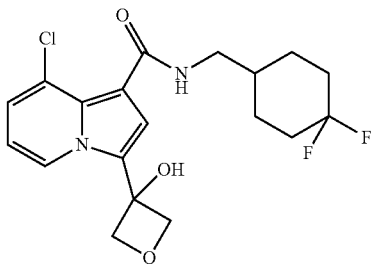 [SMILES: O=C(NCC1CCC(F)(F)CC1)c1cc(C2(O)COC2)n2cccc(Cl)c12]
59
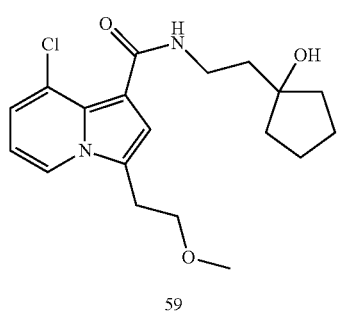
60
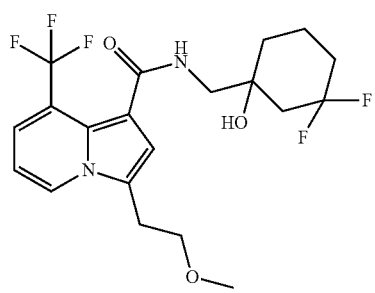 [SMILES: COCCc1cc(C(=O)NCC2(O)CCCC(F)(F)C2)c2c(C(F)(F)F)cccn12]
61
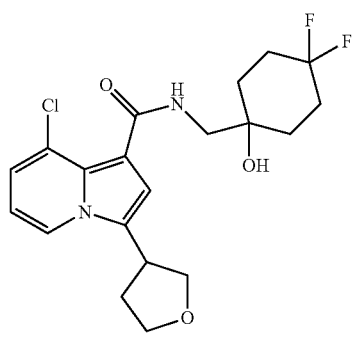 [SMILES: O=C(NCC1(O)CCC(F)(F)CC1)c1cc(C2CCOC2)n2cccc(Cl)c12]
62
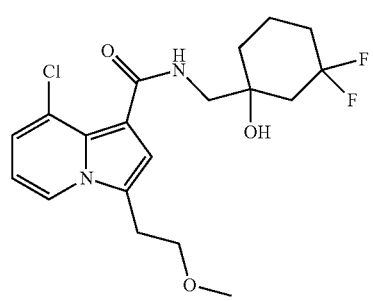 [SMILES: COCCc1cc(C(=O)NCC2(O)CCCC(F)(F)C2)c2c(Cl)cccn12]
TABLE 1-continued
63
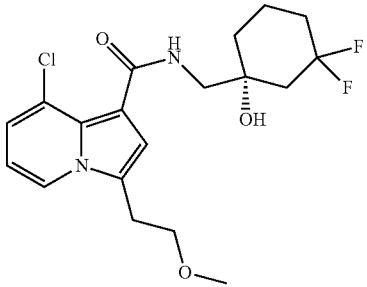 [SMILES: COCCc1cc(C(=O)NC[C@@]2(O)CCCC(F)(F)C2)c2c(Cl)cccn12]
64
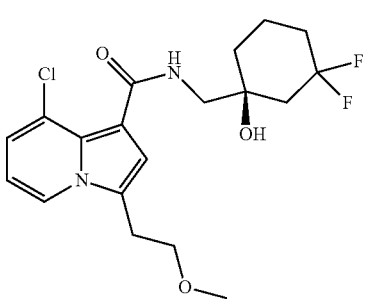 [SMILES: COCCc1cc(C(=O)NC[C@]2(O)CCCC(F)(F)C2)c2c(Cl)cccn12]
65
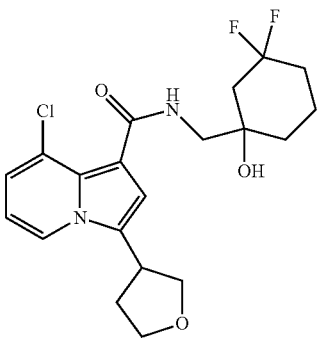 [SMILES: O=C(NCC1(O)CCCC(F)(F)C1)c1cc(C2CCOC2)n2cccc(Cl)c12]
66
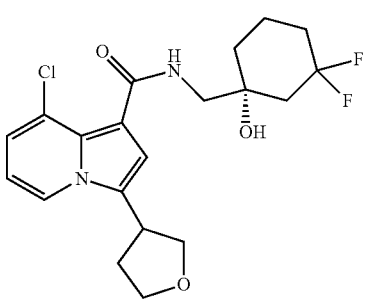 [SMILES: O=C(NC[C@@]1(O)CCCC(F)(F)C1)c1cc(C2CCOC2)n2cccc(Cl)c12]

TABLE 1-continued
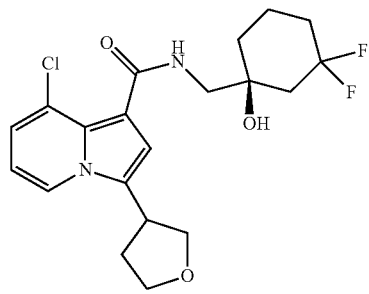 [SMILES: O=C(NC[C@]1(O)CCCC(F)(F)C1)c1cc(C2CCOC2)n2cccc(Cl)c12]
67
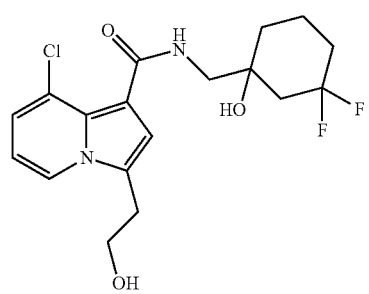 [SMILES: O=C(NCC1(O)CCCC(F)(F)C1)c1cc(CCO)n2cccc(Cl)c12]
68
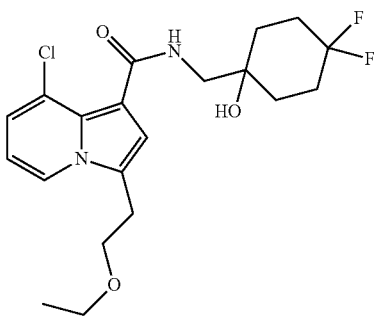 [SMILES: CCOCCc1cc(C(=O)NCC2(O)CCC(F)(F)CC2)c2c(Cl)cccn12]
69
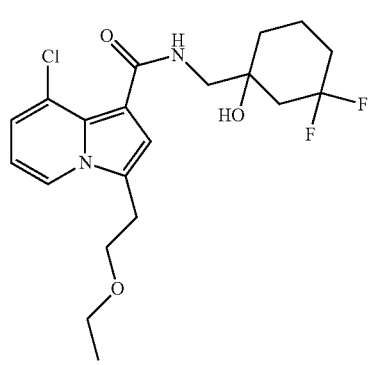 [SMILES: CCOCCc1cc(C(=O)NCC2(O)CCCC(F)(F)C2)c2c(Cl)cccn12]
70
TABLE 1-continued
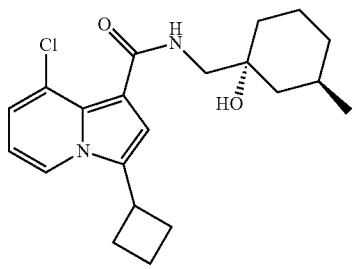 [SMILES: C[C@@H]1CCC[C@](O)(CNC(=O)c2cc(C3CCC3)n3cccc(Cl)c23)C1]
71
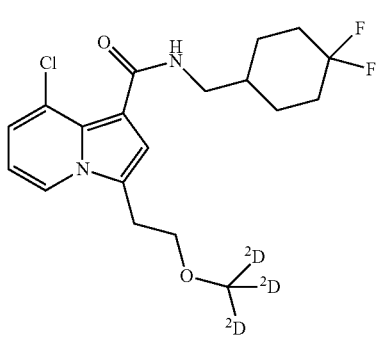 [SMILES: [2H]C([2H])([2H])OCCc1cc(C(=O)NCC2CCC(F)(F)CC2)c2c(Cl)cccn12]
72
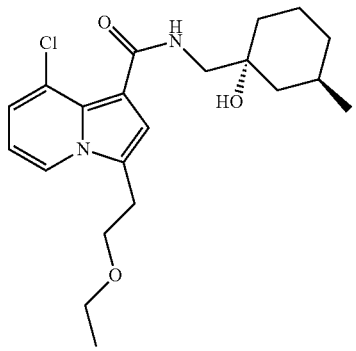 [SMILES: CCOCCc1cc(C(=O)NC[C@@]2(O)CCC[C@@H](C)C2)c2c(Cl)cccn12]
73
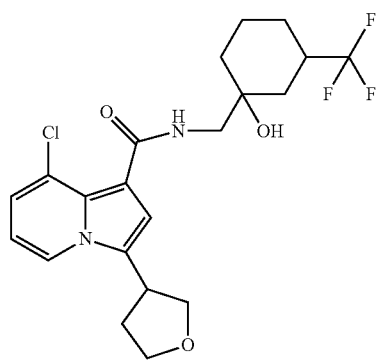 [SMILES: O=C(NCC1(O)CCCC(C(F)(F)F)C1)c1cc(C2CCOC2)n2cccc(Cl)c12]
74

TABLE 1-continued
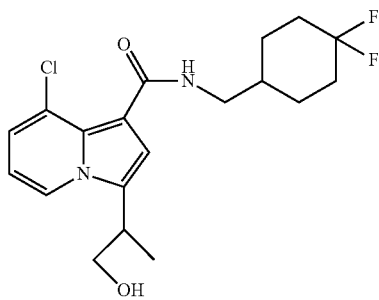 [SMILES: CC(CO)c1cc(C(=O)NCC2CCC(F)(F)CC2)c2c(Cl)cccn12]
75
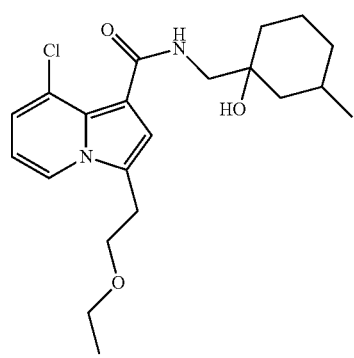 [SMILES: CCOCCc1cc(C(=O)NCC2(O)CCCC(C)C2)c2c(Cl)cccn12]
76
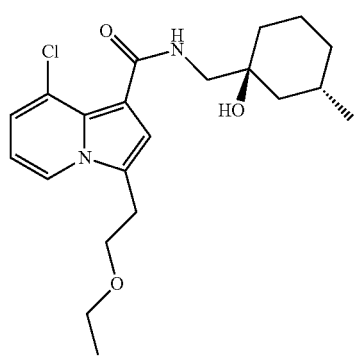 [SMILES: CCOCCc1cc(C(=O)NC[C@]2(O)CCC[C@H](C)C2)c2c(Cl)cccn12]
77
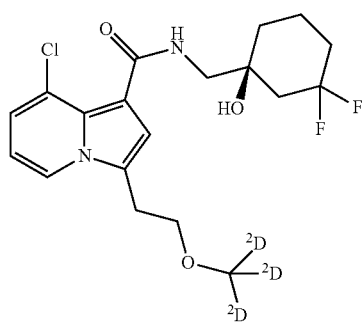 [SMILES: [2H]C([2H])([2H])OCCc1cc(C(=O)NC[C@]2(O)CCCC(F)(F)C2)c2c(Cl)cccn12]
78
TABLE 1-continued
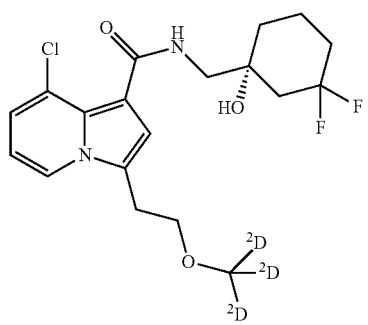 [SMILES: [2H]C([2H])([2H])OCCc1cc(C(=O)NC[C@@]2(O)CCCC(F)(F)C2)c2c(Cl)cccn12]
79
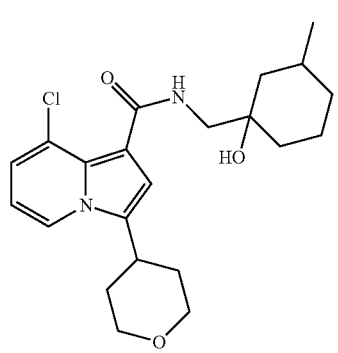 [SMILES: CC1CCCC(O)(CNC(=O)c2cc(C3CCOCC3)n3cccc(Cl)c23)C1]
80
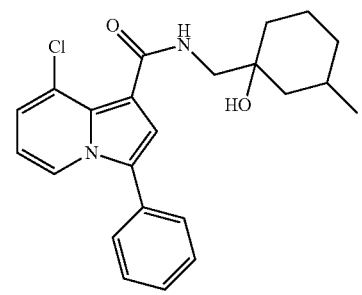 [SMILES: CC1CCCC(O)(CNC(=O)c2cc(-c3ccccc3)n3cccc(Cl)c23)C1]
81
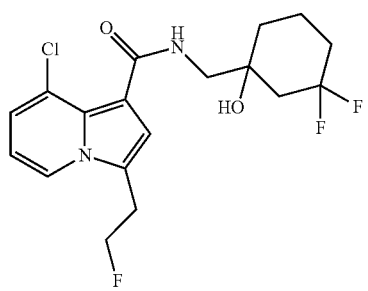 [SMILES: O=C(NCC1(O)CCCC(F)(F)C1)c1cc(CCF)n2cccc(Cl)c12]
82

TABLE 1-continued

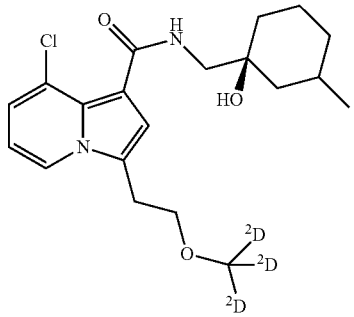 [SMILES: [2H]C([2H])([2H])OCCc1cc(C(=O)NC[C@]2(O)CCCC(C)C2)c2c(Cl)cccn12]

83

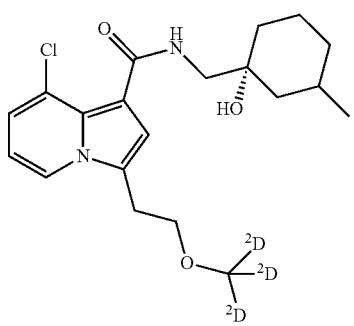 [SMILES: [2H]C([2H])([2H])OCCc1cc(C(=O)NC[C@@]2(O)CCCC(C)C2)c2c(Cl)cccn12]

84

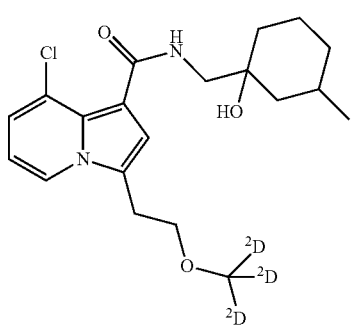 [SMILES: [2H]C([2H])([2H])OCCc1cc(C(=O)NCC2(O)CCCC(C)C2)c2c(Cl)cccn12]

85

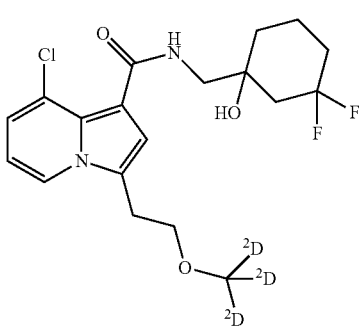 [SMILES: [2H]C([2H])([2H])OCCc1cc(C(=O)NCC2(O)CCCC(F)(F)C2)c2c(Cl)cccn12]

86

TABLE 1-continued

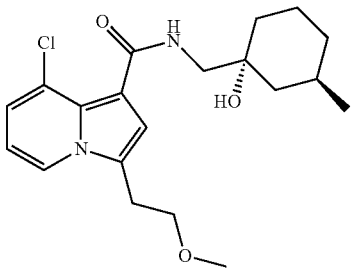 [SMILES: COCCc1cc(C(=O)NC[C@@]2(O)CCC[C@@H](C)C2)c2c(Cl)cccn12]

87

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

OH).

In certain embodiments, the compounds of the invention were synthesized in accordance with Schemes below. More specific examples of compounds made utilizing the Schemes are provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate P2X7 in a biological sample or in a patient. In certain embodiments, the amount of compound in compositions of this invention is such that is effective to measurably modulate P2X7 in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation is also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for antagonizing P2X7 in a positive manner in a patient or in a biological sample comprising the step of administering to said patient or contacting said biological sample with a compound according to the invention.

In certain embodiments, the invention is directed to the use of compounds of the invention and/or physiologically acceptable salts thereof, for antagonizing P2X7. The compounds are characterized by such a high affinity to P2X7, which ensures a reliable binding and preferably antagonization of P2X7. In certain embodiments, the substances are mono-specific in order to guarantee an exclusive and directed recognition with the single P2X7 target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

In certain embodiments, the present invention relates to a method for antagonizing P2X7 with at least one compound of formula (I) according to the invention and/or physiologically acceptable salts thereof, under conditions such that said P2X7 receptor is antagonized. In certain embodiments, the system is a cellular system. In other embodiments, the system is an in-vitro translation which is based on the protein synthesis without living cells. The cellular system is defined to be any subject provided that the subject comprises cells. Hence, the cellular system can be selected from the group of single cells, cell cultures, tissues, organs and animals. In certain embodiments, the method for antagonizing P2X7 is performed in-vitro. The prior teaching of the present specification concerning the compounds of formula (I), including any embodiments thereof, is valid and applicable without restrictions to the compounds according to formula (I) and their salts when used in the method for antagonizing P2X7. The prior teaching of the present specification concerning the compounds of formula (I), including any embodiments thereof, is valid and applicable without restrictions to the compounds according to formula (I) and their salts when used in the method for antagonizing P2X7.

In certain embodiments, the compounds according to the invention exhibit an advantageous biological activity, which is easily demonstrated in cell culture-based assays, for example assays as described herein or in prior art (cf. e.g. WO 2002/09706, which is incorporated herein by reference). In such assays, the compounds according to the invention preferably exhibit and cause an agonistic effect.

In certain embodiments, the invention provides a method for preventing, treating or ameliorating in a subject a disease, disorder, or condition that is causally related to the aberrant activity of P2X7 receptor, which comprises administering to the subject a therapeutically effective amount of a compound of any formulae herein, or a pharmaceutically acceptable salt thereof. In certain embodiments, the disease or disorder is an autoimmune, inflammatory or cardiovascular disease or disorder.

In certain embodiments, the disease or disorder is a neurodegenerative disease or disorder, including Parkinson's disease, multiple sclerosis (MS); Alzheimer's disease, diseases and disorders which are mediated by or result in neuroinflammation such as, for example traumatic brain injury, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and renal disorders.

In certain embodiments, the disease or disorder is pain, including acute, inflammatory and neuropathic pain, chronic pain, dental pain and headache including migraine, cluster headache and tension headache.

In certain embodiments, the disease or disorder is rheumatoid arthritis, osteoarthritis, psoriasis, allergic dermatitis, asthma, hyperresponsiveness of the airway, chronic obstructive pulmonary disease (COPD), bronchitis, septic shock, glomerulonephritis, irritable bowel disease, Crohn's disease, ulcerative colitis, atherosclerosis, growth and metastases of malignant cells, myoblastic leukaemia, diabetes, neurodegenerative disease, Alzheimer's disease, multiple sclerosis, meningitis, osteoporosis, burn injury, ischaemic heart disease, stroke, peripheral vascular disease, varicose veins, glaucoma, bipolar disorder, and neuropathic pain conditions such as diabetic neuropathy, post-herpatic neuralgia, low back pain, chemotherapy-induced neuropathic pain, fibromyalgia and spinal cord injury pain.

In certain embodiments, the present invention is used when the use of compounds which inhibit the P2X7 receptor are expected to improve pathological conditions. Such cases include, for example, prevention and therapy of swelling, exacerbation of pain and bone metabolism in rheumatoid arthritis, prevention and therapy of inflammatory bowel diseases, chronic obstructive pulmonary disease (COPD) and osteoarthritis, prevention and therapy of inflammatory pain and cancer pain and IL-1β-associated diseases such as Crohn's disease, emphysema, acute respiratory distress syndrome, adult respiratory distress syndrome, asthma, bronchitis, chronic pulmonary inflammatory diseases, silicosis, pulmonary sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, loosening of artificial joint implants, atherosclerosis, aortic aneurysm, congestive heart failure, myocardial infarction, stroke, cerebral ischemia, head trauma, neurotrauma, spinal cord injury, neurodegenerative disorder, Alzheimer's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, corneal scarring, scleritis, abnormal wound healing, burns, autoimmune diseases, Huntington's disease, diabetes, AIDS, cachexia, sepsis, septic shock, endotoxin shock, conjunctivitis shock, gram-negative sepsis, toxic shock syndrome, cerebral malaria, cardiac and renal reperfusion injury, thrombosis, glomerulonephritis, graft-versus-host reaction, homograft rejection, organ transplant toxicity, ulcerative colitis or muscle degeneration.

In certain embodiments, the present invention encompasses a method of treating a patient suffering from a mood disorder, including those suffering from a treatment resistant form of depression, comprising administering a therapeutically effective amount of a modulator of P2X7 receptor activity to a subject suffering from said affective disorder. It is understood that the mood disorder may be one among many of the disorders affecting mood and behavior. For example, mood disorders comprise depressive disorder (that includes major depressive disorder, dysthymic disorder), bipolar disorder (includes bipolar I disorder, bipolar II disorder, cyclothymic disorder), mood disorder due to a general medical condition and substance-induced mood disorder (American Psychiatric Association: Diagnostic and Statistical Manual of Mental Disorders (DSM-IV-TR), Fourth Edition, Text Revision. Washington, D.C., American Psychiatric Association, pages 345-428, 2000.). In certain embodiments, the disorder is a depressive disorder. The present invention also encompasses a method of treating a patient suffering from an anxiety disorder. Anxiety disorders include: panic attack, agoraphobia, specific phobia, social phobia, obsessive-compulsive disorder, posttraumatic stress disorder, acute stress disorder, and generalized anxiety disorder.

In certain embodiments, the disease or disorder is pain, selected from pain associated with postmastectomy pain syndrome, stump pain, phantom limb pain, oral neuropathic pain, Charcot's pain, toothache, venomous snake bite, spider bite, insect sting, postherpetic neuralgia, diabetic neuropathy, reflex sympathetic dystrophy, trigeminal neuralgia, osteoarthritis, rheumatoid arthritis, fibromyalgis, Guillain-Barre syndrome, meralgia paresthetica, burning-mouth syndrome, bilateral peripheral neuropathy, causalgia, sciatic neuritis, peripheral neuritis, polyneuritis, segmental neuritis, Gombault's neuritis, neuronitis, cervicobrachial neuralgia, cranial neuralgia, egniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia splenopalatine neuralgia, supraorbital neuralgia, vidian neuralgia, sinus headache, tension headache, labor, childbirth, intestinal gas, menstruation, cancer, and trauma.

In certain embodiments, the disease or disorder is associated with inflammation, including rheumatoid arthritis, osteoarthritis, uveitis, asthma, myocardial infarction, traumatic brain injury; septic shock, atherosclerosis, chronic pulmonary obstructive disease (COPD), acute spinal cord injury, inflammatory bowel disease and immune dysfunction.

In certain embodiments, the disease or disorder is associated with pain responses or imbalances in the maintenance of basal activity of sensory nerves. The amine compounds of the invention have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In certain embodiments, the disease or disorder is arthritis, uveitis, asthma, myocardial infarction, traumatic brain injury, acute spinal cord injury, or inflammatory bowel disease.

In certain embodiments, the disease or disorder is MS.

In certain embodiments, the disease or disorder is Parkinson's disease.

In certain embodiments, the disease or disorder is rheumatoid arthritis.

In certain embodiments, the disease or disorder is traumatic brain injury.

In certain embodiments, the disease or disorder is pain.

In other embodiments, the invention provides compounds of the invention for use as a pharmaceutical especially in the treatment or prevention of the aforementioned conditions and diseases. Also provided herein is the use of the present compounds in the manufacture of a medicament for the treatment or prevention of one of the aforementioned conditions and diseases. The present invention also provides the use of a compound of the invention or a pharmaceutically acceptable salt thereof for the manufacture of a medicament for the treatment of conditions or diseases selected from P2X7 receptor mediated conditions or diseases.

When used to prevent the onset of a P2X7 related disease/disorder, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

A compound of Formula (I) of the present invention can be administered as sole active agent or can be adminstered in combination with other agents. These agents include non-steroidal anti-inflammatory drug (NSAIDS) such as celecoxib, rofecoxib, cimicoxib, etoricoxib, lumiracoxib, valdecoxib, deracoxib, N-(2-cyclohexyloxynitrophenyl) methane sulphonamide, COX189, ABT963, JTE-522, GW-406381, LAS-34475, CS-706, PAC-10649, SVT-2016, GW-644784, tenidap, acetylsalicylic acid (aspirin), amoxiprin, benorilate, choline magnesium salicylate, diflunisal, faislamine, methyl salicylate, magnesium salicylate, salicyl salicylate (salsalatee), diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, oxaprozin, tiaprofenic acid, suprofen, mefenamic acid, meclofenamic acid, phenylbutazone, azapropazone, metamizole, oxyphenbutazone, sulfinpyrazone, piroxicam, lornoxicam, meloxicam, tenoxicam, nimesulide, licofelone, or paracetamol.

A compound of Formula (I) of the present invention can be combined with agents such as TNFα inhibitors such as anti-TNF monoclonal antibodies (such as Remicade, CDP-870 and D2E7) and TNF receptor immunoglobulin molecules (such as Enbrel), low dose methotrexate, lefunomide; ciclesonide; hydroxychloroquine, d-penicillamine, auranofin or parenteral or oral gold.

A compound of Formula (I) of the present invention can also be administered in combination with an inhibitor of proTNFalpha convertase enzyme (TACE) such as 3-Amino-N-hydroxy-a-(2-methylpropyl)-3-[4-[(2-methyl-4-quinolinyl)methoxy]phenyl]-2-oxo-1-pyrrolidineacetamide, 2(S),3(S)-Piperidinedicarboxamide, N3-hydroxy-1-methyl-N2-[4-[(2-methyl-4-quinolinyl)methoxy]phenyl], 3-Thiomorpholinecarboxamide, 4-[[4-(2-butynyloxy)phenyl]sulfonyl]-N-hydroxy-2,2-dimethyl, 5-Hexenoic acid, 3-[(hydroxyamino)carbonyl]-2-(2-methylpropyl)-6-phenyl-, 2-(2-methylpropyl)-2-(methylsulfonyl)hydrazide, (2R, 3S,5E), 2-Piperidinecarboxamide, N,5-dihydroxy-1-[[4-(1-naphthalenylmethoxy)phenyl]sulfonyl]-, (2R,5R), Pentanamide, 3-(formylhydroxyamino)-4-methyl-2-(2-methylpropyl)-N-[(1S,2S)-2-methyl-1-[(2-pyridinylamino)carbonyl]butyl]-, (2R,3S),2-Propenamide, N-hydroxy-3-[3-[[(4-methoxyphenyl)sulfonyl](1-methylethyl)amino]phenyl]-3-(3-pyridinyl)-, (2E), Benzamide, N-(2,4-dioxo-1,3,7-triazaspiro[4.4]non-9-yl)-4-[(2-methyl-4-quinolinyl)me-thoxy], Benzamide, N-[(1-acetyl-4-piperidinyl)(2,5-dioxo-4-imidazolidinyl)methyl]-4-[(2-methyl-4-quinolinyl)methoxy], or 2,4-Imidazolidinedione, 5-methyl-5-[[[4-[(2-methyl-4-quinolinyl)methoxy]phenyl]sulfonyl]methyl].

A compound of Formula (I) of the present invention can also be administered in combination with a corticosteroid such as budesonide, corticosterone, cortisol, cortisone acetate, prednisone, prednisolone, methylprednisolone, dexamethasone, betamethasone, triamcinolone, beclometasone, fludrocortisone acetate, deoxycorticosterone acetate (doca), or aldosterone.

A compound of Formula (I) of the present invention can further be administered in combination with a b2-adrenergic receptor agonist such as formoterol, salbutamol (albuterol), levalbuterol, terbutaline, pirbuterol, procaterol, metaproterenol, fenoterol, bitolterol mesylate, salmeterol, bambuterol, or clenbuterol.

A compound of Formula (I) of the present invention can further be administered in combination with an antidepressant drug such as sertraline, escitalopram, fluoxetine, bupropion, paroxetine, venlafaxine, trazodone, amitriptyline, citalopram, duloxetine, mirtazapine, nortriptyline, imipramine, or lithium.

A compound of Formula (I) of the present invention can further be administered in combination with an antipsychotic drug such as chlorpromazine, fluphenazine, perphenazine, prochlorperazine, thioridazine, trifluoperazine, mesoridazine, promazine, triflupromazine, levomepromazine, promethazine, chlorprothixene, flupenthixol, thiothixene, zuclopenthixol, haloperidol, droperidol, pimozide, melperone, benperidol, triperidol, clozapine, olanzapine, risperidone, quetiapine, ziprasidone, amisulpride, paliperidone, bifeprunox, or aripiprazole.

A compound of Formula (I) of the present invention can also be administered in combination with a leukotriene biosynthesis inhibitor, 5-lipoxygenase (5-LO) inhibitor or 5-lipoxygenase activating protein (FLAP) antagonist, for example, zileuton; ABT-761; fenleuton; tepoxalin; nicaraven; VIA-2291; etalocib; ketoprofen, Abt-79175; Abt-85761; N-(5-substituted) thiophene-2-alkylsulfonamides; TDT-070; licofelone; PEP-03; tenoxicam; 2,6-di-tert-butylphenol hydrazones; methoxytetrahydropyrans such as Zeneca ZD-2138; the compound SB-210661; pyridinyl-substituted 2-cyanonaphthalene compounds such as L-739-010; 2-cyanoquinoline compounds such as L-746-530; indole and quinoline compounds such as MK-591, MK-886, and BAY×1005.

A compound of Formula (I) of the present invention can be administered in combination with a receptor antagonists for leukotrienes LTB4, LTC4, LTD4, and LTE, for example, phenothiazin-3-ones such as L-651.392; amidino compounds such as CGS-25019c; benzoxalamines such as ontezolast; benzenecarboximidamides such as BIIL 284/260; and compounds such as zafirlukast, ablukast, montelukast, praniukast, verlukast (MK-679), RG-12525, Ro-245913, iralukast (CGP 45715A), BAY×7195, and masilukast.

A compound of Formula (I) of the present invention can also be administered in combination with a PDE4 inhibitor including inhibitors of the isoform PDE4D.

A compound of Formula (I) of the present invention can also be administered in combination with a antihistaminic H1 receptor antagonists including cetirizine, loratadine, desloratadine, fexofenadine, astemizole, azelastine, and chlorpheniramine. A compound of Formula (I) of the present invention can further be administered in combination with a gastroprotective H2 receptor antagonist.

A compound of Formula (I) of the present invention can yet further be administered in combination with an a1- and a2-adrenoceptor agonist vasoconstrictor sympathomimetic agent, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

A compound of Formula (I) of the present invention can be administered in combination with anticholinergic agents including ipratropium bromide; tiotropium bromide; oxitropium bromide; pirenzepine; and telenzepine. The present invention still further relates to the combination of a compound of the invention together with a b1- to b4-adrenoceptor agonists including metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

A compound of Formula (I) of the present invention can be administered in combination with an insulin-like growth factor type I (IGF-1) mimetic.

A compound of Formula (I) of the present invention can be administered in combination with an inhaled glucocorticoid with reduced systemic side effects, including, prednisone, prednisolone, flunisolide, triamcinolone acetonide, beclomethasone dipropionate, budesonide, fluticasone propionate, and mometasone furoate.

A compound of Formula (I) of the present invention can be administered in combination with (a) tryptase inhibitors; (b) platelet activating factor (PAF) antagonists; (c) interleukin converting enzyme (ICE) inhibitors; (d) IMPDH inhibitors; (e) adhesion molecule inhibitors including VLA-4 antagonists; (f) cathepsins; (g) MAP kinase inhibitors; (h) glucose-6 phosphate dehydrogenase inhibitors; (i) kinin-B1- and B2-receptor antagonists; j) anti-gout agents, e.g., colchicine; (k) xanthine oxidase inhibitors, e.g., allopurinol; (l) uricosuric agents, e.g., probenecid, sulfinpyrazone, and benzbromarone; (m) growth hormone secretagogues; (n) transforming growth factor (TGFβ); (o) platelet-derived growth factor (PDGF); (p) fibroblast growth factor, e.g., basic fibroblast growth factor (bFGF); (q) granulocyte macrophage colony stimulating factor (GM-CSF); (r) capsaicin cream; (s) Tachykinin NK1 and NK3 receptor antagonists such as NKP-608C; SB-233412 (talnetant); and D-4418; and (t) elastase inhibitors such as UT-77 and ZD-0892.

A compound of Formula (I) of the present invention can be administered in combination with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11).

A compound of Formula (I) of the present invention can be administered in combination with anticancer agents such as endostatin and angiostatin or cytotoxic drugs such as adriamycin, daunomycin, cis-platinum, etoposide, taxol, taxotere and farnesyl transferase inhibitors, VEGF inhibitors, COX-2 inhibitors and antimetabolites such as methotrexate antineoplastic agents, especially antimitotic drugs including the vinca alkaloids such as vinblastine and vincristine.

A compound of Formula (I) of the present invention can be administered in combination with antiviral agents such as Viracept, AZT, aciclovir and famciclovir, and antisepsis compounds such as Valant.

A compound of Formula (I) of the present invention can be administered in combination with cardiovascular agents such as calcium channel blockers, lipid lowering agents such as stating, fibrates, beta-blockers, ACE inhibitors, Angiotensin-2 receptor antagonists and platelet aggregation inhibitors.

A compound of Formula (I) of the present invention can be administered in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

A compound of Formula (I) of the present invention can be administered in combination with osteoporosis agents such as roloxifene, droloxifene, lasofoxifene or fosomax and immunosuppressant agents such as FK-506, rapamycin, cyclosporine, azathioprine, and methotrexate.

In certain embodiments, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax I1-15).

The present invention still further relates to the combination of a compound of the invention, or a pharmaceutically acceptable salt thereof, with a modulator of chemokine receptor function such as an antagonist of CCR1, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX3CR1 for the C—X3-C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY×1005.

The present invention further relates to the combination of a compound of the invention, or a pharmaceutically acceptable salt thereof, and a receptor antagonist for leukotrienes (LT) B4, LTC4, LTD4, and LTE4. Selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs, for example rosiglitazone.

The present invention further relates to the combination of a compound of the invention, or a pharmaceutically acceptable salt thereof with gabapentin, lidoderm, pregablin and equivalents and pharmaceutically active isomer(s) and metabolite(s) thereof.

The present invention further relates to the combination of a compound of the invention, or a pharmaceutically acceptable salt thereof with celecoxib, etoricoxib, lumiracoxib, rofecoxib, valdecoxib, diclofenac, loxoprofen, naproxen, paracetamol and equivalents and pharmaceutically active isomer(s) and metabolite(s) thereof.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, gabapentin, pregabalin, phenyloin, sodium valproate, amitryptiline or other anti-depressant agent-s, paracetamol, CB 1 agonist, muscarinic agonist, TRPV-1 antagonist, mGluR5 agonist or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B1- or B2-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGF3); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK1 or NK3 receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), or (xxvi) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include: (i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin); (ii) a cytostatic agent such as an antioestrogen (for example tamoxifen, toremifene, raloxifene, droloxifene or iodoxyfene), an oestrogen receptor down regulator (for example fulvestrant), an anti-androgen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride; (iii) an agent which inhibits cancer cell invasion (for example a metalloproteinase inhibitor like marimastat or an inhibitor of urokinase plasminogen activator receptor function); (iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI-1033)), an inhibitor of the platelet-derived growth factor family, or an inhibitor of the hepatocyte growth factor family; (v) an antiangiogenic agent such as one which inhibits the effects of vascular endothelial growth factor (for example the anti-vascular endothelial cell growth factor antibody bevacizumab, linomide, an inhibitor of integrin αvβ3 function or an angiostatin); (vi) a vascular damaging agent such as combretastatin A4; (vii) an agent used in antisense therapy, for example one directed to one of the targets listed above, such as ISIS 2503, an anti-ras antisense; (viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to antagonize P2X7 activity, usually between about one hour and one week. In-vitro treatment can be carried out using cultivated cells from a biopsy sample or cell line.

The host or subject can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, suitable models or model systems have been developed, for example cell culture models and models of transgenic animals. For the determination of certain stages in the signal transduction cascade, interacting compounds can be utilized in order to modulate the signal. The compounds according to the invention can also be used as reagents for testing P2X7-dependent signal transduction pathways in animals and/or cell culture models or in the clinical diseases mentioned in this application.

The use according to the previous paragraphs of the specification may be either performed in-vitro or in-vivo models. The modulation can be monitored by the techniques described in the course of the present specification. In certain embodiments, the in-vitro use is preferably applied to samples of humans suffering from P2X7-related disorders. Testing of several specific compounds and/or derivatives thereof makes the selection of that active ingredient possible that is best suited for the treatment of the human subject. The in-vivo dose rate of the chosen derivative is advantageously pre-adjusted to the P2X7 susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the antagonism of P2X7 activity if expedient.

The invention also relates to the use of compounds according to formula (I) and/or physiologically acceptable salts thereof for the prophylactic or therapeutic treatment and/or monitoring of diseases that are caused, mediated and/or propagated by P2X7 activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by P2X7 activity. In certain embodiments, the invention provides the use of a compound according to formula I or physiologically acceptable salts thereof, for the production of a medicament for the prophylactic or therapeutic treatment of a P2X7-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The methods of the invention can also be used to reducing the likelihood of developing a disorder or even prevent the initiation of disorders associated with P2X7 activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously passed disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with P2X7 activity, in such a way that a pathogenic modification of their overall condition or of the condition of particular regions of the organism could establish at least temporarily.

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches.

The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention can also be utilized as commercial research reagents for various medical research and diagnostic uses. Such uses can include but are not limited to: use as a calibration standard for quantifying the activities of candidate P2X7 antagonists in a variety of functional assays; use as blocking reagents in random compound screening, i.e. in looking for new families of P2X7 receptor ligands, the compounds can be used to block recovery of the presently claimed P2X7 compounds; use in the co-crystallization with P2X7 receptor, i.e. the compounds of the present invention will allow formation of crystals of the compound bound to P2X7, enabling the determination of receptor/compound structure by x-ray crystallography; other research and diagnostic applications, etc.; use in assays as probes for determining the expression of P2X7 on the surface of cells; and developing assays for detecting compounds which bind to the same site as the P2X7 binding ligands.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Antagonism of P2X7 activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples below correspond to compound numbers set forth supra.

$^1$H NMR was recorded on a Bruker 400 MHz spectrometer, using residual signal of deuterated solvent as internal reference. Chemical shifts (δ) are reported in ppm relative to the residual solvent signal (δ=2.49 ppm for 1H NMR in DMSO-d6). 1H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

LCMS-Analysis was performed under known standard conditions

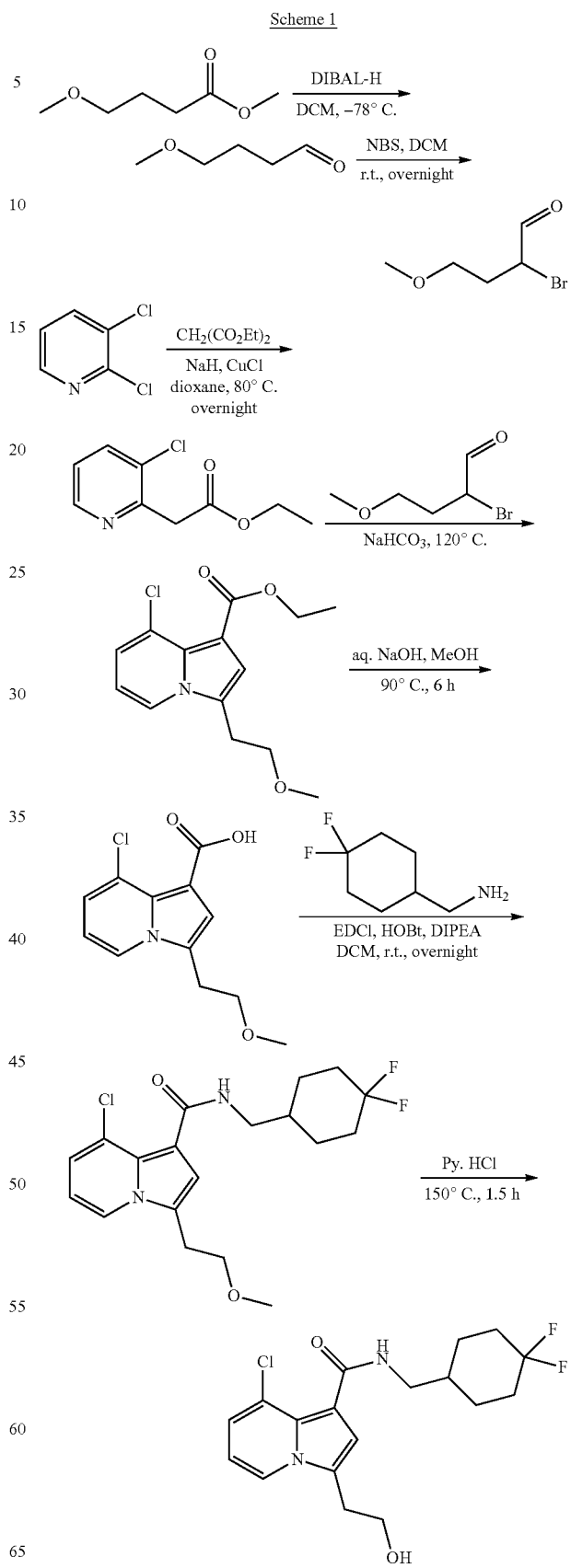

Scheme 1

Intermediate 1

8-chloro-3-(2-methoxyethyl)indolizine-1-carboxylic acid

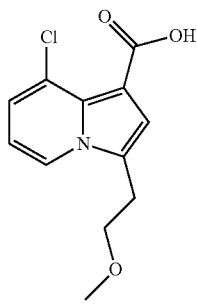 [SMILES: COCCc1cc(C(=O)O)c2c(Cl)cccn12]

Step 1. 4-Methoxybutanal

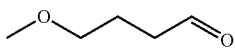

To a solution of methyl 4-methoxybutanoate (3.43 g, 26 mmol) in DCM (26 mL) was added DIBAL-H (33 mL, 33 mmol, 1 M in toluene) at −78° C. After stirring at −78° C. for 50 mins, the reaction was quenched with MeOH (10 mL) and then brine (20 mL). The separated organic layer was dried over $Na_2SO_4$, concentrated in vacuo to give 4-methoxybutanal (2.25 g, 85%) as colorless liquid, which was used in the next reaction without further purification.

Step 2. 2-Bromo-4-methoxybutanal

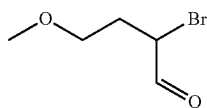

To a solution of 4-methoxybutanal (2.5 g, 24.5 mmol) and D,L-proline (0.550 g, 4.9 mmol) in DCM (30 mL) was added NBS (3.93 g, 22 mmol) portionwise at 0° C. After being stirred at room temperature overnight, the mixture was quenched with water and extracted with DCM (100 mL). The separated organic layer was washed with aqueous $Na_2S_2O_3$, brine, dried over MgSO4, filtered and concentrated in vacuo. The residue was purified by column chromatography on silica gel (petroleum ether: EtOAc=30:1) to give 2-bromo-4-methoxybutanal (1.1 g, 24%) as brown liquid.

Step 3. Ethyl 2-(3-chloropyridin-2-yl)acetate

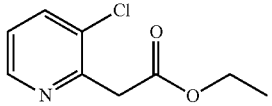

To a suspension of NaH (0.400 g, 10 mmol, 60% in mineral oil) in dioxane (10 mL) was added diethyl malonate (3.2 g, 20 mmol) at 60° C. After the mixture was stirred at 60° C. for 0.5 h, CuCl (990 mg, 10 mmol) was added, followed by addition of a solution of 2,3-dichloropyridine (1.48 g, 10 mmol) in dioxane (15 mL) dropwise at 80° C. After being stirred at 80° C. overnight, the reaction was quenched with 1 N aqueous HCl, and extracted with EtOAc (50 mL). The separated organic phase was dried, filtered and concentrated in vacuo. The residue was purified by column chromatography on silica gel (petroleum ether: EtOAc=10:1) to give ethyl 2-(3-chloropyridin-2-yl)acetate (0.88 g, 44%) as yellow liquid.

Step 4. Ethyl 8-chloro-3-(2-methoxyethyl)indolizine-1-carboxylate

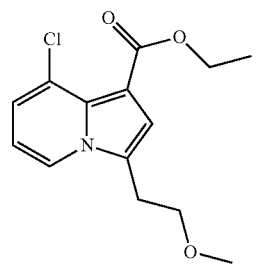 [SMILES: CCOC(=O)c1cc(CCOC)n2cccc(Cl)c12]

A mixture of ethyl 2-(3-chloropyridin-2-yl)acetate (2.19 g, 11 mmol), 2-bromo-4-methoxybutanal (2.7 g, 15 mmol) and $NaHCO_3$ (4.62 g, 55 mmol) was heated at 120° C. overnight. After cooled to room temperature, the reaction mixture was diluted with DCM (100 mL) and filtered through a celite pad. The filtrate was concentrated in vacuo and the residue was purified by column chromatography on silica gel (petroleum ether: EtOAc=30:1) to give ethyl 8-chloro-3-(2-methoxyethyl)indolizine-1-carboxylate (1.7 g, 65%) as brown liquid.

Step 5. 8-chloro-3-(2-methoxyethyl)indolizine-1-carboxylic acid

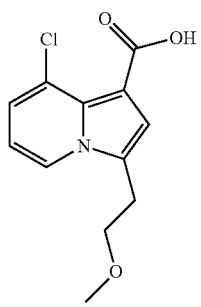 [SMILES: COCCc1cc(C(=O)O)c2c(Cl)cccn12]

To a solution of ethyl 8-chloro-3-(2-methoxyethyl)indolizine-1-carboxylate (0.562 g, 2.0 mmol) in MeOH (5.0 mL) was added aqueous NaOH (5.0 mL, 1 N) at room temperature. The reaction mixture was stirred at 80° C. for 4 h, and then neutralized with saturated $NH_4Cl$ solution, and extracted with EtOAc (8×10 mL). The combined organic layers were dried over $Na_2SO_4$, concentrated in vacuo to give 8-chloro-3-(2-methoxyethyl)indolizine-1-carboxylic acid (0.300 g, 75%) as a pink solid, which was used in the next reaction without further purification.

Example 1

8-chloro-N-((4,4-difluorocyclohexyl)methyl)-3-(2-methoxyethyl) indolizine-1-carboxamide (37)

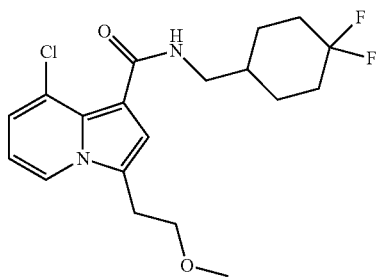 [SMILES: COCCc1cc(C(=O)NCC2CCC(F)(F)CC2)c2c(Cl)cccn12]

A mixture of 8-chloro-3-(2-methoxyethyl)indolizine-1-carboxylic acid (0.100 g, 0.4 mmol), (4,4-difluorocyclohexyl)methanamine (0.060 g, 0.4 mmol), HOBt (0.108 g, 0.8 mmol), EDCI (0.152 g, 0.8 mmol) and Et$_3$N (0.121 g, 1.2 mmol) in DMF (3.0 mL) was stirred at room temperature overnight, and then diluted with EtOAc (20 mL). The organic layer was washed with brine (10 mL), dried over MgSO$_4$, filtered and concentrated in vacuo. The residue was purified by prep-TLC (petroleum ether: EtOAc=10:1) to give 8-chloro-N-((4,4-difluorocyclohexyl)methyl)-3-(2-methoxyethyl)indolizine-1-carboxamide (0.100 g, 65.1%) as a white solid.
$^1$H NMR (500 MHz, DMSO-d$_6$) δ 8.18 (d, J=7.0 Hz, 1 H), 8.11 (d, J=6.0 Hz, 1 H), 6.95 (d, J=7.0 Hz, 1 H), 6.78 (s, 1 H), 6.67 (t, J=7.0 Hz, 1 H), 3.66 (t, J=6.5 Hz, 2 H), 3.27 (s, 3 H), 3.15-3.10 (m, 4 H), 2.03-2.00 (m, 2 H), 1.83-1.81 (m, 3 H), 1.74-1.71 (m, 2 H), 1.25-1.22 (m, 2 H) ppm; [M+H]$^+$ 385.1.

Example 2

8-chloro-N-((4,4-difluorocyclohexyl)methyl)-3-(2-hydroxyethyl)indolizine-1-carboxamide (51)

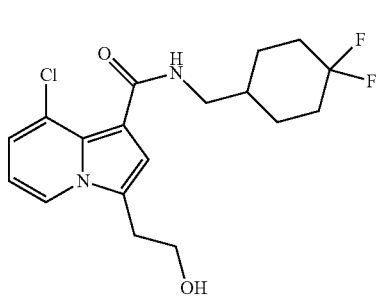 [SMILES: O=C(NCC1CCC(F)(F)CC1)c1cc(CCO)n2cccc(Cl)c12]

A mixture of 8-chloro-N-((4,4-difluorocyclohexyl)methyl)-3-(2-methoxyethyl)indolizine-1-carboxamide (0.076 g, 0.2 mmol) and pyridine hydrochloric acid (0.50 g, 4.2 mmol) was stirred in a sealed tube at 150° C. for 1.5 h. After cooled to room temperature, the reaction mixture was diluted with EtOAc (20 mL) and washed with water (3×20 mL), dried over Na$_2$SO$_4$, filtered and concentrated in vacuo.

The residue was purified by column chromatography on silica gel (petroleum ether: EtOAc=1:1) to give 8-chloro-N-((4,4-difluorocyclohexyl)methyl)-3-(2-hydroxyethyl)indolizine-1-carboxamide (0.030 g, 40.5%) as a white solid.
$^1$H NMR (500 MHz, DMSO-d$_6$) δ 8.17 (d, J=7.5 Hz, 1 H), 8.05 (t, J=6.0 Hz, 1 H), 6.93 (d, J=6.5 Hz, 1 H), 6.78 (s, 1 H), 6.65 (t, J=7.5 Hz, 1 H), 4.79 (t, J=10.0 Hz, 1 H), 3.74 (dd, J=6.0 Hz, 2 H), 3.13 (t, J=6.5 Hz, 2 H), 3.00 (t, J=6.5 Hz, 2 H), 2.04-1.99 (m, 2 H), 1.83-1.67 (m, 4 H), 1.26-1.17 (m, 2 H) ppm; m/z: 371.1 [M+H]$^+$ Example 3

8-chloro-N-(cyclohexylmethyl)-3-(2-methoxyethyl)-indolizine-1-carboxamide (8)

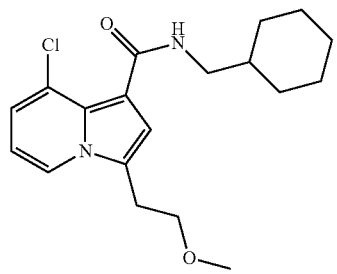 [SMILES: COCCc1cc(C(=O)NCC2CCCCC2)c2c(Cl)cccn12]

The title compound was synthesized according to the procedure described in example 1 using 8-Chloro-3-(2-methoxy-ethyl)-indolizine-1-carboxylic acid and cyclohexylmethanamine as the starting materials.
$^1$H NMR (500 MHz, CDCl$_3$): δ 7.83 (d, J=5.0 Hz, 1 H), 6.88-6.86 (m, 2 H), 6.54 (t, J=7.5 Hz, 1 H), 5.93 (s, 1 H), 3.72 (t, J=7.0 Hz, 2 H), 3.36 (s, 3H), 3.33-3.30 (m, 2 H), 3.07 (t, J=6.0 Hz, 2 H), 1.81-1.55 (m, 6 H), 1.27-1.02 (m, 5 H) ppm; m/z: 349 [M+H]$^+$ Example 4

8-chloro-N-(cyclohexylmethyl)-3-(2-hydroxyethyl) indolizine-1-carboxamide (15)

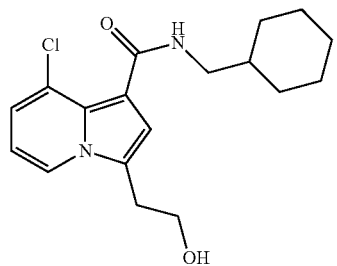 [SMILES: O=C(NCC1CCCCC1)c1cc(CCO)n2cccc(Cl)c12]

The title compound was synthesized (0.130 g, 20%) according to the procedure described in example 1 using 8-chloro-3-(2-hydroxyethyl)indolizine-1-carboxylic acid (0.480 g, 2.0 mmol), EDCI (0.800 g, 0.42 mmol), HOBt (0.425 g, 3.1 mmol), Et$_3$N (0.525 g, 5.2 mmol) and cyclohexylmethanamine (0.226 g, 2.0 mmol) as the starting materials.
$^1$H NMR (500 MHz, CDCl$_3$): δ 7.83 (d, J=5.5 Hz, 1 H), 6.90-6.87 (m, 2 H), 6.55 (t, J=7.5 Hz, 1 H), 5.95 (s, 1 H), 3.97 (t, J=6.5 Hz, 2 H), 3.33-3.30 (m, 2 H), 3.09-3.07 (t, J=6.0 Hz, 2 H), 1.81-1.55 (m, 6 H), 1.27-1.02 (m, 5 H) ppm; m/z: 335 [M+H]+

Example 5

8-chloro-N-((1-hydroxy-3,3-dimethylcyclohexyl)methyl)-3-(2-methoxyethyl) indolizine-1-carboxamide (10)

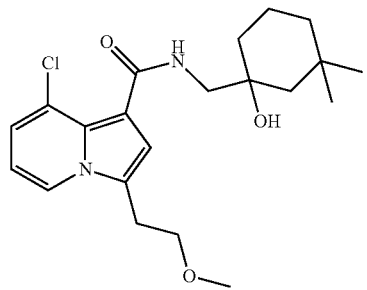 [SMILES: COCCc1cc(C(=O)NCC2(O)CCCC(C)(C)C2)c2c(Cl)cccn12]

The title compound was synthesized (173 mg, 74%) according to the procedure described in example 1 using 8-Chloro-3-(2-methoxy-ethyl)-indolizine-1-carboxylic acid (150.00 mg; 0.59 mmol; 1.00 eq.), 1-Aminomethyl-3,3-dimethyl-cyclohexanol (106.93 mg; 0.68 mmol; 1.15 eq.), (3-Dimethylamino-propyl)-ethyl-carbodiimide hydrochloride (147.36 mg; 0.77 mmol; 1.30 eq.)(EDCI), Benzotriazol-1-ol (103.87 mg; 0.77 mmol; 1.30 eq.) (HOBt) and Ethyl-diisopropyl-amine (0.29 ml; 1.77 mmol; 3.00 eq.) as the starting materials.
$^1$H NMR (400 MHz, DMSO-d6) δ 8.19 (d, J=7.0 Hz, 1H), 7.74 (t, J=6.0 Hz, 1H), 6.97 (d, J=7.1 Hz, 1H), 6.83 (s, 1H), 6.68 (t, J=7.1 Hz, 1H), 4.19 (s, 1H), 3.68 (t, J=6.4 Hz, 2H), 3.28 (s, 3H), 3.22-3.06 (m, 4H), 1.82-1.15 (m, 8H), 1.05 (s, 3H), 0.85 (s, 3H). m/z: 393.0 [M+H]+

Example 6

8-chloro-3-(2-methoxyethyl)-N-(spiro[2.5]octan-5-ylmethyl)indolizine-1-carboxamide (2)

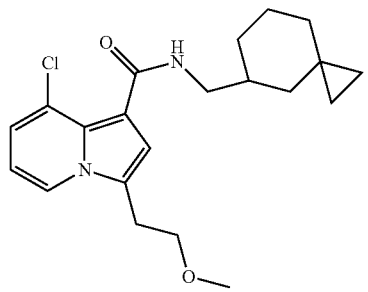 [SMILES: COCCc1cc(C(=O)NCC2CCCC3(CC3)C2)c2c(Cl)cccn12]

The title compound was synthesized (161 mg, 73%) according to the procedure described in example 1 using 8-Chloro-3-(2-methoxy-ethyl)-indolizine-1-carboxylic acid (150.00 mg; 0.59 mmol; 1.00 eq.), C-Spiro[2.5]oct-5-yl-methylamine hydrochloride (119.47 mg; 0.68 mmol; 1.15 eq.), (3-Dimethylamino-propyl)-ethyl-carbodiimide hydrochloride (147.36 mg; 0.77 mmol; 1.30 eq.)(EDCI), Benzotriazol-1-ol (103.87 mg; 0.77 mmol; 1.30 eq.) (HOBt) and Ethyl-diisopropyl-amine (0.29 ml; 1.77 mmol; 3.00 eq.) as the starting materials.
$^1$H NMR (400 MHz, DMSO-d6) δ 8.17 (d, J=7.0 Hz, 1H), 7.95 (t, J=5.9 Hz, 1H), 6.93 (d, J=7.1 Hz, 1H), 6.76 (s, 1H), 6.65 (t, J=7.1 Hz, 1H), 3.66 (t, J=6.4 Hz, 2H), 3.30 (d, J=16.4 Hz, 3H), 3.07 (dp, J=31.8, 7.0, 6.4 Hz, 4H), 1.90-1.52 (m, 4H), 1.36 (td, J=12.1, 5.1 Hz, 2H), 1.10-0.78 (m, 4H), 0.36-0.04 (m, 4H). m/z: 375.0 [M+H]+

Example 7

8-chloro-N-((5-hydroxyspiro[2.5]octan-5-yl)methyl)-3-(2-methoxyethyl) indolizine-1-carboxamide (29)

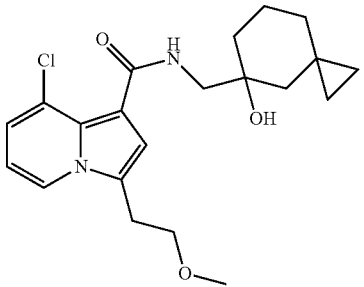 [SMILES: COCCc1cc(C(=O)NCC2(O)CCCC3(CC3)C2)c2c(Cl)cccn12]

The title compound was synthesized (176 mg, 73%) according to the procedure described in example 1 using 8-Chloro-3-(2-methoxy-ethyl)-indolizine-1-carboxylic acid (150.00 mg; 0.59 mmol; 1.00 eq.), 5-Aminomethyl-spiro[2.5]octan-5-ol hydrochloride (130.35 mg; 0.68 mmol; 1.15 eq.), (3-Dimethylamino-propyl)-ethyl-carbodiimide hydrochloride (147.36 mg; 0.77 mmol; 1.30 eq.)(EDCI), Benzotriazol-1-ol (103.87 mg; 0.77 mmol; 1.30 eq.) (HOBt) and Ethyl-diisopropyl-amine (0.29 ml; 1.77 mmol; 3.00 eq.) as the starting materials.
$^1$H NMR (400 MHz, Chloroform-d) δ 7.87 (d, J=7.1 Hz, 1H), 6.92 (d, J=7.1 Hz, 2H), 6.58 (t, J=7.1 Hz, 1H), 3.74 (t, J=6.5 Hz, 2H), 3.59 (d, J=5.8 Hz, 2H), 3.39 (s, 3H), 3.10 (t, J=6.5 Hz, 2H), 1.66 (tt, J=11.6, 5.8 Hz, 5H), 1.39 (t, J=12.3 Hz, 2H), 1.20 (d, J=13.6 Hz, 1H), 0.45-0.23 (m, 4H).

Example 8

Preparation of 8-chloro-N-((4,4-difluoro-1-hydroxycyclohexyl)methyl)-3-(2-methoxyethyl)indolizine-1-carboxamide (53)

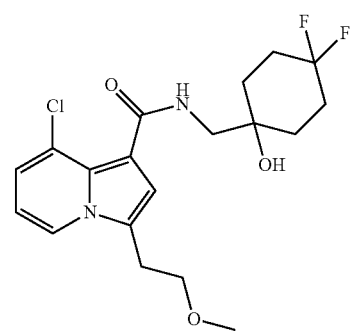 [SMILES: COCCc1cc(C(=O)NCC2(O)CCC(F)(F)CC2)c2c(Cl)cccn12]

The title compound was synthesized (0.070 g, 88%) according to the procedure described in example 1 using 8-chloro-3-(2-methoxyethyl) indolizine-1-carboxylic acid (0.050 g, 0.20 mmol), 1-(aminomethyl)-4,4-difluorocyclohexanol (0.060 g, 0.30 mmol), HOBt (0.041 g, 0.30 mmol), EDCI (0.047 g, 0.30 mmol) and DIPEA (0.077 g, 0.60 mmol) as the starting materials.

¹H NMR (500 MHz, DMSO-d₆) δ 8.20 (d, J=7.0 Hz, 1 H), 7.95 (d, J=6.0 Hz, 1 H), 6.97 (d, J=7.5 Hz, 1 H), 6.83 (s, 1 H), 6.68 (t, J=7.0 Hz, 1 H), 4.74 (s, 1 H), 3.67 (t, J=6.0 Hz, 2 H), 3.29-3.27 (m, 5 H), 3.12 (t, J=6.0 Hz, 2 H), 2.09-1.96 (m, 2 H), 1.89-1.85 (m, 2 H), 1.67-1.62 (m, 4 H) ppm; m/z: 401 [M+H]⁺

Example 9

Preparation of 8-chloro-N-((3,3-difluorocyclohexyl)methyl)-3-(2-methoxyethyl)indolizine-1-carboxamide (31)

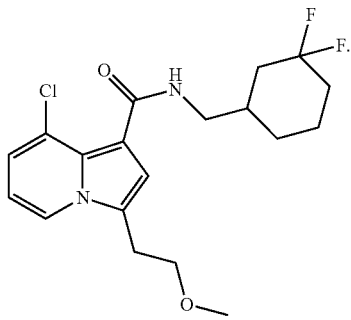 [SMILES: COCCc1cc(C(=O)NCC2CCCC(F)(F)C2)c2c(Cl)cccn12]

The title compound was synthesized (0.105 g, 70%) according to the procedure described in example 1 using 8-chloro-3-(2-methoxyethyl)indolizine-1-carboxylic acid (0.100 g, 0.4 mmol), (3,3-difluorocyclohexyl)methanamine (0.0596 g, 0.4 mmol), EDCI (0.0913 g, 0.5 mmol), HOBt (0.069 g, 0.5 mmol), and Et₃N (0.121 g, 1.2 mmol) as the starting materials.

¹H NMR (500 MHz, DMSO-d₆) δ 8.18 (d, J=7.0 Hz, 1 H), 8.11-8.09 (t, J=5.2 Hz, 1 H), 6.95 (d, J=7.0 Hz, 1 H), 6.79 (s, 1 H), 6.68-6.66 (t, J=7.0 Hz, 1 H), 3.68-3.65 (t, J=6.5 Hz, 2 H), 3.28 (s, 1 H), 3.21-3.18 (m, 1 H), 3.13-3.11 (t, J=6.2 Hz, 3 H), 2.13 (m, 1 H), 1.99-1.98 (m, 1 H), 1.81-1.63 (m, 4 H), 1.56-1.36 (m, 2 H), 1.08-1.00 (m, 1H) ppm; m/z: 385.1 [M+H]⁺

Example 10

Preparation of 8-chloro-N-((3,3-difluorocyclohexyl)methyl)-3-(2-hydroxy ethyl)indolizine-1-carboxamide (45)

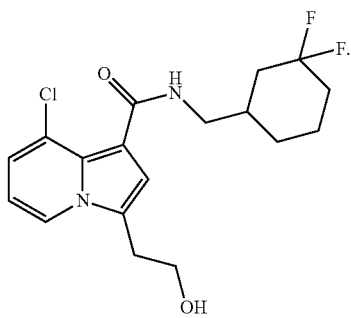 [SMILES: O=C(NCC1CCCC(F)(F)C1)c1cc(CCO)n2cccc(Cl)c12]

To a mixture of 8-chloro-N-((3,3-difluorocyclohexyl)methyl)-3-(2-hydroxyethyl)indolizine-1-carboxamide (0.070 g, 0.18 mmol) in DCM (5 mL) at −78° C. was added a saturated solution of 15-crown-5 and sodium iodide in DCM (3 mL), followed by the addition of boron tribromide (1.56 mL, 0.3 M in DCM) drop wise. The system was stirred at this temperature for 3.5 h and then quenched with saturated sodium bicarbonate solution and extracted with EtOAc (20 mL×3). The combined organic layers were dried over Na₂SO₄, filtered and concentrated. The residue was purified by Prep-HPLC to afford 8-chloro-N-((3,3-difluorocyclohexyl)methyl)-3-(2-hydroxyethyl)indolizine-1-carboxamide (0.020 g, 26%) as a white solid.

¹HNMR (500 MHz, DMSO-d₆): δ 8.18 (d, J=7.5 Hz, 1 H), 8.08 (t, J=6.0 Hz, 1H), 6.94 (d, J=7.0 Hz, 1 H), 6.79 (s, 1 H), 6.67 (t, J=7.0 Hz, 1 H), 4.81 (t, J=5.0 Hz, 1 H), 3.76-3.73 (m, 2 H), 3.22-3.17 (m, 1 H), 3.14-3.09 (m, 1 H), 3.02 (t, J=6.5 Hz, 2 H), 2.13-2.10 (m, 1 H), 1.99-1.98 (m, 1 H), 1.77-1.63 (m, 4 H), 1.57-1.47 (m, 2 H), 1.08-1.00 (m, 1 H) ppm; m/z: 371.1 [M+H]⁺

Example 11

8-Chloro-3-(2-methoxy-ethyl)-indolizine-1-carboxylic acid (3,3-difluoro-1-hydroxycyclohexylmethyl)-amide (62)

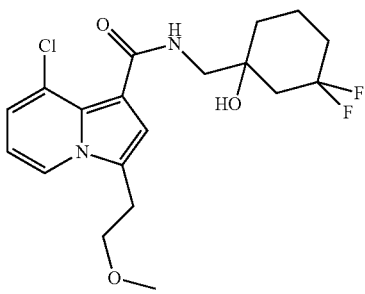 [SMILES: COCCc1cc(C(=O)NCC2(O)CCCC(F)(F)C2)c2c(Cl)cccn12]

The title compound was synthesized (250 mg, 62%) according to the procedure described in example 1 using 8-Chloro-3-(2-methoxy-ethyl)-indolizine-1-carboxylic acid (0.50 g, 0.74 mmol, 1.00 eq), 1-Aminomethyl-3,3-difluoro-cyclohexanol hydrochloride (0.22 g, 1.11 mmol, 1.50 eq), Et₃N (0.31 mL, 2.22 mmol, 3.00 eq), (3-Dimethylaminopropyl)-ethyl-carbodiimide hydrochloride (0.29 g, 1.48 mmol, 2.00 eq) and Benzotriazol-1-ol (0.18 g, 1.11 mmol, 1.50 eq) as the starting materials.

¹H NMR (400 MHz, DMSO-d₆) δ8.19 (d, J=6.9 Hz, 1H), 7.90 (t, J=6.1 Hz, 1H), 6.96 (d, J=6.9 Hz, 1H), 6.84 (s, 1H), 6.67 (t, J=7.1 Hz, 1H), 4.68 (s, 1H), 3.66 (t, J=6.4 Hz, 2H), 3.32 (s, 1H), 3.26 (s, 3H), 3.21-3.16 (m, 1H), 3.11 (t, J=6.4 Hz, 1H), 2.00-1.92 (m, 3H), 1.73 (t, J=8.2 Hz, 2H), 1.56-1.48 (m, 3H). m/z: 401.20 [M+H]⁺

Example 12

8-Chloro-3-(2-methoxy-ethyl)-indolizine-1-carboxylic acid ((S)-3,3-difluoro-1-hydroxy-cyclohexylmethyl)-amide (63)

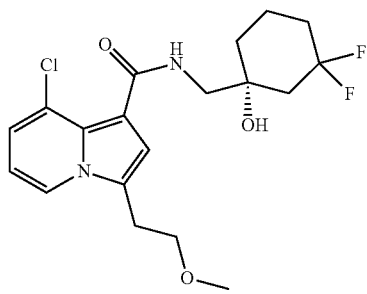 [SMILES: COCCc1cc(C(=O)NC[C@@]2(O)CCCC(F)(F)C2)c2c(Cl)cccn12]

A racemic mixture of 8-Chloro-3-(2-methoxy-ethyl)-indolizine-1-carboxylic acid (3,3-difluoro-1-hydroxycyclohexylmethyl)-amide (35.00 mg, 0.09 mmol, 1.00 eq) was separated by chiralcel HPLC to provide 8-Chloro-3-(2-methoxy-ethyl)-indolizine-1-carboxylic acid ((S)-3,3-difluoro-1-hydroxy-cyclohexylmethyl)-amide (57.4 mg, 53%) as a white powder.
Mobile Phase: 0.1% DEA IN HEXANE:IPA:80:20
Column: CHIRALCEL OD-H (250×4.6) mm, 5 μm
Flow rate: 1.0 mL\min
$^1$H NMR (400 MHz, DMSO-$d_6$) δ8.19 (d, J=6.9 Hz, 1H), 7.90 (t, J=6.1 Hz, 1H), 6.96 (d, J=6.9 Hz, 1H), 6.84 (s, 1H), 6.67 (t, J=7.0 Hz, 1H), 4.68 (s, 1H), 3.66 (t, J=6.4 Hz, 2H), 3.32 (s, 1H), 3.26 (s, 3H), 3.21-3.16 (m, 1H), 3.11 (t, J=6.4 Hz, 1H), 2.00-1.92 (m, 3H), 1.73 (t, J=5.2 Hz, 2H), 1.56-1.48 (m, 3H). m/z: 401.20 [M+H]$^+$ Example 13

8-Chloro-3-(2-methoxy-ethyl)-indolizine-1-carboxylic acid ((S)-3,3-difluoro-1-hydroxy-cyclohexylmethyl)-amide (64)

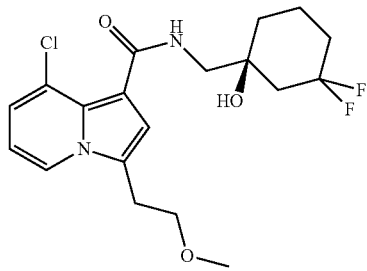 [SMILES: COCCc1cc(C(=O)NC[C@]2(O)CCCC(F)(F)C2)c2c(Cl)cccn12]

A racemic mixture of 8-Chloro-3-(2-methoxy-ethyl)-indolizine-1-carboxylic acid (3,3-difluoro-1-hydroxycyclohexylmethyl)-amide (35.00 mg, 0.09 mmol, 1.00 eq) was separated by chiralcel HPLC to provide 8-Chloro-3-(2-methoxy-ethyl)-indolizine-1-carboxylic acid ((S)-3,3-difluoro-1-hydroxy-cyclohexylmethyl)-amide (57 mg, 53%) as a white powder.
Mobile Phase: 0.1% DEA IN HEXANE:IPA:80:20
Column: CHIRALCEL OD-H (250×4.6) mm, 5 μm
Flow rate: 1.0 mL\min
$^1$H NMR (400 MHz, DMSO-$d_6$) 8.19 (d, J=6.9 Hz, 1H), 7.90 (t, J=6.1 Hz, 1H), 6.96 (d, J=6.9 Hz, 1H), 6.84 (s, 1H), 6.67 (t, J=7.0 Hz, 1H), 4.68 (s, 1H), 3.66 (t, J=6.4 Hz, 2H), 3.32 (s, 1H), 3.26 (s, 3H), 3.21-3.16 (m, 1H), 3.11 (t, J=6.4 Hz, 1H), 2.00-1.92 (m, 3H), 1.73 (t, J=5.2 Hz, 2H), 1.56-1.48 (m, 3H). m/z: 401.20 [M+H]$^+$ Example 14

8-Chloro-3-(2-hydroxy-ethyl)-indolizine-1-carboxylic acid (3,3-difluoro-1-hydroxy-cyclohexylmethyl)-amide (68)

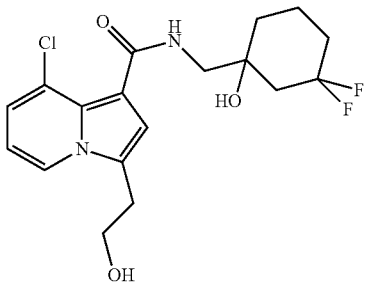 [SMILES: O=C(NCC1(O)CCCC(F)(F)C1)c1cc(CCO)n2cccc(Cl)c12]

The title compound was synthesized (6 mg, 2%) according to the procedure described in example 2 using 8-Chloro-3-(2-methoxy-ethyl)-indolizine-1-carboxylic acid, (3,3-difluoro-1-hydroxy-cyclohexyl methyl)-amide (0.40 g, 0.99 mmol, 1.00 eq) and Pyridine hydrochloride (2.57 g, 21.79 mmol, 22.00 eq) as the starting materials.
$^1$H NMR (400 MHz, DMSO-$d_6$) δ 8.21 (d, J=6.2 Hz, 1H), 7.89 (s, 1H), 6.97 (d, J=7.0 Hz, 1H), 6.86 (s, H), 6.69 (d, J=7.0 Hz, 1H), 4.82 (s, 1H), 4.71 (s, 1H), 3.76 (s, 2H), 3.28-3.27 (m, 1H), 3.02-3.00 (m, 2H), 2.00-1.93 (m, 3H), 1.75-1.72 (m, 2H), 1.58-1.55 (m, 3H). m/z: 387.0 [M+H]$^+$ Example 15

8-chloro-N-((4,4-difluoro-3-methylcyclohexyl)methyl)-3-(2-methoxyethyl) indolizine-1-carboxamide (11)

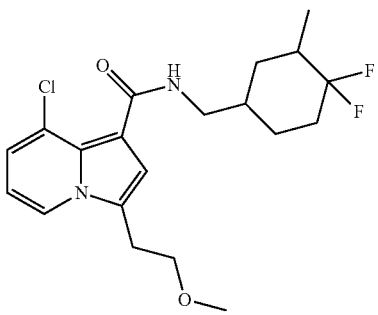 [SMILES: COCCc1cc(C(=O)NCC2CCC(F)(F)C(C)C2)c2c(Cl)cccn12]

The title compound was synthesized (90 mg, 57%) according to the procedure described in example 1 using 8-chloro-3-(2-methoxyethyl) indolizine-1-carboxylic acid (0.100 g, 0.39 mmol), (4,4-difluoro-3-methylcyclohexyl) methanamine (0.064 g, 0.59 mmol), HOBt (0.080 g, 0.59 mmol), EDCI (0.113 g, 0.59 mmol) and DIEA (0.153 g, 1.18 mmol) as the starting materials.

¹H NMR (500 MHz, CDCl₃) δ7.88 (d, J=7.0 Hz, 1 H), 6.92 (d, J=6.0 Hz, 2 H), 6.58 (d, J=7.5 Hz, 1 H), 6.02-5.98 (m, 1 H), 3.75 (t, J=7.0 Hz, 2 H), 3.46-3.42 (m, 1 H), 3.39 (s, 3 H), 3.38-3.36 (m, 1 H), 3.10 (t, J=6.5 Hz, 2 H), 2.24-2.16 (m, 1 H), 2.00-1.51 (m, 6 H), 1.37-1.14 (m, 1 H), 1.09-1.06 (m, 3 H) ppm; m/z: 399.0 [M+H]⁺

Example 16

8-chloro-N-((4,4-difluoro-3-methylcyclohexyl)methyl)-3-(2-hydroxyethyl) indolizine-1-carboxamide (32)

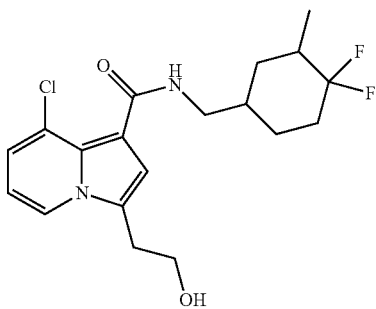 [SMILES: CC1CC(CNC(=O)c2cc(CCO)n3cccc(Cl)c23)CCC1(F)F]

The title compound was synthesized (16 mg, 33%) according to the procedure described in example 10 using 8-chloro-N-((4,4-difluoro-3-methylcyclohexyl)methyl)-3-(2-methoxyethyl) indolizine-1-carboxamide (0.050 g, 0.16 mmol), 15-crown-5 and sodium iodide (0.38 mmol, 0.3 M), boron tribromide (1M, 0.63 mL) as the starting materials.

1H NMR (500 MHz, DMSO-d₆) δ8.17 (d, J=7.5 Hz, 1 H), 8.07-8.03 (m, 1 H), 6.94 (d, J=7.0 Hz, 1 H), 6.78 (s, 1 H), 6.66 (t, J=7.0 Hz, 1 H), 4.82 (t, J=5.0 Hz, 1 H), 3.74 (q, J=6.0 Hz, 2 H), 3.20 (brs, 1 H), 3.10 (t, J=6.0 Hz, 1 H), 3.01 (t, J=6.5 Hz, 2 H), 2.21-2.03 (m, 1 H), 1.92-1.85 (m, 2 H), 1.83-1.42 (m, 4 H), 1.24-0.86 (m, 4 H) ppm; [M+H]+ 385.1; LC-MS (254 nm) Purity: >99%; t_R=4.03 min; HPLC (254 nm) Purity: >99%; t_R=4.14 min.

Example 17

8-chloro-N-((3,3-difluoro-5-methylcyclohexyl)methyl)-3-(2-methoxyethyl)indolizine-1-carboxamide (13)

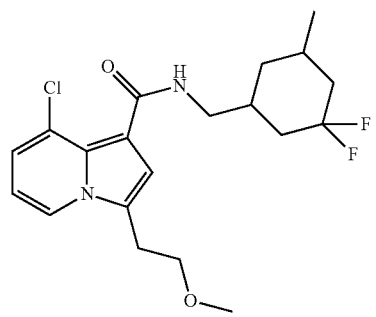 [SMILES: COCCc1cc(C(=O)NCC2CC(C)CC(F)(F)C2)c2c(Cl)cccn12]

The title compound was synthesized (90 mg, 57%) according to the procedure described in example 1 using 8-chloro-3-(2-methoxyethyl) indolizine-1-carboxylic acid (0.200 g, 0.79 mmol), (3,3-difluoro-5-methylcyclohexyl)methanamine (0.129 g, 0.79 mmol), HOBt (0.160 g, 1.18 mmol), EDCI (0.226 g, 1.18 mmol) in DCM (30 mL) and DIPEA (0.305 g, 2.36 mmol) as the starting materials.

1H NMR (500 MHz, DMSO-d₆) δ8.17 (d, J=7.0 Hz, 1 H), 8.08 (t, J=5.5 Hz, 1 H), 6.95 (d, J=7.0 Hz, 1 H), 6.78 (brs, 1 H), 6.66 (t, J=7.0 Hz, 1 H), 3.65 (t, J=6.5 Hz, 2 H), 3.26 (s, 3 H), 3.17 (d, J=5.0 Hz, 1 H), 3.12-3.07 (m, 3 H), 2.14-1.93 (m, 4 H), 1.77-1.51 (m, 3 H), 1.34-1.29 (m, 1 H), 0.96 (d, J=7 Hz, 3 H), ppm; m/z: 399.1 [M+H]⁺

Example 18

8-chloro-N-((3,3-difluoro-5-methylcyclohexyl)methyl)-3-(2-hydroxyethyl)indolizine-1-carboxamide (36)

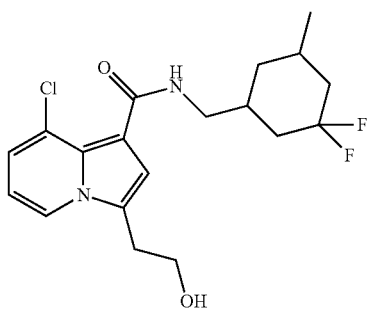 [SMILES: CC1CC(CNC(=O)c2cc(CCO)n3cccc(Cl)c23)CC(F)(F)C1]

The title compound was synthesized (23 mg, 20%) according to the procedure described in example 10 using 8-chloro-N-((3,3-difluoro-5-methylcyclohexyl)methyl)-3-(2-methoxyethyl)indolizine-1-carboxamide (0.120 g, 0.30 mmol), 15-crown-5, sodium iodide in DCM (6.3 ml, 0.3 M) and boron tribromide (1M, 1.05 mL) as the starting materials.

¹H NMR (500 MHz, DMSO-d₆) δ8.18 (d, J=7.0 Hz, 1 H), 8.07 (t, J=5.5 Hz, 1 H), 6.94 (d, J=6.5 Hz, 1 H), 6.78 (s, 1 H), 6.66 (t, J=7.0 Hz, 1 H), 4.80 (t, J=5.5 Hz, 1 H), 3.74 (q, J=6.0 Hz, 2 H), 3.28-3.26 (m, 1 H), 3.12-3.08 (m, 1 H), 3.01 (t, J=6.5 Hz, 2 H), 2.14-1.92 (m, 4 H), 1.78-1.73 (m, 1 H), 1.64-1.52 (m, 2 H), 1.34-1.29 (m, 1 H), 0.95 (d, J=6.5 Hz, 3 H) ppm; m/z: 385.1 [M+H]⁺

Example 19

8-chloro-N-(((1R,3R)-1-hydroxy-3-methylcyclohexyl)methyl)-3-(2-methoxyethyl)indolizine-1-carboxamide (87)

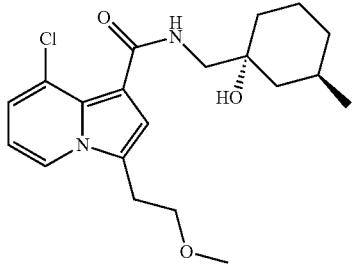 [SMILES: COCCc1cc(C(=O)NC[C@@]2(O)CCC[C@@H](C)C2)c2c(Cl)cccn12]

The title compound was synthesized according to the procedure described in example 1 using 8-chloro-3-(2-methoxyethyl) indolizine-1-carboxylic acid, and (1R,3R)-1-(aminomethyl)-3-methylcyclohexanol as the starting materials.

¹H NMR (500 MHz, DMSO-d₆): δ 8.19 (d, J=7.0 Hz, 1 H), 7.75 (t, J=5.5 Hz, 1 H), 6.96 (d, J=7.5 Hz, 1 H), 6.83 (s, 1 H), 6.68 (t, J=7.0 Hz, 1 H), 4.25 (s, 1 H), 3.67 (t, J=6.5 Hz, 2 H), 3.27 (s, 3 H), 3.18 (d, J=6.0 Hz, 2 H), 3.12 (t, J=6.5 Hz, 2 H), 1.71-1.69 (m, 1 H), 1.62-1.50 (m, 4H), 1.46-1.44 (m, 1 H), 1.28-1.18 (m, 1 H), 0.97-0.92 (m, 1H), 0.83 (d, J=6.5 Hz, 3 H), 0.78-0.71 (m, 1 H) ppm; [M+H]⁺379.1; LC-MS Purity (254 nm): 99%; $t_R$=4.07 min; HPLC Purity (254 nm): 99%; $t_R$=4.12 min; Chiral-HPLC Purity (254 nm): 99%; $t_R$=4.22 min.

Example 20

Preparation of 8-chloro-N-((3,3-difluoro-1-hydroxy-cyclohexyl)methyl)-3-(2-methoxyethyl)indolizine-1-carboxamide (24)

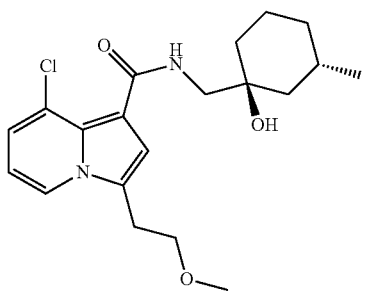 [SMILES: COCCc1cc(C(=O)NC[C@]2(O)CCC[C@H](C)C2)c2c(Cl)cccn12]

The title compound was synthesized (0.070 g, 55%, white solid) according to the procedure described in example 1 using 8-chloro-3-(2-methoxyethyl) indolizine-1-carboxylic acid (0.080 g, 0.31 mmol), HOBt (0.046 g, 0.34 mmol), EDCI (0.066 g, 0.34 mmol), DIPEA (0.122 g, 0.94 mmol), and 1-(aminomethyl)-3,3-difluorocyclohexanol (0.052 g, 0.31 mmol) as the starting materials.

¹H NMR (500 MHz, DMSO-d₆) δ 8.19 (d, J=7.0 Hz, 1 H), 7.75 (t, J=5.5 Hz, 1 H), 6.96 (dd, J=7.5 Hz, 1 H), 6.83 (s, 1 H), 6.68 (t, J=7.0 Hz, 1 H), 4.25 (s, 1 H), 3.67 (t, J=6.5 Hz, 2 H), 3.27 (s, 3 H), 3.18 (d, J=6.0 Hz, 2 H), 3.12 (t, J=6.5 Hz, 2 H), 1.74-1.69 (m, 1 H), 1.62-1.50 (m, 4 H), 1.46-1.44 (m, 1 H), 1.24-1.18 (m, 1 H), 0.97-0.92 (m, 1 H), 0.83 (d, J=6.5 Hz, 3 H), 0.81-0.71 (m, 1 H) ppm; m/z: 379.1, [M+H]⁺

Example 21

8-chloro-N-((4,4-difluoro-1-hydroxy-3-methylcyclohexyl)methyl)-3-(2-methoxyethyl)indolizine-1-carboxamide (43)

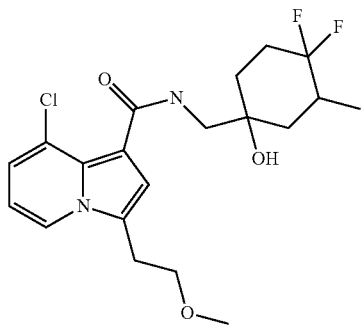 [SMILES: COCCc1cc(C(=O)NCC2(O)CCC(F)(F)C(C)C2)c2c(Cl)cccn12]

The title compound was synthesized (45 mg, 30%) according to the procedure described in example 1 using 8-Chloro-3-(2-methoxy-ethyl)-indolizine-1-carboxylic acid (150.00 mg; 0.59 mmol; 1.00 eq.), 1-Aminomethyl-4,4-difluoro-3-methyl-cyclohexanol (121.86 mg; 0.68 mmol; 1.15 eq.), (3-Dimethylamino-propyl)-ethyl-carbodiimide hydrochloride (147.36 mg; 0.77 mmol; 1.30 eq.), Benzotriazol-1-ol (103.87 mg; 0.77 mmol; 1.30 eq.) and Ethyl-diisopropyl-amine (0.29 ml; 1.77 mmol; 3.00 eq.) in N,N-Dimethyl-formamide as the starting materials.

¹H NMR (400 MHz, Chloroform-d) δ 7.89 (d, J=7.0 Hz, 1H), 7.29 (s, 1H), 6.95 (d, J=7.3 Hz, 2H), 6.61 (t, J=7.1 Hz, 1H), 6.44 (t, J=6.1 Hz, 1H), 3.75 (t, J=6.4 Hz, 2H), 3.66 (d, J=6.1 Hz, 2H), 3.39 (s, 3H), 3.10 (t, J=6.5 Hz, 2H), 2.27-1.49 (m, 6H), 1.08 (d, J=6.6 Hz, 3H). m/z: 415.0 [M+H]⁺

Example 22

8-chloro-N-(2-(1-hydroxycyclopentyl)ethyl)-3-(2-methoxyethyl)indolizine-1-carboxamide (59)

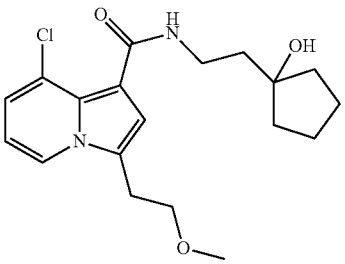 [SMILES: COCCc1cc(C(=O)NCCC2(O)CCCC2)c2c(Cl)cccn12]

The title compound was synthesized (141 mg, 65%) according to the procedure described in example 1 using 8-Chloro-3-(2-methoxy-ethyl)-indolizine-1-carboxylic acid (150.00 mg; 0.59 mmol; 1.00 eq.), 1-(2-Amino-ethyl)-cyclopentanol (87.85 mg; 0.68 mmol; 1.15 eq.), (3-Dimethylamino-propyl)-ethyl-carbodiimide hydrochloride (147.36 mg; 0.77 mmol; 1.30 eq.), Benzotriazol-1-ol (103.87 mg; 0.77 mmol; 1.30 eq.) (HOBt) and Ethyl-diisopropyl-amine (0.29 ml; 1.77 mmol; 3.00 eq.) as the starting materials.

¹H NMR (400 MHz, DMSO-d6) δ 8.16 (d, J=7.1 Hz, 1H), 7.90 (t, J=5.6 Hz, 1H), 6.94 (d, J=7.1 Hz, 1H), 6.77 (s, 1H), 6.66 (t, J=7.0 Hz, 1H), 4.17 (s, 1H), 3.66 (t, J=6.4 Hz, 2H), 3.37 (m, 2H), 3.27 (s, 3H), 3.10 (t, J=6.4 Hz, 2H), 1.89-1.33 (m, 10H). m/z: 365 [M+H]⁺

Example 23

8-chloro-N-(2-chloro-3-(trifluoromethyl)benzyl)-3-(2-methoxyethyl) indolizine-1-carboxamide (3)

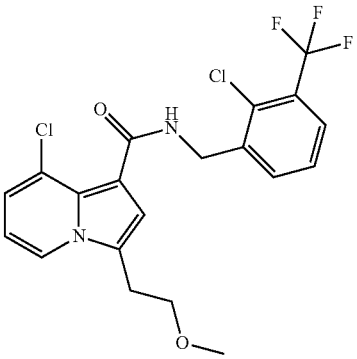 [SMILES: COCCc1cc(C(=O)NCc2cccc(C(F)(F)F)c2Cl)c2c(Cl)cccn12]

The title compound was synthesized (161 mg, 61%) according to the procedure described in example 1 using 8-Chloro-3-(2-methoxy-ethyl)-indolizine-1-carboxylic acid (150.00 mg; 0.59 mmol; 1.00 eq.), 2-Chloro-3-trifluoromethyl-benzylamine (142.52 mg; 0.68 mmol; 1.15 eq.), (3-Dimethylamino-propyl)-ethyl-carbodiimide hydrochloride (147.36 mg; 0.77 mmol; 1.30 eq.)(EDCI), Benzotriazol-1-ol (103.87 mg; 0.77 mmol; 1.30 eq.) (HOBt) and Ethyl-diisopropyl-amine (0.29 ml; 1.77 mmol; 3.00 eq.) as the starting materials.

$^1$H NMR (400 MHz, DMSO-d6) δ 8.67 (t, J=5.9 Hz, 1H), 8.22 (d, J=7.0 Hz, 1H), 7.85-7.73 (m, 2H), 7.58 (t, J=7.8 Hz, 1H), 6.99 (d, J=7.1 Hz, 1H), 6.93 (s, 1H), 6.71 (t, J=7.0 Hz, 1H), 4.58 (d, J=5.9 Hz, 2H), 3.69 (t, J=6.4 Hz, 2H), 3.29 (s, 3H), 3.14 (t, J=6.5 Hz, 2H). m/z: 446.0[M+H]$^+$

Example 24

8-chloro-N-[(4,4-difluorocyclohexyl)methyl]-3-[2-(trideuteriomethoxy)ethyl]-Nrideuteriomethyl)indolizine-1-carboxamide (72)

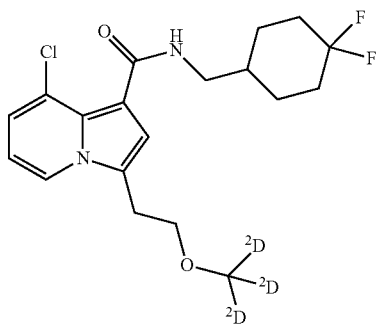 [SMILES: [2H]C([2H])([2H])OCCc1cc(C(=O)NCC2CCC(F)(F)CC2)c2c(Cl)cccn12]

Step 1: 8-Chloro-3-(2-hydroxy-ethyl)-indolizine-1-carboxylic acid (4,4-difluoro-cyclohexylmethyl)-amide The title compound was synthesized (250 mg, 64%) according to the procedure described in example 10 using 8-Chloro-3-(2-methoxy-ethyl)-indolizine-1-carboxylic acid (4,4-difluoro-cyclohexyl methyl)-amide (0.40 g, 1.03 mmol, 1.00 eq) and Pyridine hydrochloride (2.68 g, 22.69 mmol, 22.00 eq) as the starting materials. m/z: 371.20 [M+H]$^+$ Step 2. 8-chloro-N-[(4,4-difluorocyclohexyl)methyl]-3-[2-(trideuteriomethoxy)ethyl]-Nrideuteriomethyl)indolizine-1-carboxamide To a solution of 60% NaH in mineral oil (3.78 mg, 0.09 mmol, 0.80 eq) in dry THF (10.00 mL, 200.00 V) at 0° C., 8-Chloro-3-(2-hydroxy-ethyl)-indolizine-1-carboxylic acid (4,4-difluoro-cyclohexylmethyl)-amide (50.00 mg, 0.12 mmol, 1.00 eq) was added and stirred for 15 min, and trideuterio(iodo)methane (0.03 mL, 0.18 mmol, 1.50 eq) was added to the reaction mixture and reaction mixture was stirred for 16 h at room temperature under nitrogen atmosphere. The completion of the reaction was confirmed by TLC, quenched with water (10 mL) and the mixture was extracted with dichloromethane (15 mL×3) and the combined organic layer was dried over anhydrous Na$_2$SO$_4$, filtered, concentrated under vacuum. The crude was purified by silica gel chromatography and product was eluted with ethyl acetate in petroleum ether (60-70%) to afford 8-chloro-N-[(4,4-difluorocyclohexyl)methyl]-3-[2-(trideuteriomethoxy) ethyl]indolizine-1-carboxamide (3.20 mg, 0.01 mmol, 6.8%) as a white powder. $^1$H NMR (400 MHz, DMSO-d$_6$) δ 8.17 (d, J=6.80 Hz, 1H), 8.10-8.07 (m, 1H), 6.93 (d, J=7.20 Hz, 1H), 6.76 (s, 1H), 6.65 (t, J=7.20 Hz, 1H), 3.64 (t, J=6.40 Hz, 2H), 3.13-3.08 (m, 4H), 2.02-1.99 (m, 2H), 1.79-1.69 (m, 5H), 1.26-1.17 (m, 2H). m/z: 388.0 [M+H]$^+$ Example 25

8-chloro-N-(cycloheptylmethyl)-3-(2-methoxyethyl)indolizine-1-Carboxamide (1)

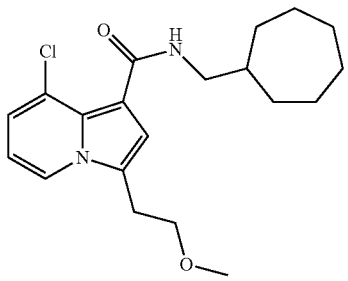 [SMILES: COCCc1cc(C(=O)NCC2CCCCCC2)c2c(Cl)cccn12]

The title compound was synthesized (0.050 g, 69.6%) according to the procedure described in example 1, using 8-chloro-3-(2-methoxyethyl)indolizine-1-carboxylic acid (0.050 g, 0.198 mmol), EDCI (0.492 g, 0.257 mmol), HOBt (0.347 g, 0.257 mmol) and TEA (0.1 mL) and Cycloheptylmethanamine (0.252 g, 0.198 mmol) as the starting materials.

$^1$H NMR (500 MHz, DMSO-d$_6$) 8.16 (d, J=7.0 Hz, 1 H), 8.00 (t, J=6.0 Hz, 1 H), 6.93 (d, J=7.0 Hz, 1 H), 6.76 (s, 1 H), 6.65 (t, J=7.0 Hz, 1 H), 3.66 (t, J=6.5 Hz, 2 H), 3.27 (s, 3 H), 3.11 (t, J=7.0 Hz, 2 H), 3.04 (t, J=6.5 Hz, 2 H), 1.77-1.70 (m, 3 H), 1.68-1.61 (m, 2 H), 1.57-1.53 (m, 2 H), 1.50-1.46 (m, 2 H), 1.42-1.35 (m, 2 H). 1.24-1.13 (m, 2 H) ppm; m/z: 363.1 [M+H]$^+$ Example 26

8-chloro-N-(cycloheptylmethyl)-3-(2-hydroxyethyl)indolizine-1-Carboxamide (6)

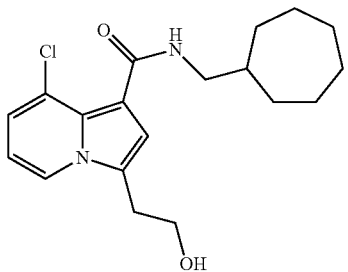 [SMILES: O=C(NCC1CCCCCC1)c1cc(CCO)n2cccc(Cl)c12]

The title compound was synthesized (0.026 g, 29.4%, light-yellow solid) according to the procedure described in example 10 using 8-chloro-N-(cycloheptylmethyl)-3-(2-methoxyethyl)-indolizine-1-carboxamide (0.092 g, 0.254 mmol), 15-crown-5 (0.5 ml, 3 M), NaI and BBr₃ (0.254 mL, 3 M in DCM) as the starting materials.

¹H NMR (500 MHz, DMSO-d$_6$) 8.16 (d, J=7.0 Hz, 1 H), 7.98 (t, J=6.0 Hz, 1 H), 6.92 (d, J=7.5 Hz, 1 H), 6.76 (s, 1 H), 6.65 (t, J=7.0 Hz, 1 H), 4.79 (t, J=5.0 Hz, 1 H), 3.74 (dd, J=6.5, 12 Hz, 2 H), 3.04 (t, J=6.5 Hz, 2 H), 3.01 (t, J=6.5 Hz, 2 H), 1.77-1.66 (m, 3 H), 1.65-1.61 (m, 2 H), 1.58-1.50 (m, 4 H), 1.49-1.35 (m, 2 H), 1.21-1.15 (m, 2 H) ppm; m/z: 349.1 [M+H]⁺

Example 27

8-chloro-N-((1-hydroxycycloheptyl)methyl)-3-(2-methoxyethyl)indolizine-1-carboxamide (35)

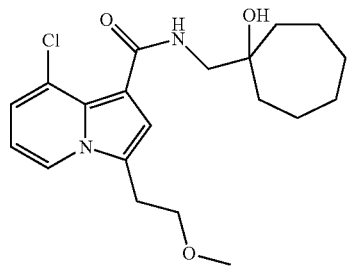 [SMILES: COCCc1cc(C(=O)NCC2(O)CCCCCC2)c2c(Cl)cccn12]

The title compound was synthesized (150 mg, 67%) according to the procedure described in example 1 using 8-Chloro-3-(2-methoxy-ethyl)-indolizine-1-carboxylic acid (150.00 mg; 0.59 mmol; 1.00 eq.), 1-Aminomethyl-cycloheptanol hydrochloride (122.19 mg; 0.68 mmol; 1.15 eq.), (3-Dimethylamino-propyl)-ethyl-carbodiimide hydrochloride (147.36 mg; 0.77 mmol; 1.30 eq.)(EDCI), Benzotriazol-1-ol (103.87 mg; 0.77 mmol; 1.30 eq.) (HOBt) and Ethyl-diisopropyl-amine (0.29 ml; 1.77 mmol; 3.00 eq.) as the starting materials.

¹H NMR (400 MHz, DMSO-d6) δ 8.20 (d, J=7.0 Hz, 1H), 7.69 (s, 1H), 6.97 (d, J=7.1 Hz, 1H), 6.70 (d, J=7.1 Hz, 1H), 4.40 (s, 1H), 3.68 (t, J=6.4 Hz, 2H), 3.28 (s, 3H), 3.23 (d, J=5.9 Hz, 2H), 3.12 (t, J=6.5 Hz, 2H), 1.83-1.14 (m, 12H). m/z: 379.0 [M+H]⁺

Intermediate 2

8-Chloro-3-(2-ethoxy-ethyl)-indolizine-1-carboxylic acid

Scheme 2

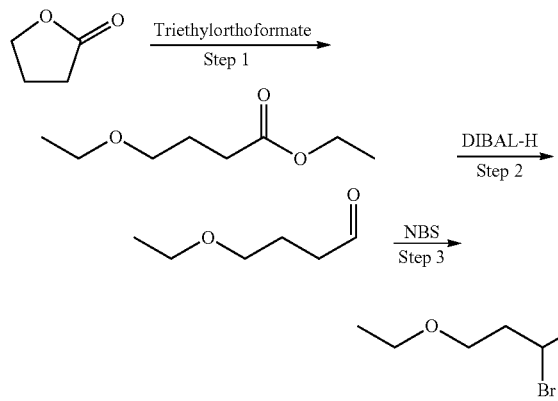

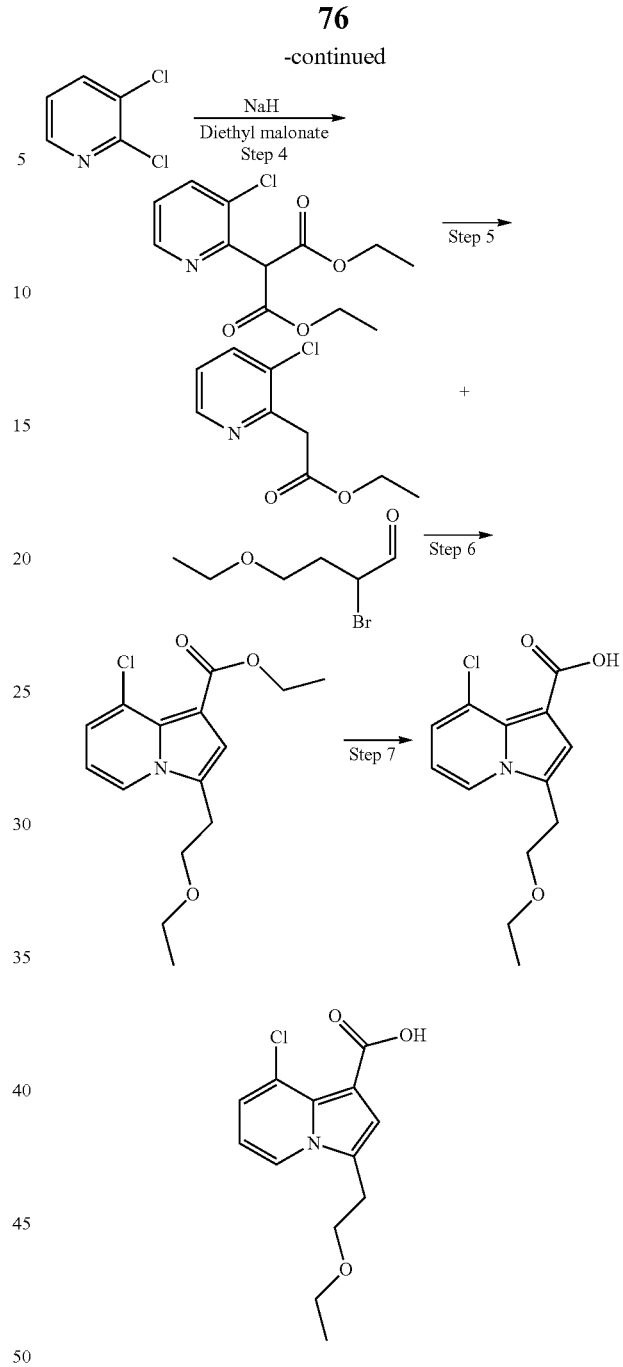

Step 1: 4-Ethoxy-butyric acid ethyl ester

To a stirred solution of dihydro-furan-2-one (22.32 mL, 287.49 mmol, 1.00 eq) in triethylorthoformate (86.95 g, 98 mL, 2.00 eq) was added conc. sulphuric acid (2.88 mL, 28.75 mmol, 0.10 eq). The mixture was heated at 50° C. for 12 h. The reaction mixture was evaporated to remove the excess ethanol at 30-35° C. and diluted with DCM (500 mL) then washed with NaHCO₃ solution (1×100 mL). The separated organic layer was dried over anhydrous Na₂SO₄, filtered and concentrated under vacuum at 35° C. The crude product was distilled under vacuum (Boiling point 50-55° C. at 0.1 mm/Hg) to provide 4-Ethoxy-butyric acid ethyl ester (35 g, 218.46 mmol, 76.0%) as a colorless liquid. ¹H NMR (400 MHz, DMSO-d$_6$) δ 4.16-4.11 (m, 2H), 3.50-3.44 (m, 3H), 2.45-2.38 (m, 2H), 1.94-1.87 (m, 2H), 1.29-1.26 (m, 4H), 1.25-1.18 (m, 2H). m/z: 373 [M+H]⁺

Step 2: 4-Ethoxy-butyraldehyde

To a stirred solution of 4-Ethoxy-butyric acid ethyl ester (30.00 g, 187.25 mmol, 1.00 eq) in DCM (300 mL, 10.00 V) at −78° C. was added DIBAL-H (IM in toluene) (205.98 mL, 205.98 mmol, 1.10 eq) and continued stirring at the same temperature for 1 h. After completion of reaction as evidenced by TLC, the reaction mixture was quenched with MeOH (20 mL), passed through celite, and washed with DCM (100 mL). The filtrate was washed with brine solution (lx 100 mL). The organic layer was separated, dried over $Na_2SO_4$, filtered and concentrated in vacuum to afford 4-Ethoxy-butyraldehyde (15.00 g, 129.13 mmol, 69.0%) as light yellow oil. The crude product was taken for the next step without further purification as confirmed by TLC.

Step 3: 2-Bromo-4-ethoxy-butyraldehyde

To a solution of 4-Ethoxy-butyraldehyde (15.00 g, 129.13 mmol, 1.00 eq) and DL Proline (3.03 g, 25.83 mmol, 0.20 eq) in dry DCM (150 mL, 10.00 V) was added 1-Bromo-pyrrolidine-2,5-dione (20.89 g, 116.22 mmol, 0.90 eq) portion wise at 0° C. After being stirred at room temperature overnight, the mixture was quenched with water (50 mL) and extracted with DCM (1×100 mL). The separated organic layer was washed with aqueous $Na_2S_2O_3$, brine and dried over anhydrous $Na_2SO_4$, filtered and concentrated in vacuum. The residue was used as such for the next step without further purification to afford 2-Bromo-4-ethoxy-butyraldehyde (10 g, 51.27 mmol, 39.7%) as dark yellow oil.

Step 4: 2-(3-Chloro-pyridin-2-yl)-malonic acid diethyl ester

To a mixture of 60% NaH (3.18 g, 79.47 mmol, 1.00 eq) in dry 1,4-dioxane (120 mL, 10.00 V) was added Malonic acid diethyl ester (25.71 g, 158.93 mmol, 2.00 eq) drop wise over a period of about 1 h at 60° C. under nitrogen atmosphere, and the mixture was stirred at the same temperature further for 0.5 h. To this mixture was added Copper (1) chloride (7.95 g, 79.47 mmol, 1.00 eq) and 2,3-Dichloro-pyridine (12.00 g, 79.47 mmol, 1.00 eq) in 50 mL of dry 1,4-dioxane drop wise at 80° C. The mixture was stirred for 22 h at reflux. After the completion of the reaction, the reaction mixture was allowed to cool to room temperature and to this reaction mixture 15 mL of hydrochloric acid, water (100 mL) and ethyl acetate (100 mL) were added and the mixture was filtered through celite. The filtrate was separated and extracted with ethyl acetate, washed with saturated brine, and dried over anhydrous $Na_2SO_4$, filtered and concentrated under reduced pressure. The crude was purified by silica gel chromatography and product was eluted with EtOAc-petroleum ether (10%-20%) to afford 3.90 g of 2-(3-Chloro-pyridin-2-yl)-malonic acid diethyl ester (3.96 g, 13.70 mmol, 17.2%) as a yellow liquid. $^1$H NMR (400 MHz, DMSO-$d_6$) δ 8.51 (dd, J=1.3, 4.7 Hz, 1H), 7.72 (dd, J=1.4, 8.1 Hz, 1H), 7.27-7.23 (m, 1H), 5.23 (s, 1H), 4.33-4.28 (m, 4H), 1.31-1.27 (m, 6H). m/z: 272.0 [M+H]$^+$

Step 5: (3-Chloro-pyridin-2-yl)-acetic acid ethyl ester

To a mixture of 2-(3-Chloro-pyridin-2-yl)-malonic acid diethyl ester (45 g, 117.26 mmol, 1.00 eq) in DMSO (450 mL, 10.00 V) at 0° C. was added NaCl (8.66 g, 140.71 mmol, 1.20 eq) and $H_2O$ (90 mL, 2.00 V), and the reaction mixture was stirred for 5 hours at 145° C. The completion of the reaction was confirmed by TLC and the reaction mixture was allowed to cool and water (50 mL) was added to the reaction mixture, and extracted with ethyl acetate (3×50 mL). The organic layer was washed with brine solution and combined organic layer was collected and dried over anhydrous $Na_2SO_4$ filtered and concentrated under reduced pressure. The crude was purified by flash chromatography and the product was eluted with ethyl acetate (20-30%) to afford (3-Chloro-pyridin-2-yl)-acetic acid ethyl ester (18 g, 80.71 mmol, 68.8%) as yellow liquid. m/z: 200 [M+H]$^+$

Step 6: 8-Chloro-3-(2-ethoxy-ethyl)-indolizine-1-carboxylic acid ethyl ester A mixture of (3-Chloro-pyridin-2-yl)-acetic acid ethyl ester (3 g, 14.09 mmol, 1.00 eq), 2-Bromo-4-ethoxybutyraldehyde (10 g, 51.27 mmol, 3.64 eq) and Sodium Bicarbonate (6.04 g, 70.46 mmol, 5.00 eq) was heated at 120° C. for 16 h. The reaction mixture was monitored by LCMS, after the complete conversion of the starting material; the reaction mixture was diluted with DCM (200 mL) and passed through celite pad. The filtrate was concentrated in vacuum and the residue was purified by column chromatography to afford 8-Chloro-3-(2-ethoxy-ethyl)-indolizine-1-carboxylic acid ethyl ester (2.50 g, 7.13 mmol, 50.6%) as a green oil. m/z: 296 [M+H]$^+$

Step 7: 8-Chloro-3-(2-ethoxy-ethyl)-indolizine-1-carboxylic acid

A solution of 8-Chloro-3-(2-ethoxy-ethyl)-indolizine-1-carboxylic acid ethyl ester (2.50 g, 7.13 mmol, 1.00 eq) in MeOH (12.50 mL, 5.00 V) was added 10% aqueous sodium hydroxide solution (12.50 mL, 5.00 V) and stirred at 80° C. for 7 h. The reaction was monitored by LCMS, and after the complete conversion of the starting material the solvent was removed under vacuum. The aqueous solution was adjusted to pH 6 with 10% aqueous potassium hydrogen sulphate, extracted with ethyl acetate, and the combined organic layer was dried over anhydrous $Na_2SO_4$, filtered, and concentrated under vacuum to afford 8-Chloro-3-(2-ethoxy-ethyl)-indolizine-1-carboxylic acid (1.60 g, 4.79 mmol, 67.1%) as a pale yellow solid. $^1$H NMR (400 MHz, CDCl$_3$) δ 8.28-8.27 (m, 1H), 7.15-7.13 (m, 1H), 7.02 (s, 1H), 6.82-6.78 (m, 1H), 3.71 (t, J=6.4 Hz, 2H), 3.48-3.43 (m, 2H), 3.08-3.09 (m, 2H), 1.09 (t, J=7.0 Hz, 3H). m/z: 268.0 [M+H]$^+$

Example 28

8-Chloro-3-(2-ethoxy-ethyl)-indolizine-1-carboxylic acid ((1R,3R)-1-hydroxy-3-methyl-cyclohexylmethyl)-amide (76)

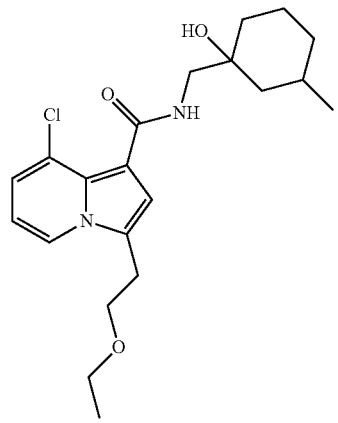 [SMILES: CCOCCc1cc(C(=O)NCC2(O)CCCC(C)C2)c2c(Cl)cccn12]

A mixture of 8-Chloro-3-(2-ethoxy-ethyl)-indolizine-1-carboxylic acid (100 mg, 0.33 mmol, 1.00 eq), Aminomethyl-3-methyl-cyclohexanol (76.25 mg, 0.49 mmol, 1.50 eq), (3-Dimethylamino-propyl)-ethyl-carbodiimide hydrochloride (107.84 mg, 0.56 mmol, 1.70 eq), Benzotriazol-1-ol (71.54 mg, 0.52 mmol, 1.60 eq) and Ethyldiisopropyl amine (0.31 mL, 1.80 mmol, 5.50 eq) in dry THF (10 mL, 100 V) was stirred at room temperature for overnight. The reaction was quenched with water (10 mL) and the mixture was extracted with dichloromethane (15 mL×3) and the combined organic layer was dried over anhydrous $Na_2SO_4$, filtered, and concentrated under vacuum. The crude was purified by silica gel chromotography and the product was eluted with ethyl acetate in petroleum ether (60%-70%) to afford 8-Chloro-3-(2-ethoxy-ethyl)-indolizine-1-carboxylic acid ((1R,3R)-1-hydroxy-3-methyl-cyclohexylmethyl)-amide (50.00 mg, 0.13 mmol, 38.5%) as a white powder. $^1$H NMR (400 MHz, DMSO-$d_6$) δ 8.18-8.17 (m, 1H), 7.75 (t, J=6.0 Hz, 1H), 6.96-6.94 (m, 1H), 6.82 (s, 1H), 6.68-6.65 (m, 1H), 4.25 (s, 1H), 3.71-3.68 (m, 2H), 3.48-3.43 (m, 2H), 3.32-3.10 (m, 4H), 1.59-1.44 (m, 5H), 1.20-1.07 (m, 4H), 0.97-0.90 (m, 3H), 0.82-0.74 (m, 1H). m/z: 393.20 [M+H]$^+$ Example 29

8-Chloro-3-(2-ethoxy-ethyl)-indolizine-1-carboxylic acid ((1S,3S)-1-hydroxy-3-ethyl-cyclohexylmethyl)-amide (77)

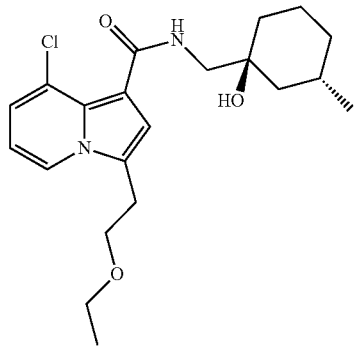 [SMILES: CCOCCc1cc(C(=O)NC[C@]2(O)CCC[C@H](C)C2)c2c(Cl)cccn12]

A racemic mixture of 8-Chloro-3-(2-ethoxy-ethyl)-indolizine-1-carboxylic acid (1-hydroxy-3-methyl-cyclohexylmethyl)-amide (30.00 mg, 1.00 eq) was separated by chiralcel HPLC to afford 8-Chloro-3-(2-ethoxy-ethyl)-indolizine-1-carboxylic acid ((1S,3S)-1-hydroxy-3-ethyl-cyclohexylmethyl)-amide (10.00 mg, 50.0%) as a white powder.
MOBILE PHASE: 0.1% DEA IN HEXANE:IPA::80:20
COLUMN: CHIRALCEL OD-H (250×4.6) mm, 5 μm
Flow rate: 1.0 mL\min
$^1$H NMR (400 MHz, DMSO-$d_6$) δ 8.18-8.17 (m, 1H), 7.75 (t, J=6.0 Hz, 1H), 6.96-6.94 (m, 1H), 6.82 (s, 1H), 6.68-6.65 (m, 1H), 4.25 (s, 1H), 3.71-3.68 (m, 2H), 3.48-3.43 (m, 2H), 3.32-3.10 (m, 4H), 1.59-1.44 (m, 5H), 1.20-1.07 (m, 4H), 0.97-0.90 (m, 3H), 0.82-0.74 (m, 1H). m/z: 393.20 [M+H]$^+$ Example 30

8-Chloro-3-(2-ethoxy-ethyl)-indolizine-1-carboxylic acid ((1R,3R)-1-hydroxy-3-ethyl-cyclohexylmethyl)-amide (73)

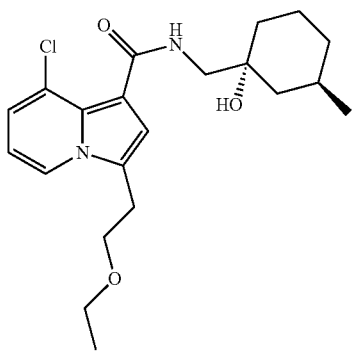 [SMILES: CCOCCc1cc(C(=O)NC[C@@]2(O)CCC[C@@H](C)C2)c2c(Cl)cccn12]

A racemic mixture of 8-Chloro-3-(2-ethoxy-ethyl)-indolizine-1-carboxylic acid (1-hydroxy-3-methyl-cyclohexylmethyl)-amide (30.00 mg, 1.00 eq) was separated by chiralcel HPLC to afford 8-Chloro-3-(2-ethoxy-ethyl)-indolizine-1-carboxylic acid ((1R,3R)-1-hydroxy-3-ethyl-cyclohexylmethyl)-amide (10.00 mg, 50.0%) as a white powder.
MOBILE PHASE: 0.1% DEA IN HEXANE:IPA:80:20
COLUMN: CHIRALCEL OD-H (250×4.6) mm, 5 μm
Flow rate: 1.0 mL\min
$^1$H NMR (400 MHz, DMSO-$d_6$) δ 8.19-8.17 (m, 1H), 7.73 (t, J=6.0 Hz, 1H), 6.98-6.96 (m, 1H), 6.81 (s, 1H), 6.69-6.65 (m, 1H), 4.21 (s, 1H), 3.70-3.68 (m, 2H), 3.48-3.43 (m, 2H), 3.32-3.10 (m, 4H), 1.58-1.43 (m, 5H), 1.20-1.07 (m, 4H), 0.97-0.91 (m, 3H), 0.82-0.74 (m, 1H). m/z: 393.20 [M+H]$^+$ Example 31

8-Chloro-3-(2-ethoxy-ethyl)-indolizine-1-carboxylic acid (4,4-difluoro-cyclohexyl methyl)-amide (19)

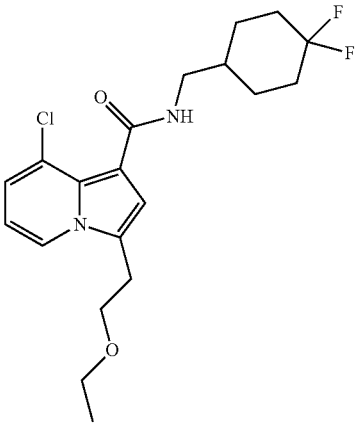 [SMILES: CCOCCc1cc(C(=O)NCC2CCC(F)(F)CC2)c2c(Cl)cccn12]

The title compound was synthesized (20 mg, 24%) according to the procedure described in example 1 using 8-Chloro-3-(2-ethoxy-ethyl)-indolizine-1-carboxylic acid (100 mg, 1.00 eq), C-(4,4-Difluorocyclohexyl)-methylamine (43.98 mg, 0.29 mmol, 1.50 eq), (3-Dimethylamino-propyl)-ethyl-carbodiimide hydrochloride (64.70 mg, 0.33 mmol, 1.70 eq), Benzotriazol-1-ol (42.92 mg, 0.31 mmol, 1.60 eq) and Ethyl-diisopropyl-amine (0.19 mL, 1.08 mmol, 5.50 eq) as the starting materials.

$^1$H NMR (400 MHz, DMSO-d$_6$) δ 8.18 (d, J=6.8 Hz, 1H), 8.08 (t, J=5.2 Hz, 1H), 6.93 (d, J=7.2 Hz, 1H), 6.77 (s, 1H), 6.67-6.63 (m, 1H), 3.69 (t, J=6.4 Hz, 2H), 3.48-3.43 (m, 2H), 3.14-3.08 (m, 4H), 2.02-1.99 (m, 2H), 1.80-1.69 (m, 5H), 1.26-1.20 (m, 2H), 1.11-1.08 (m, 3H). m/z: 399.0. [M+H]

Example 32

8-Chloro-3-(2-ethoxy-ethyl)-indolizine-1-carboxylic acid (4,4-difluoro-1-hydroxy-cyclohexyl methyl)-amide (69)

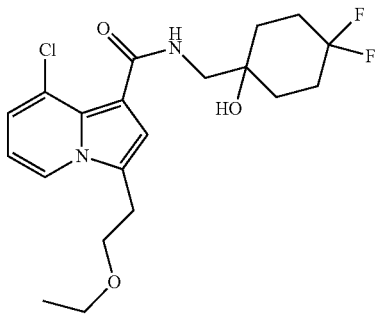 [SMILES: CCOCCc1cc(C(=O)NCC2(O)CCC(F)(F)CC2)c2c(Cl)cccn12]

The title compound was synthesized (50 mg, 34%) according to the procedure described in example 1 using 8-Chloro-3-(2-ethoxy-ethyl)-indolizine-1-carboxylic acid (100 mg, 0.33 mmol, 1.00 eq), 1-Aminomethyl-4,4-difluoro-cyclohexanol (89.39 mg, 0.49 mmol, 1.50 eq), (3-Dimethylamino-propyl)-ethyl-carbodiimide hydrochloride (107.84 mg, 0.56 mmol, 1.70 eq), Benzotriazol-1-ol (71.54 mg, 0.52 mmol, 1.60 eq) and Ethyldiisopropyl-amine (0.31 mL, 1.80 mmol, 5.50 eq) as the starting materials.

$^1$H NMR (400 MHz, DMSO-d$_6$) δ 8.19 (d, J=7.2 Hz, 1H), 7.96 (t, J=6.0 Hz, 1H), 6.96 (d, J=7.2 Hz, 1H), 6.82 (s, 1H), 6.69-6.65 (m, 1H), 3.71-3.68 (m, 2H), 3.48-3.43 (m, 2H), 3.28-3.27 (m, 2H), 3.11-3.08 (m, 2H), 2.05-1.85 (m, 4H), 1.63-1.60 (m, 4H), 1.11-1.07 (m, 3H). m/z: 415.0 [M+H]$^+$

Example 33

8-Chloro-3-(2-ethoxy-ethyl)-indolizine-1-carboxylic acid (3,3-difluoro-1-hydroxy-cyclohexylmethyl)-amide (70)

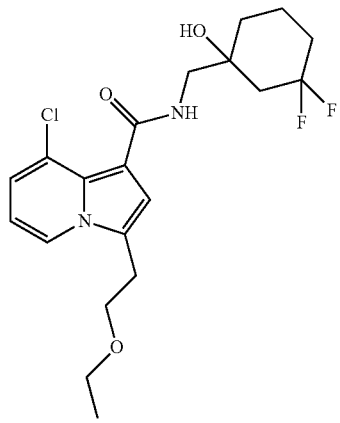 [SMILES: CCOCCc1cc(C(=O)NCC2(O)CCCC(F)(F)C2)c2c(Cl)cccn12]

The title compound was synthesized (50 mg, 36%) according to the procedure described in example 1 using 8-Chloro-3-(2-ethoxy-ethyl)-indolizine-1-carboxylic acid (100 mg, 0.33 mmol, 1.00 eq), 1-Aminomethyl-3,3-difluoro-cyclohexanol (81.17 mg, 0.49 mmol, 1.50 eq), (3-Dimethylamino-propyl)-ethyl-carbodiimide hydrochloride (107.84 mg, 0.56 mmol, 1.70 eq), Benzotriazol-1-ol (71.54 mg, 0.52 mmol, 1.60 eq) and Ethyldiisopropyl-amine (0.31 mL, 1.80 mmol, 5.50 eq) as the starting materials.

$^1$H NMR (400 MHz, DMSO-d$_6$) δ 8.20 (d, J=6.8 Hz, 1H), 7.90 (t, J=6.0 Hz, 1H), 6.97 (d, J=6.8 Hz, 1H), 6.84 (s, 1H), 6.69-6.66 (m, 1H), 3.71-3.68 (m, 2H), 3.48-3.43 (m, 2H), 3.37-3.35 (m, 1H), 3.21-3.16 (m, 1H), 3.12-3.09 (m, 2H), 2.00-1.92 (m, 3H), 1.76-1.70 (m, 2H), 1.54-1.48 (m, 3H), 1.11-1.07 (m, 3H). m/z: 415.0 [M+H]$^+$

Example 34

8-Chloro-3-(2-fluoro-ethyl)-indolizine-1-carboxylic acid (4,4-difluoro-cyclohexylmethyl)-amide (34)

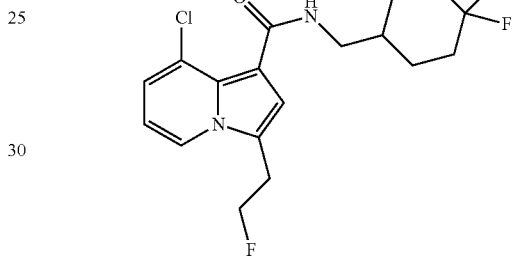

Step 1: 8-Chloro-3-(2-hydroxy-ethyl)-indolizine-1-carboxylic acid (4,4-difluoro-cyclohexyl methyl)-amide The title compound was synthesized (250.00 mg, 0.66 mmol, 64.4%) according to the procedure described in example 2 using 8-Chloro-3-(2-methoxy-ethyl)-indolizine-1-carboxylic acid (4,4-difluoro-cyclohexyl methyl)-amide (0.40 g, 1.03 mmol, 1.00 eq), and Pyridinium hydrochloride (2.68 g, 22.69 mmol, 22.00 eq) as the starting materials. m/z: 371.20 [M+H]$^+$ Step 2: 8-Chloro-3-(2-fluoro-ethyl)-indolizine-1-carboxylic acid (4,4-difluoro-cyclohexylmethyl)-amide To a stirred solution of 8-Chloro-3-(2-hydroxy-ethyl)-indolizine-1-carboxylic acid (4,4-difluoro-cyclohexylmethyl)-amide (100 mg, 0.26 mmol, 1.00 eq) in dry THF (1.00 mL, 10.00 V) at −78° C. under nitrogen atmosphere was added Diethylaminosulfur trifluoride (DAST) (0.06 mL, 0.40 mmol, 1.50 eq) and stirred for overnight at room temperature. After the completion of the reaction, the reaction mixture was quenched with 10% NaHCO$_3$ solution and extracted with ethyl acetate. The Organic layer was washed with brine solution (1×25 mL) and the combined organic layer was collected and dried over anhydrous Na$_2$SO$_4$, filtered, concentrated under vacuum to afford 8-Chloro-3-(2-fluoro-ethyl)-indolizine-1-carboxylic acid (4,4-difluoro-cyclohexylmethyl)-amide (8 mg, 0.02 mmol, 7.6%) as an off-white solid. $^1$H NMR (400 MHz, DMSO-d$_6$) δ 8.21 (d, J=6.8 Hz, 1H), 8.12-8.11 (m, 1H), 6.96 (d, J=6.4 Hz, 1H), 6.83 (s, 1H), 6.69-6.66 (m, 1H), 4.82-4.79 (m, 1H), 4.70-4.67 (m, 1H), 3.32-3.30 (m, 1H), 3.28-3.27 (m, 1H), 3.14-3.10 (m, 2H), 2.02-1.98 (m, 2H), 1.81-1.67 (m, 5H), 1.26-1.17 (m, 2H). m/z: 373 [M+H]+

Intermediate 3

3-(2-Methoxy-ethyl)-8-trifluoromethyl-indolizine-1-carboxylic acid ethyl ester

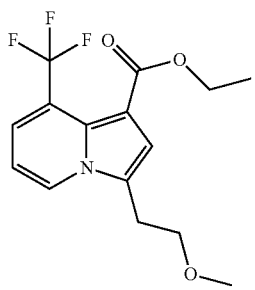 [SMILES: CCOC(=O)c1cc(CCOC)n2cccc(C(F)(F)F)c12]

A mixture of (3-Trifluoromethyl-pyridin-2-yl)-acetic acid ethyl ester (3.00 g, 11.77 mmol, 1.00 eq), 2-Bromo-4-methoxy-butyraldehyde (2.94 g, 16.24 mmol, 1.38 eq) and Sodium Bicarbonate (5.04 g, 58.85 mmol, 5.00 eq) was heated at 120° C. overnight. After cooled to room temperature, the reaction mixture was diluted with dichloromethane (200 mL) and passed through a celite bed. The filtrate was concentrated under vacuum and crude was purified by column chromatography and product was eluted with ethyl acetate in petroleum ether (20-30%) to afford 3-(2-Methoxy-ethyl)-8-trifluoromethyl-indolizine-1-carboxylic acid ethyl ester (2.10 g, 6.46 mmol, 54.9%) as a green oil. m/z: 316.20 [M+H]+

Example 35

3-(2-Methoxy-ethyl)-8-trifluoro methylindolizine-1-carboxylic acid (3,3-difluoro-1-hydroxy-cyclohexyl-methyl)-amide (60)

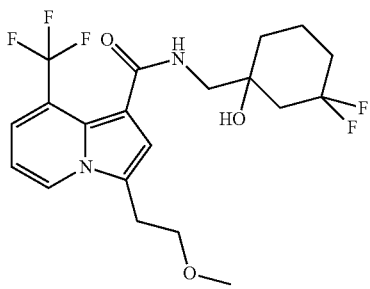

In a 25 mL microwave vial, to 3-(2-Methoxy-ethyl)-8-trifluoromethyl-indolizine-1-carboxylic acid ethyl ester (100.00 mg, 0.29 mmol, 1.00 eq) in dry THF (2.00 mL, 20.00 V) was added 1-Aminomethyl-3,3-difluoro-cyclohexanol hydrochloride (72.18 mg, 0.35 mmol, 1.20 eq) and Bis(trimethyl aluminium)-1,4-diaza bicyclo (2.2.2) octane adduct (227.09 mg, 0.88 mmol, 3.00 eq) at 0° C., then the reaction mixture was irradiated in microwave vial at 100° C. for 20 min. After completion of the reaction by TLC, The reaction mixture was diluted with dichloromethane (1×20 mL) and washed with water (1×20 mL), followed by brine solution (1×20 mL), then dried over anhydrous Na$_2$SO$_4$, filtered and evaporated. The crude residue was purified by flash column chromatography using (50-60%) ethyl acetate in petroleum ether to get 3-(2-Methoxy-ethyl)-8-trifluoro methylindolizine-1-carboxylic acid (3,3-difluoro-1-hydroxy-cyclohexylmethyl)-amide (12.00 mg, 0.03 mmol, 9.0%) as a yellow solid. $^1$H NMR (400 MHz, DMSO-d$_6$) δ 8.46-8.44 (m, 1H), 7.87-0.00 (m, 1H), 7.34-7.33 (m, 1H), 6.92 (s, 1H), 6.83-6.79 (m, 1H), 4.68 (s, 1H), 3.69-3.66 (m, 2H), 3.33-3.32 (m, 2H), 3.27-3.26 (m, 3H), 3.17-3.15 (m, 3H), 1.98-1.93 (m, 2H), 1.74-1.72 (m, 2H), 1.55-1.48 (m, 3H). m/z: 435.0 [M+H]+

Example 36

3-(2-Methoxy-ethyl)-8-trifluoromethyl-indolizine-1-carboxylic acid (4,4-difluorocyclohexylmethyl)-amide (26)

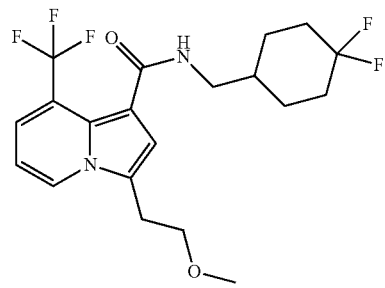 [SMILES: COCCc1cc(C(=O)NCC2CCC(F)(F)CC2)c2c(C(F)(F)F)cccn12]

The title compound was synthesized (35 mg, 30%) according to the procedure described in example 34 using 3-(2-Methoxy-ethyl)-8-trifluoromethyl-indolizine-1-carboxylic acid ethyl ester (100.00 mg, 0.28 mmol, 1.00 eq), C-(4,4-Difluoro-cyclohexyl)-methylamine (50.88 mg, 0.33 mmol, 1.20 eq) and Bis(trimethyl aluminium)-1,4-diaza bicycle (2.2.2)octane adduct (216.34 mg, 0.84 mmol, 3.00 eq) as the starting materials.

$^1$H NMR (400 MHz, DMSO-d$_6$) δ 8.42 (d, J=6.8 Hz, 1H), 8.06 (t, J=6.0 Hz, 1H), 7.30 (d, J=7.2 Hz, 1H), 6.83 (s, 1H), 6.79-6.76 (m, 1H), 3.68-3.64 (m, 2H), 3.26 (s, 3H), 3.15-3.12 (m, 2H), 3.10-3.07 (m, 2H), 2.02-1.97 (m, 2H), 1.82-1.65 (m, 5H), 1.24-1.18 (m, 2H). m/z: 419.2 [M+H]+

Example 37

3-(2-Methoxy-ethyl)-8-trifluoromethyl-indolizine-1-carboxylic acid (4,4-difluoro-1-hydroxy cyclohexyl-methyl)-amide (49)

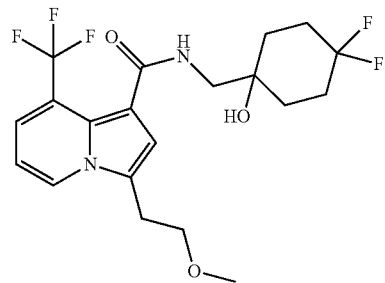 [SMILES: COCCc1cc(C(=O)NCC2(O)CCC(F)(F)CC2)c2c(C(F)(F)F)cccn12]

The title compound was synthesized (10 mg, 8%) according to the procedure described in example 34 using 3-(2-

Methoxy-ethyl)-8-trifluoromethyl-indolizine-1-carboxylic acid ethyl ester (100.00 mg, 0.27 mmol, 1.00 eq), 1-Aminomethyl-4,4-difluoro-cyclohexanol (55.17 mg, 0.33 mmol, 1.20 eq) and Bis(trimethyl aluminium)-1,4-diaza bicycle (2.2.2) octane adduct (211.88 mg, 0.82 mmol, 3.00 eq) as the starting materials.

$^1$H NMR (400 MHz, DMSO-d$_6$) δ8.44 (d, J=6.8 Hz, 1H), 7.91 (t, J=6.4 Hz, 1H), 7.33 (d, J=7.2 Hz, 1H), 6.89 (s, 1H), 6.82-6.78 (m, 1H), 4.72 (s, 1H), 3.68-3.65 (m, 2H), 3.26-3.24 (m, 5H), 3.16-3.13 (m, 2H), 2.07-1.88 (m, 4H), 1.61-1.58 (m, 4H). m/z: 435.2 [M+H]$^+$

Example 38

3-(2-Methoxy-ethyl)-8-trifluoromethyl-indolizine-1-carboxylic acid ((1R,3R)-1-hydroxy-3-methyl-cyclohexylmethyl)-amide (22)

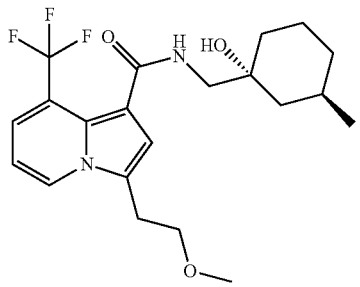

The title compound was synthesized (20 mg, 8%) according to the procedure described in example 34 using 3-(2-Methoxy-ethyl)-8-trifluoromethyl-indolizine-1-carboxylic acid ethyl ester (200.00 mg, 0.63 mmol, 1.00 eq), (1R,3R)-1-Aminomethyl-3-methyl-cyclohexanol (111.25 mg, 0.76 mmol, 1.20 eq) and Bis(trimethyl aluminium)-1,4-diaza bicycle (2.2.2)octane adduct (492.75 mg, 1.90 mmol, 3.00 eq) as the starting materials.

$^1$H NMR (400 MHz, DMSO-d$_6$) δ8.44 (d, J=7.2 Hz, 1H), 7.71 (t, J=6.0 Hz, 1H), 7.31 (d, J=6.8 Hz, 1H), 6.89 (s, 1H), 6.81-6.77 (m, 1H), 4.23 (s, 1H), 3.68-3.65 (m, 2H), 3.26 (s, 3H), 3.16-3.13 (m, 4H), 1.68-1.44 (m, 6H), 1.20-1.13 (m, 1H), 0.93-0.87 (m, 1H), 0.82-0.80 (m, 3H), 0.75-0.68 (m, 1H). m/z: 413.2 [M+H]$^+$

Intermediate 4

3-(2-Methoxy-ethyl)-8-methyl-indolizine-1-carboxylic acid ethyl ester

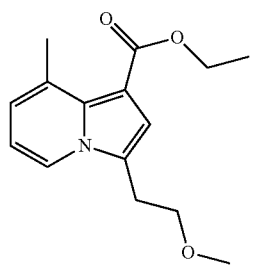 [SMILES: CCOC(=O)c1cc(CCOC)n2cccc(C)c12]

To a stirred solution of 8-Chloro-3-(2-methoxy-ethyl)-indolizine-1-carboxylic acid ethyl ester (3.00 g, 9.53 mmol, 1.00 eq) in 1,4-Dioxane (60.00 mL, 20.00 V) was added 1,1'-Bis (diphenylphosphino)ferrocene]dichloropalladium (II), complex with dichloromethane (2.41 g, 2.86 mmol, 0.30 eq) and Dimethylzinc (1.2 M in hexane) (15.89 mL, 19.06 mmol, 2.00 eq), and the reaction mixture was stirred for 30 min at room temperature, then heated at 100° C. for 1 h. The completion of the reaction was confirmed by TLC and reaction mixture was quenched with methanol (10 mL) and reaction mixture was diluted with ethyl acetate (50 mL) and washed with water (2×20 mL). The organic layer was separated and the combined organic layer was dried over anhydrous Na$_2$SO$_4$, filtered, concentrated under vacuum. The crude was purified by column chromatography and product was eluted with ethyl acetate in petroleum ether (20-30%) to afford 3-(2-Methoxy-ethyl)-8-methyl-indolizine-1-carboxylic acid ethyl ester (2.10 g, 7.00 mmol, 73.4%) as a pale green oil. $^1$H NMR (400 MHz, DMSO-d$_6$) δ 8.05-8.03 (m, 1H), 7.80 (t, J=6.0 Hz, 1H), 6.87 (s, 1H), 6.67-6.63 (m, 2H), 4.78 (s, 1H), 3.68-3.64 (m, 2H), 3.39-3.32 (m, 1H), 3.27 (s, 1H), 3.22-3.17 (m, 1H), 3.10-3.07 (m, 2H), 2.46 (s, 3H), 1.98-1.91 (m, 3H), 1.74-1.72 (m, 2H), 1.59-1.56 (m, 1H), 1.48-1.33 (m, 2H). m/z: 381.2 [M+H]$^+$ Example 39

3-(2-Methoxy-ethyl)-8-methyl-indolizine-1-carboxylic acid (3,3-difluoro-1-hydroxy-cyclohexylmethyl)-amide (57)

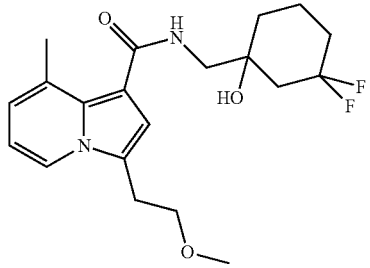 [SMILES: COCCc1cc(C(=O)NCC2(O)CCCC(F)(F)C2)c2c(C)cccn12]

The title compound was synthesized (20 mg, 13%) according to the procedure described in example 34 using 3-(2-Methoxy-ethyl)-8-methyl-indolizine-1-carboxylic acid ethyl ester (100.00 mg, 0.37 mmol, 1.00 eq), 1-Aminomethyl-3,3-difluoro-cyclohexanol hydrochloride (91.68 mg, 0.45 mmol, 1.20 eq) and Bis(trimethyl aluminium)-1,4-diaza bicyclo(2.2.2)octane adduct (288.43 mg, 1.11 mmol, 3.00 eq) as the starting materials.

$^1$H NMR (400 MHz, DMSO-d$_6$) δ 8.05-8.03 (m, 1H), 7.80 (t, J=6.1 Hz, 1H), 6.87 (s, 1H), 6.67-6.63 (m, 2H), 4.78 (s, 1H), 3.68-3.64 (m, 2H), 3.39-3.32 (m, 1H), 3.27 (s, 1H), 3.22-3.17 (m, 1H), 3.10-3.07 (m, 2H), 2.46 (s, 3H), 1.98-

1.91 (m, 3H), 1.74-1.72 (m, 2H), 1.59-1.56 (m, 1H), 1.48-1.46 (m, 2H). m/z: 381.2 [M+H]+

Example 40

3-(2-Methoxy-ethyl)-8-methyl-indolizine-1-carboxylic acid (4,4-difluoro-cyclohexylmethyl)-amide (25)

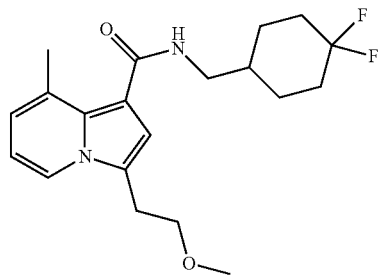 [SMILES: COCCc1cc(C(=O)NCC2CCC(F)(F)CC2)c2c(C)cccn12]

The title compound was synthesized (15 mg, 24%) according to the procedure described in example 34 using 3-(2-Methoxy-ethyl)-8-methyl-indolizine-1-carboxylic acid ethyl ester (50.00 mg, 0.17 mmol, 1.00 eq), C-(4,4-Difluoro-cyclohexyl)-methylamine (30.69 mg, 0.20 mmol, 1.20 eq) and Bis(trimethyl aluminium)-1,4-diaza bicycle (2.2.2) octane adduct (130.51 mg, 0.50 mmol, 3.00 eq) as the starting materials.

$^1$H NMR (400 MHz, DMSO-d$_6$) δ 8.03-7.99 (m, 2H), 6.79 (s, 1H), 6.64-6.62 (m, 2H), 3.65 (t, J=6.4 Hz, 2H), 3.27 (s, 3H), 3.13-3.05 (m, 4H), 2.46 (s, 3H), 2.02-1.98 (m, 2H), 1.81-1.77 (m, 3H), 1.69-1.68 (m, 2H), 1.22-1.17 (m, 4H). m/z: 365.20 [M+H]+

Example 41

3-(2-Methoxy-ethyl)-8-methyl-indolizine-1-carboxylic acid ((1R,3R)-1-hydroxy-3-methylcyclohexylmethyl)-amide (16)

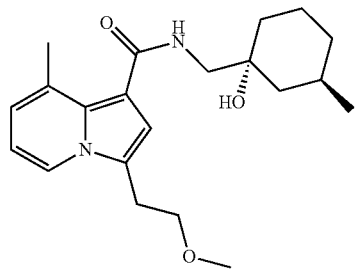

The title compound was synthesized (15 mg, 25%) according to the procedure described in example 34 using 3-(2-Methoxy-ethyl)-8-methyl-indolizine-1-carboxylic acid ethyl ester (50.00 mg, 0.16 mmol, 1.00 eq), (1R,3R)-1-Aminomethyl-3-methyl-cyclohexanol (28.86 mg, 0.20 mmol, 1.20 eq) and Bis(trimethyl aluminium)-1,4-diaza bicyclo(2.2.2)octane adduct (127.82 mg, 0.49 mmol, 3.00 eq) as the starting materials.

$^1$H NMR (400 MHz, DMSO-d$_6$) δ 8.04-8.03 (m, 1H), 7.67-7.62 (m, 1H), 6.85 (s, 1H), 6.64-6.64 (m, 2H), 4.33 (s, 1H), 3.66-3.64 (m, 2H), 3.27 (s, 3H), 3.18-3.17 (m, 2H), 3.09-3.06 (m, 2H), 2.46 (s, 3H), 1.71-1.68 (m, 1H), 1.66-1.44 (m, 5H), 1.19-1.12 (m, 1H), 0.92-0.72 (m, 5H). m/z: 359.20 [M+H]+

Example 42

3-(2-Methoxy-ethyl)-8-methyl-indolizine-1-carboxylic acid (4,4-difluoro-1-hydroxy-cyclohexylmethyl)-amide (46)

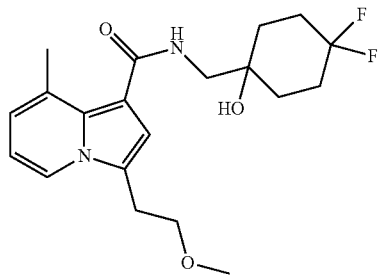 [SMILES: COCCc1cc(C(=O)NCC2(O)CCC(F)(F)CC2)c2c(C)cccn12]

The title compound was synthesized (3.5 mg, 5%) according to the procedure described in example 34 using 3-(2-Methoxy-ethyl)-8-methyl-indolizine-1-carboxylic acid ethyl ester (50 mg, 0.16 mmol, 1.00 eq), 1-Aminomethyl-4,4-difluoro-cyclohexanol (33.28 mg, 0.20 mmol, 1.20 eq) and Bis(trimethyl aluminium)-1,4-diaza bicyclo(2.2.2)octane adduct (127.82 mg, 0.49 mmol, 3.00 eq) as the starting materials.

$^1$H NMR (400 MHz, DMSO-d$_6$) δ 8.05-8.03 (m, 1H), 7.86 (t, J=6.0 Hz, 1H), 6.85 (s, 1H), 6.64-6.63 (m, 2H), 4.81 (s, 1H), 3.67-3.64 (m, 2H), 3.32-3.27 (m, 4H), 3.09-3.06 (m, 2H), 2.46 (s, 3H), 2.05-1.86 (m, 5H), 1.61-1.45 (m, 4H). m/z: 381.2 [M+H]+

Example 43

8-chloro-3-cyclobutyl-N-((4,4-difluorocyclohexyl)methyl)indolizine-1-carboxamide (5)

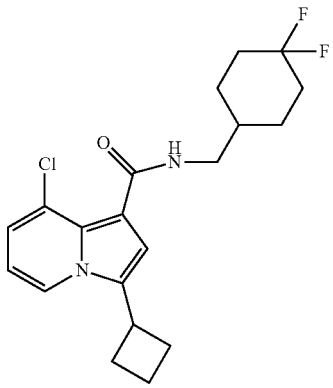 [SMILES: O=C(NCC1CCC(F)(F)CC1)c1cc(C2CCC2)n2cccc(Cl)c12]

The title compound was synthesized (95 mg, 44%) according to the procedure described in example 34 using 8-Chloro-3-cyclobutyl-indolizine-1-carboxylic acid methyl ester (150.00 mg; 0.57 mmol; 1.00 eq.), C-(4,4-Difluoro-cyclohexyl)-methylamine hydrochloride (126.71 mg; 0.68 mmol; 1.20 eq.), Ethyl-diisopropyl-amine (0.19 ml; 1.14 mmol; 2.00 eq.) and 1,4-diazabicyclo[2.2.2]octane; trimethylalumane (437.41 mg; 1.71 mmol; 3.00 eq.) as the starting materials.

$^1$H NMR (400 MHz, Chloroform-d) δ 7.60 (d, J=7.0 Hz, 1H), 6.99-6.81 (m, 2H), 6.56 (t, J=7.1 Hz, 1H), 6.11 (s, 1H), 3.79-3.59 (m, 1H), 3.41 (t, J=6.4 Hz, 2H), 2.52 (dtd, J=9.6, 7.0, 6.1, 3.5 Hz, 2H), 2.35-1.21 (m, 13H). m/z: 381 [M+H]$^+$

Example 44

8-chloro-3-cyclobutyl-N-((4,4-difluoro-1-hydroxy-cyclohexyl)methyl) indolizine-1-carboxamide (12)

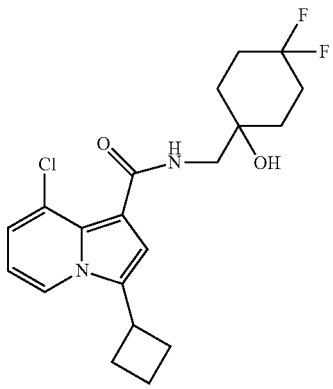 [SMILES: O=C(NCC1(O)CCC(F)(F)CC1)c1cc(C2CCC2)n2cccc(Cl)c12]

The title compound was synthesized (95 mg, 44%) according to the procedure described in example 34 using 8-Chloro-3-cyclobutyl-indolizine-1-carboxylic acid methyl ester (150.00 mg; 0.57 mmol; 1.00 eq.), 1-Aminomethyl-4,4-difluoro-cyclohexanol hydrochloride (137.63 mg; 0.68 mmol; 1.20 eq.), Ethyl-diisopropyl-amine (DIEA) (0.19 ml; 1.14 mmol; 2.00 eq.) and 1,4-diazabicyclo[2.2.2]octane; and trimethylalumane (437.41 mg; 1.71 mmol; 3.00 eq.) as the starting materials.

$^1$H NMR (400 MHz, Methanol-d4) δ 7.59 (d, J=6.9 Hz, 1H), 7.01-6.84 (m, 2H), 6.56 (t, J=7.0 Hz, 1H), 3.75-3.56 (m, 1H), 3.46 (s, 2H), 2.49 (qt, J=7.5, 3.7 Hz, 2H), 2.29-1.47 (m, 12H). m/z: 397 [M+H]$^+$

Example 45

8-chloro-3-cyclobutyl-N-((3,3-difluoro-1-hydroxy-cyclohexyl)methyl) indolizine-1-carboxamide (20)

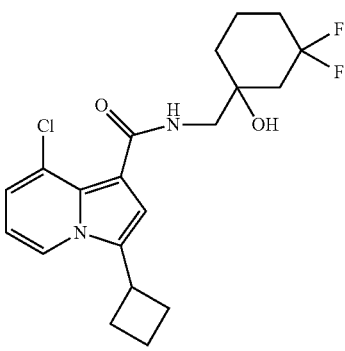 [SMILES: O=C(NCC1(O)CCCC(F)(F)C1)c1cc(C2CCC2)n2cccc(Cl)c12]

The title compound was synthesized (15 mg, 7%) according to the procedure described in example 34 using 8-Chloro-3-cyclobutyl-indolizine-1-carboxylic acid methyl ester (150.00 mg; 0.57 mmol; 1.00 eq.) 1-Aminomethyl-3,3-difluoro-cyclohexanol hydrochloride (137.63 mg; 0.68 mmol; 1.20 eq.), Ethyl-diisopropyl-amine (0.19 ml; 1.14 mmol; 2.00 eq.), and 4-diazabicyclo[2.2.2]octane; trimethylalumane (437.41 mg; 1.71 mmol; 3.00 eq.) as the starting materials. The reaction was heated in microwave at 100° C. for 5 h. m/z: 396.0[M+H]$^+$

Example 46

8-chloro-3-cyclobutyl-N-((1-hydroxy-3-(trifluoromethyl)cyclohexyl)methyl) indolizine-1-carboxamide (4)

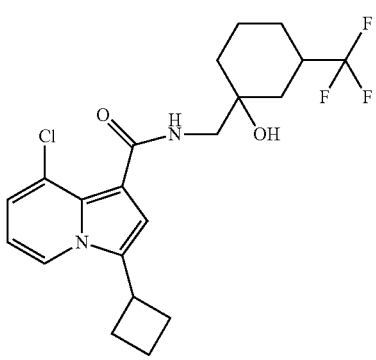 [SMILES: O=C(NCC1(O)CCCC(C(F)(F)F)C1)c1cc(C2CCC2)n2cccc(Cl)c12]

The title compound was synthesized (82 mg, 37%) according to the procedure described in example 34 using 8-Chloro-3-cyclobutyl-indolizine-1-carboxylic acid methyl ester (150.00 mg; 0.57 mmol; 1.00 eq.), 1-Aminomethyl-3-trifluoromethyl-cyclohexanol hydrochloride (159.48 mg; 0.68 mmol; 1.20 eq.), Ethyl-diisopropyl-amine (0.19 ml; 1.14 mmol; 2.00 eq.), 1,4-diazabicyclo[2.2.2]octane, and trimethylalumane (437.41 mg; 1.71 mmol; 3.00 eq.) as the starting materials.

¹H NMR (400 MHz, Chloroform-d) δ 7.61 (d, J=7.0 Hz, 1H), 6.99-6.84 (m, 2H), 6.52 (dt, J=38.4, 6.6 Hz, 2H), 3.83-3.41 (m, 3H), 2.52 (qd, J=6.1, 2.7 Hz, 2H), 2.41-1.73 (m, 9H), 1.64-1.10 (m, 4H). m/z: 429 [M+H]⁺

Example 47

8-chloro-3-cyclobutyl-N-((4,4-difluoro-1-hydroxy-3-methylcyclohexyl)methyl)indolizine-1-carboxamide (7)

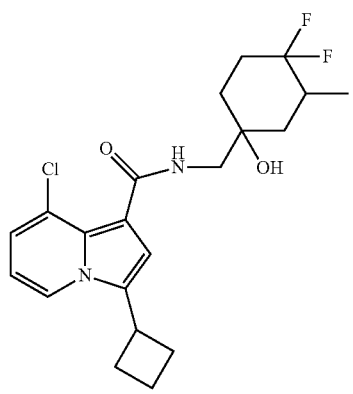 [SMILES: CC1CC(O)(CNC(=O)c2cc(C3CCC3)n3cccc(Cl)c23)CCC1(F)F]

The title compound was synthesized (82 mg, 35%) according to the procedure described in example 34 using 8-Chloro-3-cyclobutyl-indolizine-1-carboxylic acid methyl ester (150.00 mg; 0.57 mmol; 1.00 eq.), 1-Aminomethyl-4,4-difluoro-3-methyl-cyclohexanol hydrochloride (147.20 mg; 0.68 mmol; 1.20 eq.), Ethyl-diisopropyl-amine (0.19 ml; 1.14 mmol; 2.00 eq.), 1,4-diazabicyclo[2.2.2]octane; and trimethylalumane (437.41 mg; 1.71 mmol; 3.00 eq.) as the starting materials. The reaction was heated for 3 h.

¹H NMR (400 MHz, Chloroform-d) δ 7.62 (d, J=7.0 Hz, 1H), 7.03-6.87 (m, 2H), 6.67-6.33 (m, 2H), 3.68 (dd, J=12.3, 6.9 Hz, 3H), 2.52 (dq, J=9.7, 6.0, 4.8 Hz, 2H), 2.35-1.48 (m, 11H), 1.08 (d, J=6.8 Hz, 3H). m/z: 411 [M+H]⁺

Example 48

8-chloro-3-cyclobutyl-N-(((1R,3R)-1-hydroxy-3-methylcyclohexyl)methyl) indolizine-1-carboxamide (71)

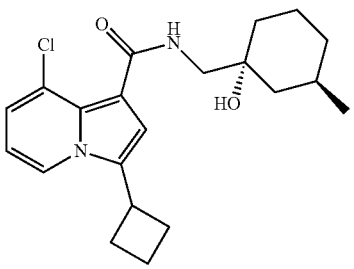 [SMILES: C[C@@H]1CCC[C@](O)(CNC(=O)c2cc(C3CCC3)n3cccc(Cl)c23)C1]

The title compound was synthesized (15 mg, 7%) according to the procedure described in example 34 using 8-Chloro-3-cyclobutyl-indolizine-1-carboxylic acid methyl ester (150.00 mg; 0.57 mmol; 1.00 eq.), (1R,3R)-1-Aminomethyl-3-methyl-cyclohexanol (97.76 mg; 0.68 mmol; 1.20 eq.) and 4-diazabicyclo[2.2.2]octane; trimethylalumane (437.41 mg; 1.71 mmol; 3.00 eq.) as the starting materials. The reaction was heated in microwave at 100° C. for 5 h.

¹H NMR (400 MHz, Chloroform-d) δ 7.61 (d, J=7.0 Hz, 1H), 6.97 (s, 1H), 6.91 (d, J=7.1 Hz, 1H), 6.56 (t, J=7.1 Hz, 1H), 6.39 (d, J=6.6 Hz, 1H), 3.83-3.59 (m, 1H), 3.48 (d, J=6.1 Hz, 2H), 2.53 (qd, J=9.5, 8.0, 2.8 Hz, 2H), 2.35-1.50 (m, 10H), 1.36-1.18 (m, 1H), 1.06-0.72 (m, 5H).). m/z: 375.0[M+H]⁺

Scheme 3

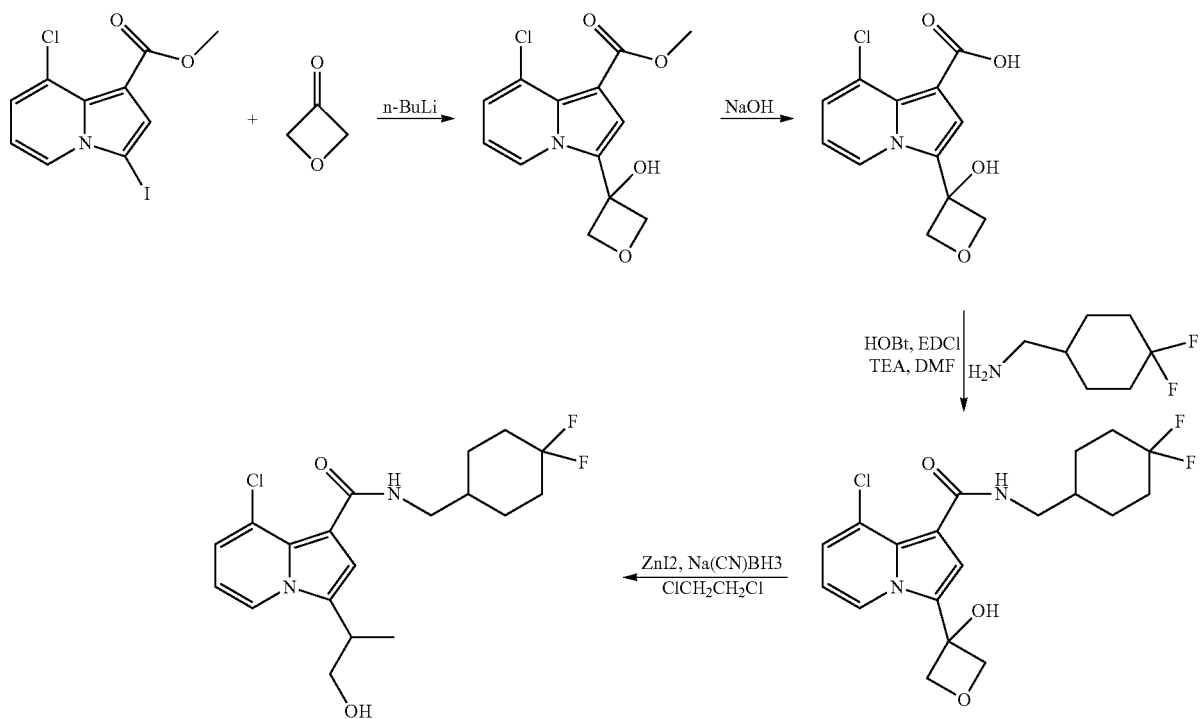

Intermediate 5

Step 1: 8-Chloro-3-(3-hydroxy-oxetan-3-yl)-indolizine-1-carboxylic acid methyl ester

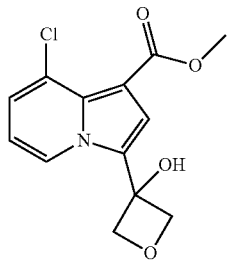 [SMILES: COC(=O)c1cc(C2(O)COC2)n2cccc(Cl)c12]

To a solution of 8-Chloro-3-iodo-indolizine-1-carboxylic acid methyl ester (1000.00 mg; 2.98 mmol; 1.00 eq.) in anhydrous THF (100 mL), cooled to −78° C., was added butyllithium (229.09 mg; 3.58 mmol; 1.20 eq.) (1.6M in hexane). The mixture was stirred for 20 minutes at this temperature. Then Oxetan-3-one (322.17 mg; 4.47 mmol; 1.50 eq.) was added and the mixture was stirred for another 2 hours. The mixture was poured into satd. NH$_4$Cl solution (200 mL) and extracted with Ethyl Acetate (200 mL). The combined organic phase was washed with saturated brine (250 mL), dried with anhydrous Na$_2$SO$_4$, filtered and concentrated in vacuum. The residue was purified by silica gel chromatography (hexanes/EA=1/1) to afford 8-Chloro-3-(3-hydroxy-oxetan-3-yl)-indolizine-1-carboxylic acid methyl ester. m/z: 282.0 [M+H]$^+$

Step 2: 8-Chloro-3-(3-hydroxy-oxetan-3-yl)-indolizine-1-carboxylic acid

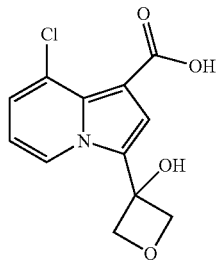 [SMILES: O=C(O)c1cc(C2(O)COC2)n2cccc(Cl)c12]

A mixture of 8-Chloro-3-(3-hydroxy-oxetan-3-yl)-indolizine-1-carboxylic acid methyl ester (300 mg, 1.06 mmol) in THF/MeOH (2 mL/2 mL) and sodium hydroxide (425.97 mg, 10.65 mmol) in water (1 ml) was stirred 2 h at 70° C. The solvent was removed and the crude product was purified on reverse phase column. m/z: 268.0[M+H]$^+$

Example 49

8-Chloro-3-(3-hydroxy-oxetan-3-yl)-indolizine-1-carboxylic acid (4,4-difluoro-cyclohexylmethyl)-amide (58)

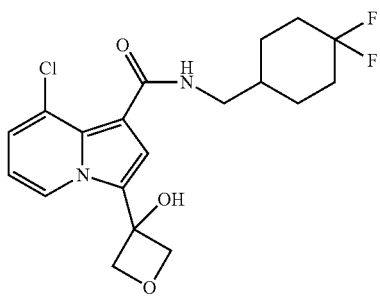 [SMILES: O=C(NCC1CCC(F)(F)CC1)c1cc(C2(O)COC2)n2cccc(Cl)c12]

The title compound was synthesized (27 mg, 67%) according to the procedure described in example 1 using 8-Chloro-3-(3-hydroxy-oxetan-3-yl)-indolizine-1-carboxylic acid sodium (30.00 mg; 0.10 mmol; 1.00 eq.), C-(4,4-Difluoro-cyclohexyl)-methylamine (18.54 mg; 0.12 mmol; 1.20 eq.), (3-Dimethylamino-propyl)-ethyl-carbodiimide hydrochloride (23.83 mg; 0.12 mmol; 1.20 eq.) (EDCI), Benzotriazol-1-ol (16.79 mg; 0.12 mmol; 1.20 eq.) (HOBt) and ethyl-diisopropyl-amine (40.16 mg; 0.31 mmol; 3.00 eq.) as the starting materials.
$^1$H NMR (DMSO-d6): 8.17 (1H), 7.24 (1H), 7.06 (1H), 6.94 (1H), 6.89 (1H), 6.76 (1H), 4.98 (2H), 4.89 (2H), 3.14 (2H), 1.98 (2H), 1.81 (3H), 1,71 (1H), 1.26 (2H). m/z: 399.0[M+H]$^+$

Example 50

8-Chloro-3-(2-hydroxy-1-methyl-ethyl)-indolizine-1-carboxylic acid (4,4-difluoro-cyclohexylmethyl)-amide (75)

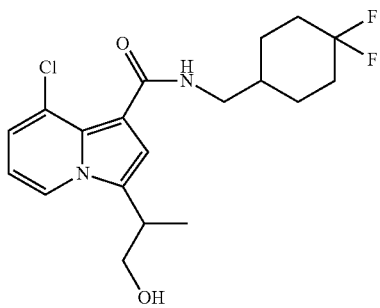 [SMILES: CC(CO)c1cc(C(=O)NCC2CCC(F)(F)CC2)c2c(Cl)cccn12]

To a solution of 8-Chloro-3-(2-hydroxy-1-methyl-ethyl)-indolizine-1-carboxylic acid (4,4-difluoro-cyclohexylmethyl)-amide (30 mg, 0.08 mmol) in 1,2-dichloroethane (10 mL) were added diiodozinc (36.02 mg, 0.11 mmol) and sodium cyanoborohydride (35.45 mg, 0.56 mmol). The mixture was refluxed for 20 hours. After cooling to room temperature, the product was purified through reverse phase HPLC (11.08 mg, 44% yield).
$^1$H NMR (chloroform-d): 7.96 (1H), 6.84 (2H), 6.60 (1H), 3.75 (2H),3.43 (2H), 3.26 (1H), 2.75 (1H), 2.15 (2H), 1.81 (3H), 1,71 (1H), 1.26 (5H). m/z: 385]M+H]$^+$

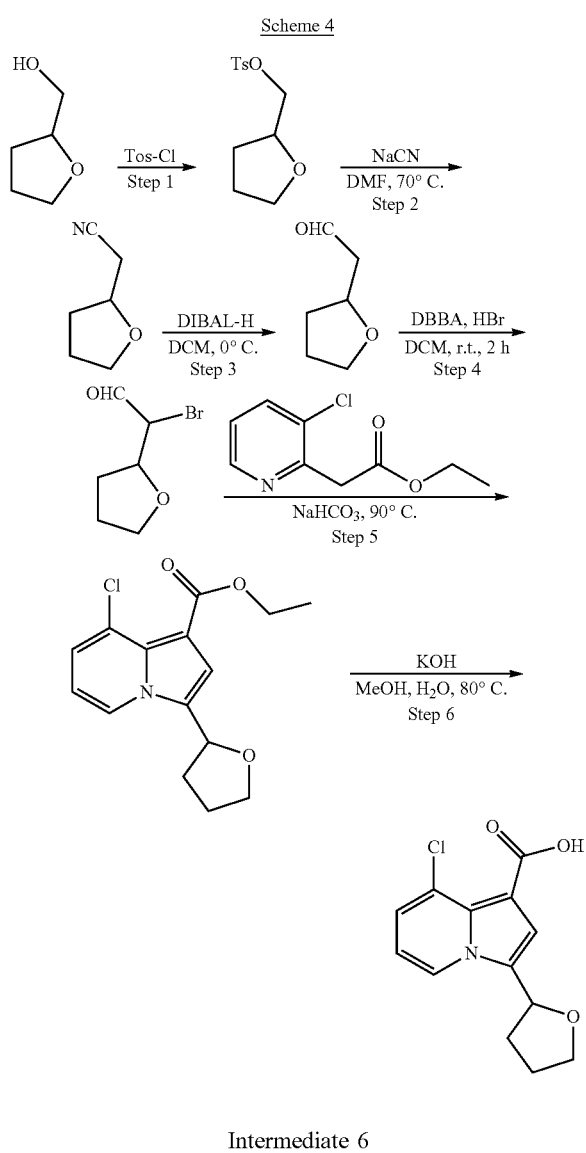

Intermediate 6

8-Chloro-3-(tetrahydro-furan-2-yl)-indolizine-1-carboxylic acid

Step 1: 2-(4-Methanesulfonyl-phenoxymethyl)-tetrahydro-furan

A mixture of (Tetrahydro-furan-2-yl)-methanol (10.00 g, 96.93 mmol, 1.00 eq) and Pyridine (20.00 mL, 2.00 V) in DCM (50.00 mL, 5.00 V) was stirred at 0° C. To this solution 4-Methyl-benzenesulfonyl chloride (22.63 g, 116.32 mmol, 1.20 eq.) was added and the reaction mixture was stirred for 2 h at room temperature. After the completion of the reaction as evidenced by TLC, water was added and extracted with DCM (1x 50 mL). The combined organic layer was dried over anhydrous Na$_2$SO$_4$, filtered and evaporated under reduced pressure to afford 2-(4-Methanesulfonyl-phenoxymethyl)-tetrahydro-furan (17 g, 66.21 mmol, 68.3%) as a colorless liquid. m/z: 257.30 [M+H]$^+$ Step 2: Tetrahydro-furan-3-yl)-acetonitrile To a stirred solution of Toluene-4-sulfonic acid tetrahydro-furan-3-ylmethyl ester (17.00 g. 65.83 mmol, 1.00 eq) in dry DMF (51.45 ml, 658.33 mmol, 10.00 eq) was added Sodium Cyanide (6.47 g, 131.67 mmol, 2.00 eq). The reaction mixture was heated overnight at 90° C., and after the completion of the reaction as confirmed by TLC, the reaction mixture was extracted with ethyl acetate (100 mL) and washed with water (3×25 mL). The combined organic layer was dried over anhydrous Na$_2$SO$_4$, filtered, concentrated under vacuum. The residue was purified by column chromatography and the product was eluted with EtOAc in petroleum ether (10-20%) to afford (Tetrahydro-furan-3-yl)-acetonitrile (3.20 g, 28.79 mmol, 43.7%) as colorless oil. $^1$H NMR (400 MHz, DMSO-d$_6$) δ 4.03-4.00 (m, 1H), 3.82-3.77 (m, 1H), 3.67-3.63 (m, 1H), 2.79-2.78 (m, 1H), 2.75-2.64 (m, 1H), 2.02-1.97 (m, 1H), 1.89-1.81 (m, 2H), 1.57-1.52 (m, 1H).

Step 3: (Tetrahydro-furan-2-yl)-acetaldehyde

To a solution of (Tetrahydro-furan-2-yl)-acetonitrile (3.20 g, 28.79 mmol, 1.00 eq) in DCM (32.00 mL, 10.00 V) was added Diisobutyl aluminium hydride (IM in toluene) (34.55 mL, 34.55 mmol, 1.20 eq) slowly at 0° C. The reaction mixture was stirred for 2 h at room temperature. The completion of the reaction was confirmed by TLC, the resulting mixture was quenched with water (50 mL) and organic layer was washed with water (3×30 mL). The combined organic layer was dried over anhydrous Na$_2$SO$_4$, filtered and evaporated under reduced pressure to afford (Tetrahydro-furan-2-yl)-acetaldehyde (2.00 g, 17.52 mmol, 60.9%) as a dark brown oil which was taken for next step without further purification.

Step 4: Bromo-(tetrahydro-furan-2-yl)-acetaldehyde

A mixture of (Tetrahydro-furan-2-yl)-acetaldehyde (2.00 g, 17.52 mmol, 1.00 eq), and 5,5-Dibromo-pyrimidine-2,4,6-trione (3.04 g, 10.51 mmol, 0.60 eq) in DCM (20.00 mL, 10.00 V) was treated with 47% aqueous solution of hydrobromic acid (0.12 mL, 0.06 V), and the reaction was stirred at room temperature for 2 h. The completion of the reaction was confirmed by TLC, the reaction mixture was filtered, the filtrate was washed with water (3×20 mL), the combined organic layer was collected, and dried over anhydrous Na$_2$SO$_4$, and filtered and concentrated under reduced pressure to afford Bromo-(tetrahydro-furan-2-yl)-acetaldehyde (1.50 g, 7.77 mmol, 44.3%) as a dark brown oil which was used directly in the next step without further purification.

Step 5: 8-Chloro-3-(tetrahydro-furan-2-yl)-indolizine-1-carboxylic acid ethyl ester To a mixture of Bromo-(tetrahydro-furan-2-yl)-acetaldehyde (1.50 g, 7.77 mmol, 1.00 eq) and (2-Chloro-pyridinyl)-acetic acid ethyl ester (0.25 g, 1.18 mmol, 0.15 eq) was added NaHCO$_3$ (0.97 g, 11.35 mmol, 1.46 eq). The reaction mixture was stirred overnight at 90° C., the completion of the reaction was confirmed by TLC, and the crude compound was directly loaded in silica gel column chromatography (30% EtOAc in petroleum ether) to provide 8-Chloro-3-(tetrahydro-furan-2-yl)-indolizine-1-carboxylic acid ethyl ester (150.00 mg, 0.34 mmol, 4.4%) as a green oil. m/z: 294.2 [M+H]$^+$ Step 6: 8-Chloro-3-(tetrahydro-furan-2-yl)-indolizine-1-carboxylic acid A solution of 8-Chloro-3-(tetrahydro-furan-2-yl)-indolizine-1-carboxylic acid ethyl ester (0.20 g, 0.65 mmol, 1.00 eq) and Potassium hydroxide (0.20 g, 3.26 mmol, 5.00 eq) in MeOH (10.00 mL, 50.00 V)/water (8.00 mL, 40.00 V) was stirred at 80° C. for 7 h. The completion of the reaction was confirmed by TLC, and the solvent was removed under vacuum. The aqueous solution was adjusted to pH 6 with 10% aqueous potassium hydrogen sulphate and extracted with ethyl acetate, the combined organic layer was dried over anhydrous $Na_2SO_4$, and concentrated under vacuum to afford 8-Chloro-3-(tetrahydro-furan-2-yl)-indolizine-1-carboxylic acid (200.00 mg, 0.42 mmol, 64.6%) as an off-white solid. m/z: 266.30 $[M+H]^+$ Example 51

8-Chloro-3-(tetrahydro-furan-2-yl)-indolizine-1-carboxylic acid (3,3-difluoro-1-hydroxy-cyclohexyl methyl)-amide (54)

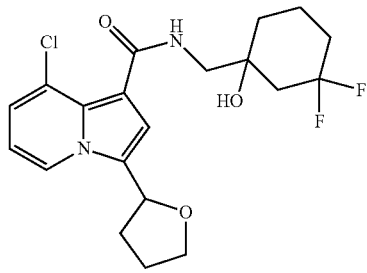 [SMILES: O=C(NCC1(O)CCCC(F)(F)C1)c1cc(C2CCCO2)n2cccc(Cl)c12]

The title compound was synthesized (11 mg, 21%) according to the procedure described in example 1 using 8-Chloro-3-(tetrahydro-furan-2-yl)-indolizine-1-carboxylic acid (50 mg, 1.00 eq), 1-Aminomethyl-3,3-difluoro-cyclohexanol (31.33 mg, 0.19 mmol, 1.50 eq), (3-Dimethylamino-propyl)-ethyl-carbodiimide hydrochloride (41.63 mg, 0.21 mmol, 1.70 eq), Benzotriazol-1-ol (38.9 mg, 1.60 eq.), and Ethyl-diisopropyl-amine (0.12 mL, 0.70 mmol, 5.50 eq) as the starting materials.

$^1$H NMR (400 MHz, DMSO-$d_6$) δ 8.24 (d, J=6.7 Hz, 1H), 7.95 (t, J=6.0 Hz, 1H), 7.05 (d, J=6.7 Hz, 1H), 7.01 (s, 1H), 6.72 (t, J=7.1 Hz, 1H), 5.20-5.22 (m, 1H), 4.66 (s, 1H), 3.83-3.79 (m, 2H), 3.21-3.16 (m, 1H), 2.32-2.25 (m, 2H), 2.05-2.23 (m, 4H), 1.74-1.70 (m, 2H), 1.56-1.48 (m, 3H). m/z: 413.2 $[M+H]^+$

Example 52

8-Chloro-3-(tetrahydro-furan-2-yl)-indolizine-1-carboxylic acid (3,3-difluoro-cyclohexyl methyl)-amide (17)

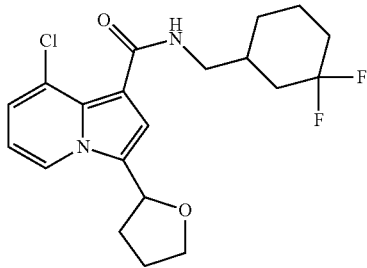 [SMILES: O=C(NCC1CCCC(F)(F)C1)c1cc(C2CCCO2)n2cccc(Cl)c12]

The title compound was synthesized (12 mg, 28%) according to the procedure described in example 1 using 8-Chloro-3-(tetrahydro-furan-2-yl)-indolizine-1-carboxylic acid (50 mg, 0.11 mmol, 1.00 eq), C-(3,3-Difluoro-cyclohexyl)-methylamine hydrochloride (29.35 mg, 0.16 mmol, 1.50 eq), (3-Dimethylamino-propyl)-ethylcarbodiimide hydrochloride (34.69 mg, 0.18 mmol, 1.70 eq), Benzotriazol-1-ol (23.01 mg, 0.17 mmol, 1.60 eq) and Ethyl-diisopropyl-amine (0.10 mL, 0.58 mmol, 5.50 eq) as the starting materials.

$^1$H NMR (400 MHz, DMSO-$d_6$) δ 8.22 (d, J=6.8 Hz, 1H), 8.14 (t, J=5.8 Hz, 1H), 7.03 (d, J=7.1 Hz, 1H), 6.94 (s, 1H), 6.70 (t, J=7.0 Hz, 1H), 5.21-5.20 (m, 1H), 3.82-3.78 (m, 2H), 3.12-3.10 (m, 2H), 2.27-2.22 (m, 2H), 2.20-2.06 (m, 1H), 2.05-1.95 (m, 3H), 1.80-1.72 (m, 3H), 1.44-1.36 (m, 2H), 1.04-1.01 (m, 1H). m/z: 397.0 $[M+H]^+$

Example 53

8-Chloro-3-(tetrahydro-furan-2-yl)-indolizine-1-carboxylic acid (4,4-difluoro-cyclohexyl methyl)-amide (23)

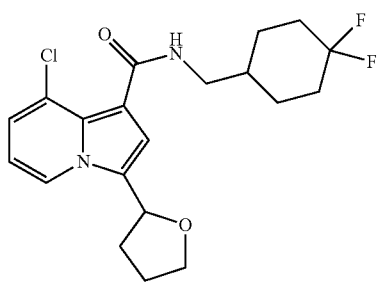 [SMILES: O=C(NCC1CCC(F)(F)CC1)c1cc(C2CCCO2)n2cccc(Cl)c12]

The title compound was synthesized (4 mg, 9%) according to the procedure described in example 1 using 8-Chloro-3-(tetrahydro-furan-2-yl)-indolizine-1-carboxylic acid (50.00 mg, 0.11 mmol, 1.00 eq), C-(4,4-Difluoro-cyclohexyl)-methylamine (23.58 mg, 0.16 mmol, 1.50 eq), (3-Dimethylamino-propyl)-ethyl-carbodiimide hydrochloride (34.69 mg, 0.18 mmol, 1.70 eq), 1-Hydroxybenzotriazole hydrate (26.08 mg, 0.17 mmol, 1.60 eq) and Ethyl-diisopropyl-amine (0.10 mL, 0.58 mmol, 5.50 eq) as the starting materials.

$^1$H NMR (400 MHz, DMSO-$d_6$) δ 8.22 (d, J=6.9 Hz, 1H), 8.13 (t, J=5.8 Hz, 1H), 7.02 (d, J=7.0 Hz, 1H), 6.93 (s, 1H), 6.70 (t, J=7.1 Hz, 1H), 5.21 (t, J=7.0 Hz, 1H), 3.82-3.78 (m, 2H), 3.12 (t, J=6.3 Hz, 2H), 2.32-2.16 (m, 2H), 2.07-1.97 (m, 4H), 1.82-1.72 (m, 5H), 1.30-1.29 (m, 2H). m/z: 397.0 $[M+H]^+$

Example 54

8-Chloro-3-(tetrahydro-furan-2-yl)-indolizine-1-carboxylic acid (4,4-difluoro-1-hydroxy-cyclohexyl methyl)-amide (48)

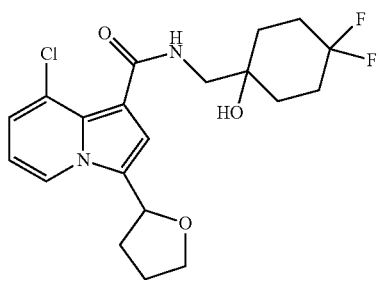 [SMILES: O=C(NCC1(O)CCC(F)(F)CC1)c1cc(C2CCCO2)n2cccc(Cl)c12]

The title compound was synthesized (15 mg, 34%) according to the procedure described in example 1 using 8-Chloro-3-(tetrahydro-furan-2-yl)-indolizine-1-carboxylic acid (50 mg, 0.11 mmol, 1.00 eq), 1-Aminomethyl-4,4-difluoro-cyclohexanol (26.17 mg, 0.16 mmol, 1.50 eq), (3-Dimethylamino-propyl)-ethyl-carbodiimide hydrochloride (34.69 mg, 0.18 mmol, 1.70 eq), Benzotriazol-1-ol (23.01 mg, 0.17 mmol, 1.60 eq) and Ethyl diisopropylamine (0.10 mL, 0.58 mmol, 5.50 eq) as the starting materials. $^1$H NMR (400 MHz, DMSO-$d_6$) δ 8.24 (d, J=6.80 Hz, 1H), 8.04 (t, J=14.6 Hz, 1H), 7.05 (d, J=6.8 Hz, 1H), 6.99 (s, 1H), 6.72 (t, J=7.0 Hz, 1H), 5.24-5.20 (m, 1H), 4.72 (s, 1H), 3.82-3.78 (m, 2H), 3.28-3.26 (m, 2H), 2.32-2.17 (m, 2H), 2.09-1.97 (m, 4H), 1.90-1.86 (m, 2H), 1.69-1.51 (m, 4H). m/z: 413.30 [M+H]$^+$ Scheme 5

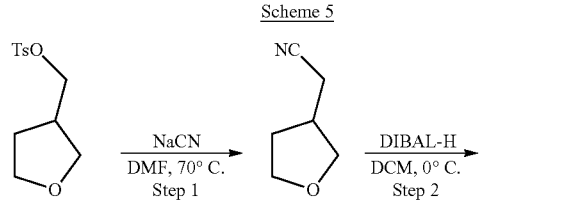

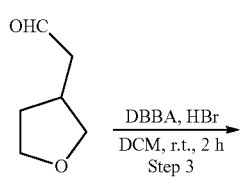

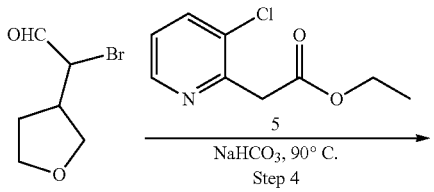

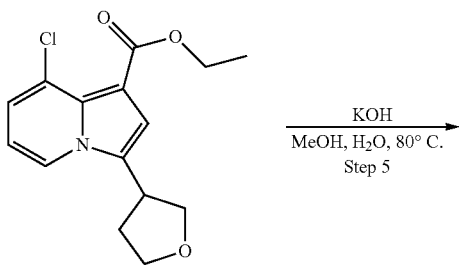

Intermediate 7

8-chloro-3-(tetrahydrofuran-3-yl)indolizine-1-carboxylic acid

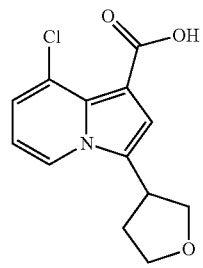 [SMILES: O=C(O)c1cc(C2CCOC2)n2cccc(Cl)c12]

Step 1: 2-(tetrahydrofuran-3-yl)acetonitrile

A mixture of (tetrahydrofuran-3-yl) methyl 4-methylbenzenesulfonate (17.0 g, 66.4 mmol) and NaCN (6.51 g, 132.8 mmol) in DMF (30 mL) was stirred at 70° C. overnight. The resulting mixture was diluted with EtOAc (200 mL), washed with brine (100 mL×3), dried over Na$_2$SO$_4$, filtered and concentrated in vacuum. The residue was purified by silica gel column chromatography (0-25% EtOAc in petroleum ether) to afford 2-(tetrahydrofuran-3-yl) acetonitrile (4.0 g, 54%) as a colorless oil. m/z: 112.30 [M+H]$^+$

Step 2: 2-(tetrahydrofuran-3-yl)acetaldehyde

To a solution of 2-(tetrahydrofuran-3-yl) acetonitrile (4.0 g, 36.0 mmol) in anhydrous DCM (40 mL) was added DIBAL-H (39.6 mL, 1 M) slowly at 0° C. The reaction mixture was stirred at room temperature overnight under nitrogen. The resulting mixture was quenched with water (50 mL). The organic layer was dried over Na$_2$SO$_4$, filtered and concentrated. The residue was purified by column chromatography on silica gel (0-25% EtOAc in petroleum ether) to afford 2-(tetrahydrofuran-3-yl) acetaldehyde (0.650 g, 16%) as a colorless oil. m/z: 115.30 [M+H]$^+$

Step 3: 2-bromo-2-(tetrahydrofuran-3-yl)acetaldehyde

A mixture of 2-(tetrahydrofuran-3-yl) acetaldehyde (0.620 g, 5.44 mmol), and 5,5-Dibromobarbituric acid (DBBA) (0.933 g, 3.26 mmol) in DCM (15 mL) was treated with HBr (40%, 0.2 mL). The reaction was stirred at room temperature for 2 h, and then filtered. The filtrate was washed with water (20 mL×3), dried over Na$_2$SO$_4$ and concentrated to give 2-bromo-2-(tetrahydrofuran-3-yl)acetaldehyde (0.630 g, 58%) as yellow oil, which was used directly in the next step without further purification.

Step 4: ethyl 8-chloro-3-(tetrahydrofuran-3-yl)indolizine-1-carboxylate

A mixture of 2-bromo-2-(tetrahydrofuran-3-yl)acetaldehyde (0.600 g, 3.1 mmol), ethyl 2-(3-chloropyridin-2-yl) acetate (0.621 g, 3.1 mmol) and NaHCO$_3$ (1.3 g, 15.5 mmol) was stirred at 90° C. under nitrogen overnight. The mixture was purified by silica gel column chromatography (30% EtOAc in petroleum ether) to afford ethyl 8-chloro-3-(tetrahydrofuran-3-yl)indolizine-1-carboxylate (0.450 g, 58%) as colorless oil. $^1$H NMR (400 MHz, DMSO-$d_6$) δ 8.37 (d, J=7.0 Hz, 1H), 7.21 (d, J=7.2 Hz, 1H), 6.87 (s, 1H), 6.85 (t, J=7.8 Hz, 1H), 4.18-4.16 (m, 2H), 4.15-4.14 (m, 1H), 3.90-3.85 (m, 3H), 3.45-3.40 (m, 1H), 2.49-2.49 (m, 1H), 2.42-2.40 (m, 1H), 2.00-1.94 (m, 1H), 1.65-1.50 (m, 3H).m/z: 294.2 [M+H]$^+$ Step 5: 8-chloro-3-(tetrahydrofuran-3-yl)indolizine-1-carboxylic acid A solution of ethyl 8-chloro-3-(tetrahydrofuran-3-yl)indolizine-1-carboxylate (0.450 g, 1.53 mmol) and KOH (0.428 g, 7.65 mmol) in MeOH (10 mL) and H$_2$O (10 mL) was stirred at 80° C. for 7 h. MeOH was removed and the resulting aqueous solution was adjusted to pH 6 with 10% aqueous KHSO$_4$ solution and extracted with EtOAc. The organic layer was dried over Na$_2$SO$_4$, filtered and concentrated to afford 8-chloro-3-(tetrahydrofuran-3-yl)indolizine-1-carboxylic acid (0.380 g, 93%) as a white solid. m/z: 266.2 [M+H]$^+$ Example 55

8-chloro-N-((4,4-difluorocyclohexyl)methyl)-3-(tetrahydro-furan-3-yl)indolizine-1-carboxamide (40)

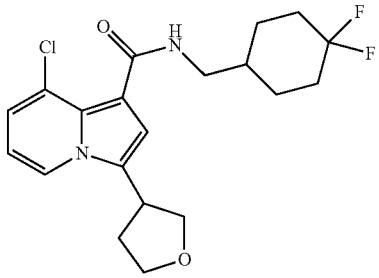

The title compound was synthesized (50 mg, 58%) according to the procedure described in example 1 using 8-chloro-3-(tetrahydrofuran-2-yl)indolizine-1-carboxylic acid (0.058 g, 0.22 mmol), (4,4-difluorocyclohexyl)methanamine (0.047 g, 0.31 mmol), EDCI (0.070 g, 0.37 mmol), HOBt (0.058 g, 0.42 mmol) and DIPEA (0.159 g, 1.23 mmol) as the starting materials.

$^1$H NMR (500 MHz, DMSO-d$_6$): δ 8.25 (d, J=7.0 Hz, 1 H), 8.10 (t, J=6.0 Hz, 1 H), 6.98 (d, J=7.0 Hz, 1 H), 6.85 (s, 1 H), 6.70 (t, J=7.0 Hz, 1 H), 4.16 (t, J=7.5 Hz, 1 H), 3.94-3.89 (m, 1H), 3.87-3.77 (s, 2 H), 3.71-3.70 (m, 1 H), 3.13 (t, J=6.0 Hz, 2 H), 2.46-2.38 (m, 1 H), 2.08-1.94 (m, 3 H), 1.84-1.67 (m, 5 H), 1.28-1.19 (m, 2 H) ppm; m/z: 397.1 [M+H]$^+$ Example 56

Preparation of 8-chloro-N-((4,4-difluoro-1-hydroxy-cyclohexyl)methyl)-3-(tetrahydrofuran-3-yl)indolizine-1-carboxamide (61)

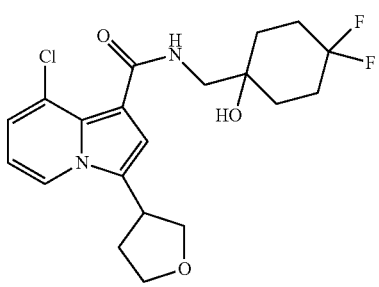 [SMILES: O=C(NCC1(O)CCC(F)(F)CC1)c1cc(C2CCOC2)n2cccc(Cl)c12]

The title compound was synthesized (55 mg, 61%) according to the procedure described in example 1 using 8-chloro-3-(tetrahydrofuran-3-yl)indolizine-1-carboxylic acid (0.060 g, 0.22 mmol), 1-(aminomethyl)-4,4-difluoro-cyclohexanol (0.056 g, 0.34 mmol), EDCI (0.073 g, 0.38 mmol), HOBt (0.048 g, 0.36 mmol) and DIPEA (0.156 g, 1.21 mmol) carboxamide (0.055 g, 61%) as the starting material.

$^1$H NMR (500 MHz, DMSO-d$_6$): 8.26 (d, J=5.5 Hz, 1 H), 7.97 (t, J=5.5 Hz, 1 H), 7.00 (d, J=7.5 Hz, 1 H), 6.91 (s, 1 H), 6.73-6.70 (m, 1 H), 4.72 (s, 1 H), 4.15 (t, J=7.0 Hz, 1 H), 3.93-3.79 (m, 3 H), 3.72-3.69 (m, 1 H), 2.51-2.36 (m, 2 H), 2.01-1.87 (m, 6 H), 1.63 (s, 4 H) ppm; m/z: 413.2 [M+H]$^+$ Example 57

8-Chloro-3-(tetrahydro-furan-3-yl)-indolizine-1-carboxylic acid (3,3-difluoro-cyclohexyl methyl)-amide (39)

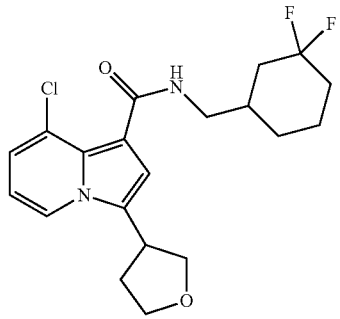 [SMILES: O=C(NCC1CCCC(F)(F)C1)c1cc(C2CCOC2)n2cccc(Cl)c12]

The title compound was synthesized (45 mg, 57%) according to the procedure described in example 1 using 8-Chloro-3-(tetrahydro-furan-3-yl)-indolizine-1-carboxylic acid (60.00 mg, 0.20 mmol, 1.00 eq), C-(3,3-Difluoro-cyclohexyl)-methylamine hydrochloride (55.15 mg, 0.30 mmol, 1.50 eq), (3-Dimethylamino-propyl)-ethylcarbodiimide hydrochloride (65.19 mg, 0.34 mmol, 1.70 eq), Benzotriazol-1-ol (43.25 mg, 0.32 mmol, 1.60 eq) and Ethyl-diisopropyl-amine (0.19 mL, 1.09 mmol, 5.50 eq) as the starting materials.

$^1$H NMR (400 MHz, DMSO-d$_6$) δ 5.76 Hz, 1H), 6.97 (d, J=7.1 Hz, 1H), 6.84 (s, 1H), 6.68 (t, J=7.1 Hz, 1H), 4.14-4.12 (m, 1H), 3.91-3.76 (m, 4H), 3.20-3.07 (m, 2H), 2.49-2.49 (m, 2H), 2.11-2.10 (m, 1H), 2.00-1.94 (m, 2H), 1.79-1.71 (m, 3H), 1.45-1.39 (m, 2H), 1.03-1.01 (m, 1H). m/z: 397.0 [M+H]$^+$

Example 58

8-Chloro-3-(tetrahydro-furan-3-yl)-indolizine-1-carboxylic acid (3,3-difluoro-1-hydroxy-cyclohexyl methyl)-amide (65)

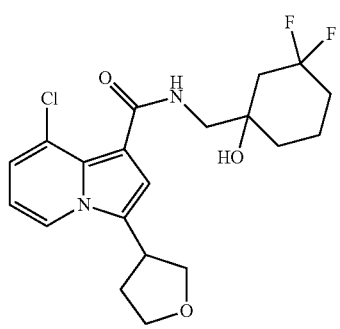 [SMILES: O=C(NCC1(O)CCCC(F)(F)C1)c1cc(C2CCOC2)n2cccc(Cl)c12]

The title compound was synthesized (45 mg, 54%) according to the procedure described in example 1 using 8-Chloro-3-(tetrahydro-furan-3-yl)-indolizine-1-carboxylic acid (60.00 mg, 0.20 mmol, 1.00 eq), 1-Aminomethyl-3,3-difluoro-cyclohexanol (49.07 mg, 0.30 mmol, 1.50 eq), (3-Dimethylamino-propyl)-ethyl-carbodiimide hydrochloride (65.19 mg, 0.34 mmol, 1.70 eq), Benzotriazol-1-ol (43.25 mg, 0.32 mmol, 1.60 eq) and Ethyl diisopropylamine (0.19 mL, 1.09 mmol, 5.50 eq) as the starting materials.

$^1$H NMR (400 MHz, DMSO-$d_6$) δ 8.26 (d, J=6.9 Hz, 1H), 7.92 (t, J=6.1 Hz, 1H), 7.00 (d, J=6.8 Hz, 1H), 6.92 (s, 1H), 6.70 (t, J=7.0 Hz, 1H), 4.60 (s, 1H), 4.15 (t, J=7.8 Hz, 1H), 3.92-3.80 (m, 3H), 3.71-3.67 (m, 1H), 3.32-3.30 (m, 1H), 3.20-3.15 (m, 1H), 2.49-2.48 (m, 1H), 2.01-1.92 (m, 4H), 1.76-1.70 (m, 2H), 1.56-1.48 (m, 3H). m/z: 413.3 [M+H]$^+$

Example 59

8-chloro-N—(((R)-3,3-difluoro-1-hydroxycyclohexyl)methyl)-3-(tetrahydrofuran-3-yl)indolizine-1-carboxamide (66)

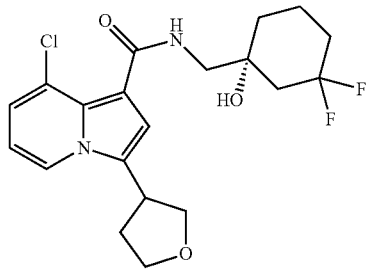 [SMILES: O=C(NC[C@@]1(O)CCCC(F)(F)C1)c1cc(C2CCOC2)n2cccc(Cl)c12]

A racemic mixture of 8-Chloro-3-(tetrahydro-furan-3-yl)-indolizine-1-carboxylic acid (3,3-difluoro-1-hydroxycyclohexylmethyl)-amide (35.00 mg, 0.08 mmol, 1.00 eq) was separated using chiralcel HPLC to provide 8-chloro-N—(((R)-3,3-difluoro-1-hydroxycyclohexyl)methyl)-3-(tetrahydrofuran-3-yl)indolizine-1-carboxamide (9 mg, 0.02 mmol, 50.9%) as a white powder.
Mobile phase: 0.1% DEA IN Hexane:IPA:80:20
Column: Chiral Cel OD-H (250×4.6) mm, 5 μm
Flow rate: 1.0 mL\min $^1$H NMR (400 MHz, DMSO-$d_6$) δ 8.26 (d, J=6.9 Hz, 1H), 7.92 (t, J=6.1 Hz, 1H), 7.00 (d, J=6.8 Hz, 1H), 6.92 (s, 1H), 6.70 (t, J=7.0 Hz, 1H), 4.60 (s, 1H), 4.15 (t, J=7.8 Hz, 1H), 3.92-3.80 (m, 3H), 3.71-3.67 (m, 1H), 3.32-3.30 (m, 1H), 3.20-3.15 (m, 1H), 2.49-2.48 (m, 1H), 2.01-1.92 (m, 4H), 1.76-1.70 (m, 2H), 1.56-1.48 (m, 3H). m/z: 413.3 [M+H]$^+$ Example 60

8-chloro-N-(((S)-3,3-difluoro-1-hydroxycyclohexyl)methyl)-3-(tetrahydrofuran-3-yl)indolizine-1-carboxamide (67)

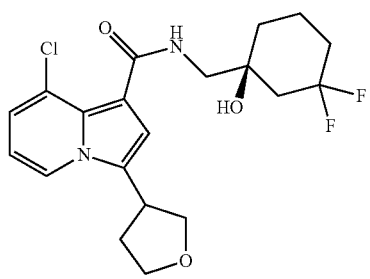 [SMILES: O=C(NC[C@]1(O)CCCC(F)(F)C1)c1cc(C2CCOC2)n2cccc(Cl)c12]

A racemic mixture of 8-Chloro-3-(tetrahydro-furan-3-yl)-indolizine-1-carboxylic acid (3,3-difluoro-1-hydroxy cyclohexylmethyl)-amide (35.00 mg, 0.08 mmol, 1.00 eq) was separated using chiralcel HPLC to provide 8-chloro-N-(((S)-3,3-difluoro-1-hydroxycyclohexyl)methyl)-3-(tetrahydrofuran-3-yl)indolizine-1-carboxamide (5.00 mg; 0.01 mmol; 28.1%) as a white powder).

Mobile phase: 0.1% DEA IN Hexane:IPA:80:20
Column: Chiral Cel OD-H (250×4.6) mm, 5 μm
Flow rate: 1.0 mL\min $^1$H NMR (400 MHz, DMSO-$d_6$) δ 8.26 (d, J=6.9 Hz, 1H), 7.92 (t, J=6.1 Hz, 1H), 7.00 (d, J=6.8 Hz, 1H), 6.92 (s, 1H), 6.70 (t, J=7.0 Hz, 1H), 4.60 (s, 1H), 4.15 (t, J=7.8 Hz, 1H), 3.92-3.80 (m, 3H), 3.71-3.67 (m, 1H), 3.32-3.30 (m, 1H), 3.20-3.15 (m, 1H), 2.49-2.48 (m, 1H), 2.01-1.92 (m, 4H), 1.76-1.70 (m, 2H), 1.56-1.48 (m, 3H). m/z: 413.3 [M+H]$^+$ Example 61

8-chloro-N-((1-hydroxy-3-(trifluoromethyl)cyclohexyl)methyl)-3-(tetrahydrofuran-3-yl)indolizine-1-carboxamide (74)

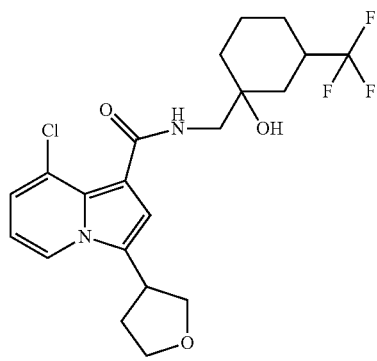 [SMILES: O=C(NCC1(O)CCCC(C(F)(F)F)C1)c1cc(C2CCOC2)n2cccc(Cl)c12]

The title compound was synthesized (67 mg, 28%) according to the procedure described in example 34 using 8-Chloro-3-(tetrahydro-furan-3-yl)-indolizine-1-carboxylic acid methyl ester (150.00 mg; 0.54 mmol; 1.00 eq), 1-Aminomethyl-3-trifluoromethyl-cyclohexanol hydrochloride (150.36 mg; 0.64 mmol; 1.20 eq.), Ethyl-diisopropyl-amine (0.18 ml; 1.07 mmol; 2.00 eq.) and diazabicyclo[2.2.2]octane; trimethylalumane (412.39 mg; 1.61 mmol; 3.00 eq.) as the starting materials.

$^1$H NMR (400 MHz, Chloroform-d) δ 7.84 (d, J=7.0 Hz, 1H), 6.96 (d, J=5.0 Hz, 2H), 6.76-6.52 (m, 2H), 4.23 (t, J=7.9 Hz, 1H), 4.11-3.78 (m, 4H), 3.76-3.39 (m, 4H), 2.59-1.73 (m, 5H), 1.61-1.13 (m, 5H). m/z: 445 [M+H]$^+$

Example 62

8-chloro-N-((4,4-difluoro-1-hydroxy-3-methylcyclohexyl)methyl)-3-(tetrahydrofuran-3-yl)indolizine-1-carboxamide (44)

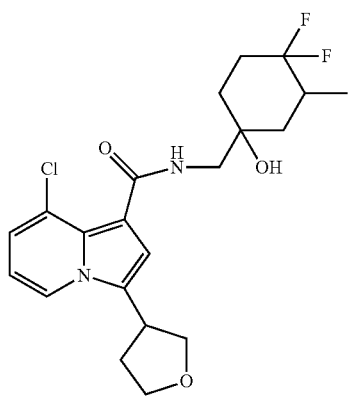 [SMILES: CC1CC(O)(CNC(=O)c2cc(C3CCOC3)n3cccc(Cl)c23)CCC1(F)F]

The title compound was synthesized (47 mg, 21%) according to the procedure described in example 34 using 8-Chloro-3-(tetrahydro-furan-3-yl)-indolizine-1-carboxylic acid methyl ester (150.00 mg; 0.54 mmol; 1.00 eq.), 1-Aminomethyl-4,4-difluoro-3-methyl-cyclohexanol hydrochloride (138.78 mg; 0.64 mmol; 1.20 eq.), Ethyl-diisopropyl-amine (DIEA) (0.18 ml; 1.07 mmol; 2.00 eq.), 1,4-diazabicyclo[2.2.2]octane; and trimethylalumane (DIAL-DABCO) (412.39 mg; 1.61 mmol; 3.00 eq.), as the starting materials. The reaction was heated for 5 h. 1H NMR (400 MHz, Chloroform-d) δ 7.82 (d, J=7.0 Hz, 1H), 6.93 (d, J=7.4 Hz, 2H), 6.77 (d, J=6.8 Hz, 1H), 6.61 (t, J=7.1 Hz, 1H), 4.21 (t, J=7.9 Hz, 1H), 4.10-3.78 (m, 4H), 3.64 (dd, J=13.9, 6.3 Hz, 3H), 2.57-2.31 (m, 1H), 2.25-1.42 (m, 9H), 1.03 (d, J=6.6 Hz, 3H). m/z: 427 [M+H]$^+$

Example 63

8-chloro-N-(((1R,3R)-1-hydroxy-3-methylcyclohexyl)methyl)-3-(tetrahydrofuran-3-yl)indolizine-1-carboxamide (38)

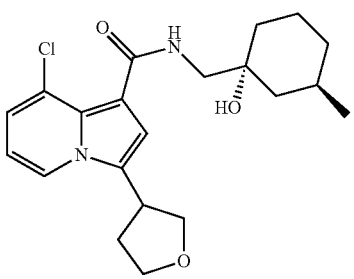 [SMILES: C[C@@H]1CCC[C@](O)(CNC(=O)c2cc(C3CCOC3)n3cccc(Cl)c23)C1]

The title compound was synthesized (47 mg, 21%) according to the procedure described in example 34 using 8-Chloro-3-(tetrahydro-furan-3-yl)-indolizine-1-carboxylic acid methyl ester (150.00 mg; 0.54 mmol; 1.00 eq), (1R, 3R)-1-Aminomethyl-3-methyl-cyclohexanol (115.21 mg; 0.80 mmol; 1.50 eq.), 1,4-diazabicyclo[2.2.2]octane; and trimethylalumane (412.39 mg; 1.61 mmol; 3.00 eq.) as the starting materials. The reaction was heated for 4 h. 1H NMR (400 MHz, Chloroform-d) δ 7.85 (d, J=6.9 Hz, 1H), 7.07-6.92 (m, 2H), 6.84-6.55 (m, 2H), 4.24 (t, J=8.0 Hz, 1H), 4.13-3.58 (m, 6H), 3.06 (s, 3H), 2.28 (ddd, J=138.7, 12.8, 6.3 Hz, 2H), 1.82-1.52 (m, 6H), 0.98-0.82 (m, 3H). m/z: 391 [M+H]$^+$

Example 64

8-chloro-N-((4,4-difluorocyclohexyl)methyl)-3-(3-hydroxytetrahydrofuran-3-yl)indolizine-1-carboxamide (55)

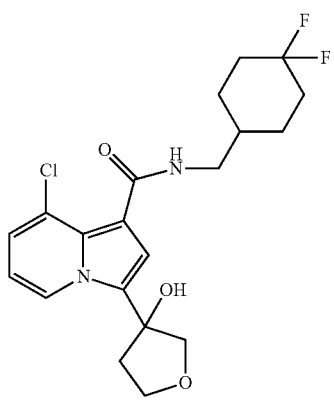 [SMILES: O=C(NCC1CCC(F)(F)CC1)c1cc(C2(O)CCOC2)n2cccc(Cl)c12]

The title compound was synthesized (4.3 mg, 1.9%) according to the procedure described in example 34 using 8-Chloro-3-(3-hydroxy-tetrahydro-furan-3-yl)-indolizine-1-carboxylic acid methyl ester (150.00 mg; 0.51 mmol; 1.00 eq.), C-(4,4-Difluoro-cyclohexyl)-methylamine hydrochloride (113.00 mg; 0.61 mmol; 1.20 eq.), Ethyl-diisopropyl-amine (0.17 ml; 1.01 mmol; 2.00 eq.), 1,4-diazabicyclo[2.2.2]octane; and trimethylalumane (390.08 mg; 1.52 mmol; 3.00 eq.) as the starting materials. m/z: 413 [M+H]$^+$

Example 65

8-chloro-N-((4,4-difluorocyclohexyl)methyl)-3-(2,5-dihydrofuran-3-yl) indolizine-1-carboxamide (21)

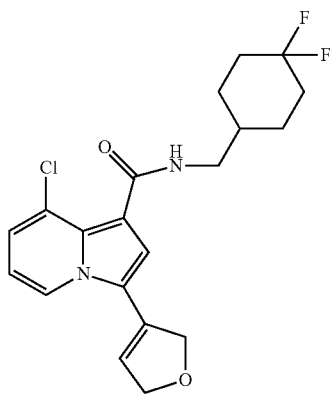 [SMILES: O=C(NCC1CCC(F)(F)CC1)c1cc(C2=CCOC2)n2cccc(Cl)c12]

The title compound was synthesized (50 mg, 25%) according to the procedure described in example 34 using 8-Chloro-3-(3-hydroxy-tetrahydro-furan-3-yl)-indolizine-1-carboxylic acid methyl ester (150.00 mg; 0.51 mmol; 1.00 eq.), C-(4,4-Difluoro-cyclohexyl)-methylamine hydrochloride (113.00 mg; 0.61 mmol; 1.20 eq.), Ethyl-diisopropyl-amine (0.17 ml; 1.01 mmol; 2.00 eq.), 1,4-diazabicyclo

Example 66

8-chloro-N-((4,4-difluorocyclohexyl)methyl)-3-(4,5-dihydrofuran-3-yl)indolizine-1-carboxamide (14)

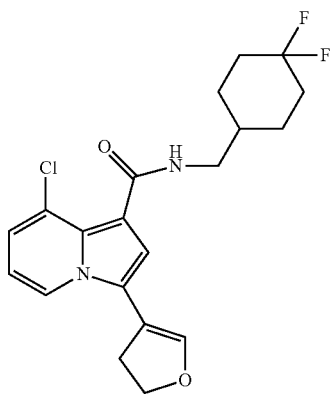 [SMILES: O=C(NCC1CCC(F)(F)CC1)c1cc(C2=COCC2)n2cccc(Cl)c12]

The title compound was synthesized (50 mg, 25%) according to the procedure described in example 34 using 8-Chloro-3-(3-hydroxy-tetrahydro-furan-3-yl)-indolizine-1-carboxylic acid methyl ester (150.00 mg; 0.51 mmol; 1.00 eq.), C-(4,4-Difluoro-cyclohexyl)-methylamine hydrochloride (113.00 mg; 0.61 mmol; 1.20 eq.), Ethyl-diisopropyl-amine (0.17 ml; 1.01 mmol; 2.00 eq.), 1,4-diazabicyclo[2.2.2]octane; and trimethylalumane (390.08 mg; 1.52 mmol; 3.00 eq.) as the starting materials.

$^1$H NMR (400 MHz, Chloroform-d) δ 7.90 (d, J=7.0 Hz, 1H), 6.98-6.87 (m, 2H), 6.83 (s, 1H), 6.63 (t, J=7.1 Hz, 1H), 6.14 (d, J=27.7 Hz, 1H), 4.53 (t, J=9.6 Hz, 2H), 3.40 (t, J=6.4 Hz, 2H), 3.09 (td, J=9.8, 2.1 Hz, 2H), 2.30-1.11 (m, 9H).

$^{13}$C NMR (101 MHz, CDCl$_3$) δ 166.14, 141.99, 127.64, 124.65, 123.05, 120.51, 119.60, 114.87, 111.90, 111.11, 105.77, 77.33, 77.22, 77.01, 76.70, 69.53, 45.00, 44.97, 36.10, 33.36, 33.13, 33.10, 32.87, 32.55, 26.84, 26.74. m/z: 395 [M+H]$^+$

Example 67

8-chloro-N-((4,4-difluorocyclohexyl)methyl)-3-(tetrahydro-2H-pyran-4-yl)indolizine-1-carboxamide (33)

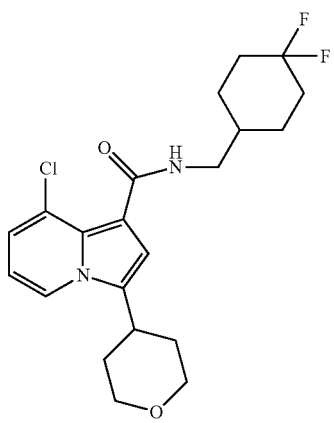 [SMILES: O=C(NCC1CCC(F)(F)CC1)c1cc(C2CCOCC2)n2cccc(Cl)c12]

The title compound was synthesized (20 mg, 10%) according to the procedure described in example 34 using 8-Chloro-3-(tetrahydro-pyran-4-yl)-indolizine-1-carboxylic acid methyl ester (150.00 mg; 0.51 mmol; 1.00 eq.), C-(4,4-Difluoro-cyclohexyl)-methylamine hydrochloride (113.76 mg; 0.61 mmol; 1.20 eq.), Ethyl-diisopropyl-amine (0.17 ml; 1.02 mmol; 2.00 eq.), 1,4-diazabicyclo[2.2.2]octane; and trimethylalumane (392.70 mg; 1.53 mmol; 3.00 eq.) as the starting materials. The reaction was heated in microwave at 100° C. for 5 h.

$^1$H NMR (400 MHz, Chloroform-d) δ 7.81 (d, J=7.0 Hz, 1H), 7.01-6.75 (m, 2H), 6.59 (t, J=7.1 Hz, 1H), 6.09 (t, J=6.2 Hz, 1H), 4.23-3.99 (m, 3H), 3.62 (t, J=11.7 Hz, 2H), 3.40 (t, J=6.5 Hz, 2H), 3.08 (dd, J=13.6, 9.4 Hz, 1H), 2.26-1.60 (m, 10H), 1.52-1.30 (m, 2H). m/z: 411.0[M+H]$^+$

Example 68

8-chloro-N-((4,4-difluoro-1-hydroxycyclohexyl)methyl)-3-(tetrahydro-2H-pyran-4-yl)indolizine-1-carboxamide (56)

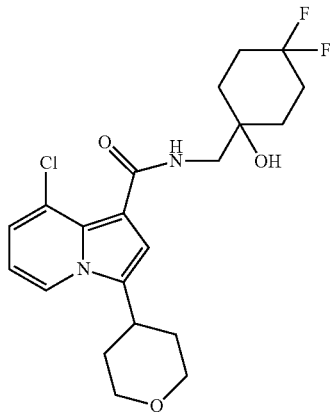 [SMILES: O=C(NCC1(O)CCC(F)(F)CC1)c1cc(C2CCOCC2)n2cccc(Cl)c12]

The title compound was synthesized (97 mg, 44%) according to the procedure described in example 34 using 8-Chloro-3-(tetrahydro-pyran-4-yl)-indolizine-1-carboxylic acid methyl ester (150.00 mg; 0.51 mmol; 1.00 eq.), 1-Aminomethyl-4,4-difluoro-cyclohexanol hydrochloride (123.56 mg; 0.61 mmol; 1.20 eq.), Ethyl-diisopropyl-amine (0.17 ml; 1.02 mmol; 2.00 eq.), 1,4-diazabicyclo[2.2.2]octane; and trimethylalumane (392.70 mg; 1.53 mmol; 3.00 eq.) as the starting materials. The reaction was heated in microwave at 100° C. for 4 h.

$^1$H NMR (400 MHz, Chloroform-d) δ 7.83 (d, J=6.8 Hz, 1H), 7.01-6.83 (m, 2H), 6.63 (dt, J=7.2, 3.6 Hz, 1H), 6.52 (d, J=6.2 Hz, 1H), 4.22-4.04 (m, 2H), 3.61 (t, J=11.7 Hz, 2H), 3.53-3.41 (m, 3H), 3.18-2.97 (m, 2H), 2.37-1.47 (m, 15H). m/z: 427.0[M+H]$^+$

Example 69

8-chloro-N-((4,4-difluoro-1-hydroxy-3-methylcyclohexyl)methyl)-3-(tetrahydro-2H-pyran-4-yl)indolizine-1-carboxamide (41)

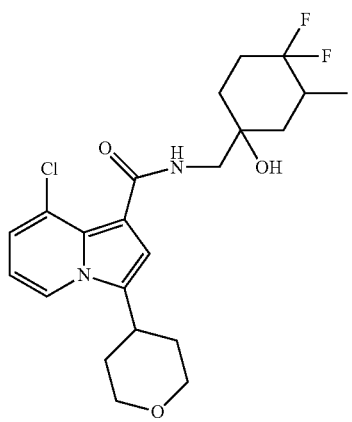 [SMILES: CC1CC(O)(CNC(=O)c2cc(C3CCOCC3)n3cccc(Cl)c23)CCC1(F)F]

The title compound was synthesized (70 mg, 31%) according to the procedure described in example 34 using 8-Chloro-3-(tetrahydro-pyran-4-yl)-indolizine-1-carboxylic acid methyl ester (150.00 mg; 0.51 mmol; 1.00 eq.), 1-Aminomethyl-4,4-difluoro-3-methyl-cyclohexanol hydrochloride (132.16 mg; 0.61 mmol; 1.20 eq.), Ethyl-diisopropyl-amine (0.17 ml; 1.02 mmol; 2.00 eq.), 1,4-diazabicyclo[2.2.2]octane; and trimethylalumane (392.70 mg; 1.53 mmol; 3.00 eq.). The reaction was heated in microwave oven at 100° C. for 5 h.

$^1$H NMR (400 MHz, Chloroform-d) δ 7.82 (d, J=7.1 Hz, 1H), 7.00-6.86 (m, 2H), 6.62 (t, J=7.1 Hz, 1H), 6.45 (d, J=7.3 Hz, 1H), 4.20-4.00 (m, 2H), 3.68-3.53 (m, 4H), 3.08 (dd, J=13.5, 9.4 Hz, 1H), 2.26-1.43 (m, 11H), 1.07 (d, J=6.7 Hz, 3H). m/z: 441.0[M+H]$^+$

Example 70

8-chloro-N-(((1R,3R)-1-hydroxy-3-methylcyclohexyl)methyl)-3-(tetrahydro-2H-pyran-4-yl)indolizine-1-carboxamide (27)

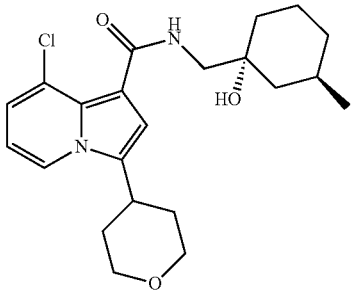 [SMILES: C[C@@H]1CCC[C@](O)(CNC(=O)c2cc(C3CCOCC3)n3cccc(Cl)c23)C1]

The title compound was synthesized (56 mg, 27%) according to the procedure described in example 34 using 8-Chloro-3-(tetrahydro-pyran-4-yl)-indolizine-1-carboxylic acid methyl ester (150.00 mg; 0.51 mmol; 1.00 eq.), (1R, 3R)-1-Aminomethyl-3-methyl-cyclohexanol (109.71 mg; 0.77 mmol; 1.50 eq.), 1,4-diazabicyclo[2.2.2]octane; and trimethylalumane (392.70 mg; 1.53 mmol; 3.00 eq.) as the starting materials. The reaction was heated in microwave at 100° C. for 5 h.

$^1$H NMR (400 MHz, Chloroform-d) δ 7.81 (d, J=7.1 Hz, 1H), 6.92 (d, J=8.4 Hz, 2H), 6.59 (t, J=7.1 Hz, 1H), 6.36 (d, J=6.3 Hz, 1H), 4.24-3.99 (m, 2H), 3.62 (t, J=11.7 Hz, 2H), 3.47 (d, J=6.0 Hz, 2H), 3.20-2.92 (m, 1H), 2.02-1.52 (m, 10H), 1.28 (dt, J=13.3, 8.6 Hz, 1H), 1.10-0.71 (m, 5H). m/z: 405.0[M+H]$^+$

Example 71

8-chloro-N-((1-hydroxy-3-(trifluoromethyl)cyclohexyl)methyl)-3-(tetrahydro-2H-pyran-4-yl)indolizine-1-carboxamide (28)

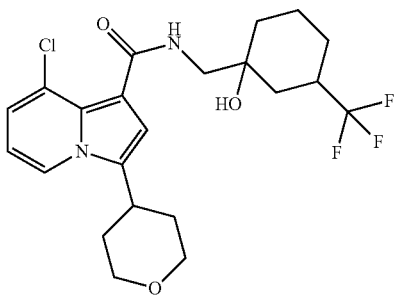 [SMILES: O=C(NCC1(O)CCCC(C(F)(F)F)C1)c1cc(C2CCOCC2)n2cccc(Cl)c12]

The title compound was synthesized (56 mg, 27%) according to the procedure described in example 34 using 8-Chloro-3-(tetrahydro-pyran-4-yl)-indolizine-1-carboxylic acid methyl ester (150.00 mg; 0.51 mmol; 1.00 eq.), 1-Aminomethyl-3-trifluoromethyl-cyclohexanol hydrochloride (178.98 mg; 0.77 mmol; 1.50 eq.) and 4-diazabicyclo[2.2.2]octane; trimethylalumane (392.70 mg; 1.53 mmol; 3.00 eq.) as the starting materials. The reaction was heated in microwave at 100° C. for 5 h.

$^1$H NMR (400 MHz, Chloroform-d) δ 7.81 (d, J=7.0 Hz, 1H), 6.93 (d, J=7.2 Hz, 1H), 6.88 (s, 1H), 6.61 (t, J=7.1 Hz, 1H), 6.45 (t, J=6.1 Hz, 1H), 4.19-4.04 (m, 2H), 3.72-3.48 (m, 5H), 3.16-2.99 (m, 1H), 2.39-2.22 (m, 1H), 2.12 (d, J=13.0 Hz, 1H), 2.06-1.77 (m, 8H), 1.59-1.17 (m, 5H). m/z: 459.0[M+H]$^+$ Scheme 6

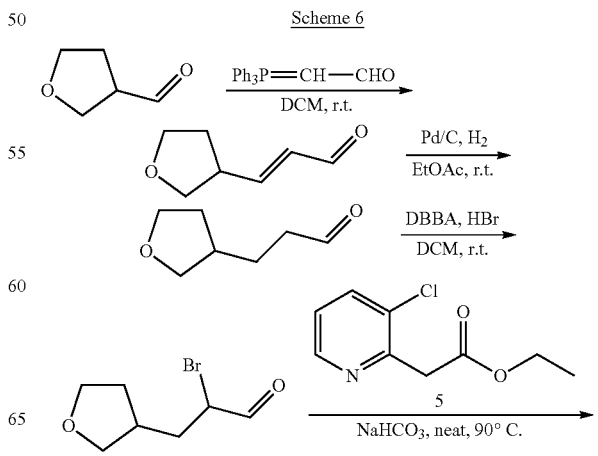

-continued

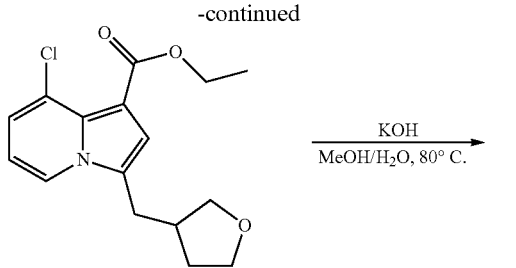

Intermediate 8

8-chloro-3-((tetrahydrofuran-2-yl)methyl)indolizine-1-carboxylic acid

Step 1. (E)-3-(Tetrahydrofuran-3-yl)acrylaldehyde

A mixture of tetrahydrofuran-3-carbaldehyde (14.5 g, 145 mmol) and (triphenylphosphoranylidene)acetaldehyde (49 g, 159.5 mmol) in DCM (300 mL) was stirred at room temperature overnight, and then quenched with water. The separated organic layer was washed with brine, dried over MgSO$_4$, filtered and concentrated in vacuo. The residue was purified by column chromatography on silica gel (eluting with Petroleum ether/EtOAc, 20:1-10:1) to afford (E)-3-(tetrahydrofuran-3-yl)acrylaldehyde (10.0 g, 56%) as a yellow oil.

Step 2. 3-(Tetrahydrofuran-3-yl)propanal

A mixture of (E)-3-(tetrahydrofuran-3-yl)acrylaldehyde (6 g, 47.6 mmol) and 10% Pd/C (0.600 g) in EtOAc (250 mL) was stirred under a hydrogen atmosphere at room temperature for 2.5 h, and then filtered through a Celite pad. The filtrate was concentrated and the resulting residue was purified by column chromatography on silica gel (Petroleum ether:EtOAc=5:1) to afford 3-(tetrahydrofuran-3-yl)propanal (3.5 g, 58%) as a colorless oil.

Step 3. 2-Bromo-3-(tetrahydrofuran-3-yl)propanal

A mixture of 3-(tetrahydrofuran-3-yl)propanal (0.770 g, 6.0 mmol), and 5,5-Dibromobarbituric acid (DBBA) (1.03 g, 3.6 mmol) in DCM (15 mL) was treated with HBr (40%, 0.2 mL). The resulting reaction mixture was stirred at room temperature for 2 h, and then filtered through a Celite pad. The filtrate was washed with water (20 mL×3), dried and concentrated to give 2-bromo-3-(tetrahydrofuran-3-yl)propanal (570 mg, 46%) as a yellow oil, which was used directly in the next step without further purification.

Step 4. Ethyl 8-chloro-3-((tetrahydrofuran-2-yl)methyl)indolizine-1-carboxylate

A mixture of 2-bromo-3-(tetrahydrofuran-3-yl)propanal (0.550 g, 2.6 mmol), ethyl 2-(3-chloropyridin-2-yl)acetate (0.530 g, 2.6 mmol) and NaHCO$_3$ (1.1 g, 13.0 mmol) was stirred at 90° C. under nitrogen overnight. The mixture was separated by column chromatography on silica gel (Petroleum ether:EtOAc=10:1-5:1) to afford ethyl 8-chloro-3-((tetrahydrofuran-2-yl)methyl)indolizine-1-carboxylate (0.400 g, 53%) as a green oil.

Step 5. 8-chloro-3-((tetrahydrofuran-2-yl)methyl)indolizine-1-carboxylic acid

A solution of ethyl 8-chloro-3-((tetrahydrofuran-2-yl)methyl)indolizine-1-carboxylate (0.400 g, 1.3 mmol) and KOH (0.365 g, 6.5 mmol) in MeOH/H2O (10 mL/10 mL) was stirred at 80° C. for 7 h, and then MeOH was removed. The aqueous solution was adjusted to pH 6 with 10% aqueous KHSO$_4$ and extracted with EtOAc. The organic layer was dried, and concentrated to give 8-chloro-3-((tetrahydrofuran-2-yl)methyl)indolizine-1-carboxylic acid (0.300 g, 82%) as a white solid.

Example 72

8-chloro-N-((4,4-difluorocyclo-hexyl)methyl)-3-((tetrahydrofuran-3-yl)methyl)indolizine-1-carboxamide (30)

To a solution of 8-chloro-3-((tetrahydrofuran-2-yl)methyl)indolizine-1-carboxylic acid (0.120 g, 0.43 mmol) in DMF (2 mL) were added (4,4-difluorocyclohexyl)methanamine hydrochloride (0.789 g, 0.43 mmol), HATU (0.245 g, 0.64 mmol) and TEA (0.217 mg, 2.15 mmol). After being stirred at room temperature for 2 h, the reaction was quenched with water and extracted with EtOAc (30 mL×3). The combined extracts were dried over Na$_2$SO$_4$, filtered and concentrated in vacuo. The residue was purified by Prep-HPLC to 8-chloro-N-((4, 4-difluorocyclo-hexyl)methyl)-3-((tetrahydrofuran-2-yl) methyl)indolizine-1-carboxamide (0.021 g, 11.9%) as a white solid.

$^1$H NMR (500 MHz, DMSO-d$_6$): δ 8.18 (d, J=7.0 Hz, 1 H), 8.08-8.06 (m, 1 H), 6.96 (d, J=6.5 Hz, 1H), 6.79 (s, 1 H), 6.68 (t, J=7.0 Hz, 1 H), 3.82-3.78 (m, 2 H), 3.69-3.65 (m, 1

H), 3.41-3.38 (m, 1 H), 3.15-3.12 (m, 2 H), 2.91-2.90 (m, 2 H), 2.64-2.61 (m, 1 H), 2.06-2.01 (m, 3 H), 1.83-1.58 (m, 6 H), 1.27-1.22 (m, 2 H) ppm; m/z: 411.1 [M+H]$^+$

Example 73

8-chloro-N-((4,4-difluoro-1-hydroxycyclo-hexyl)methyl)-3-((tetrahydrofuran-3-yl)methyl)indolizine-1-carboxamide (47)

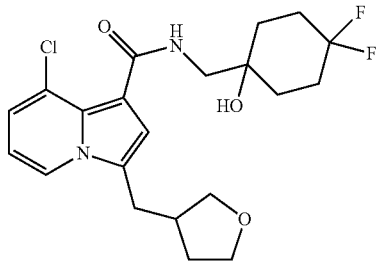 [SMILES: O=C(NCC1(O)CCC(F)(F)CC1)c1cc(CC2CCOC2)n2cccc(Cl)c12]

The title compound was synthesized (0.024 g, 12.8%) according to the procedure described in example 62 using 8-chloro-3-((tetrahydrofuran-2-yl)methyl)indolizine-1-carboxylic acid (0.120 g, 0.43 mmol), 1-(aminomethyl)-4,4-difluorocyclohexanol hydrochloride (0.087 g, 0.43 mmol), HATU (0.245 g, 0.64 mmol) and TEA (0.217 g, 2.15 mmol) as the starting materials.

$^1$H NMR (500 MHz, DMSO-d$_6$): δ 8.19 (d, J=7.0 Hz, 1 H), 7.95 (t, J=6.0 Hz, 1 H), 6.99 (d, J=7.0 Hz, 1 H), 6.84 (s, 1H), 6.70 (t, J=7.0 Hz, 1 H), 4.73 (s, 1 H), 3.83-3.79 (m, 2 H), 3.69-3.65 (m, 1 H), 3.42-3.39 (m, 1 H), 3.29 (d, J=6.0 Hz, 2 H), 2.92-2.90 (m, 2 H), 2.65-2.62 (m, 1 H), 2.07-1.97 (m, 3 H), 1.89-1.85 (m, 2 H), 1.64-1.58 (m, 5 H) ppm; [M+H]$^+$427.1; LC-MS Purity (254 nm): 100%; t$_R$=3.85 min; HPLC Purity (254 nm): 100%; t$_R$=3.82 min.

Example 74

(S)-8-chloro-N-((4,4-difluoro-1-hydroxycyclohexyl)methyl)-3-((tetrahydrofuran-3-yl)methyl)indolizine-1-carboxamide (52)

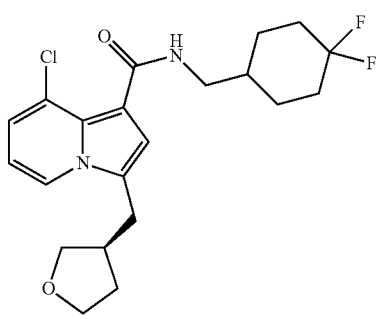 [SMILES: O=C(NCC1CCC(F)(F)CC1)c1cc(C[C@H]2CCOC2)n2cccc(Cl)c12]

A racemic mixture of 8-chloro-N-((4,4-difluorocyclohexyl)methyl)-3-((tetrahydrofuran-2-yl)methyl)indolizine-1-carboxamide was separated from chiral HPLC to provide (S)-8-chloro-N-((4,4-difluorocyclohexyl)methyl)-3-((tetrahydrofuran-3-yl)methyl) indolizine-1-carboxamide.

Chiral-HPLC conditions: Co-Solvent: 25% MeOH, Column: OD-H (4.6*250 mm, 5 um)

CO$_2$ Flow Rate: 2.25 mL/min, Co-Solvent Flow Rate: 0.75 mL/min, Total Flow: 3 mL/min Runtime: 9 min $^1$H NMR (500 MHz, DMSO-d$_6$) δ 8.19 (d, J=7.0 Hz, 1 H), 7.95 (t, J=6.0 Hz, 1 H), 6.99 (d, J=7.0 Hz, 1 H), 6.84 (s, 1 H), 6.70 (t, J=7.0 Hz, 1 H), 4.73 (s, 1 H), 3.83-3.79 (m, 2 H), 3.69-3.65 (m, 1 H), 3.42-3.39 (m, 1 H), 3.29 (d, J=6.0 Hz, 2 H), 2.92-2.90 (m, 2 H), 2.65-2.62 (m, 1 H), 2.07-1.97 (m, 3 H), 1.89-1.85 (m, 2 H), 1.64-1.58 (m, 5 H) ppm; m/z: 427.1[M+H]$^+$

Example 75

(R)-8-chloro-N-((4,4-difluoro-1-hydroxycyclohexyl)methyl)-3-((tetrahydrofuran-3-yl)methyl)indolizine-1-carboxamide (50)

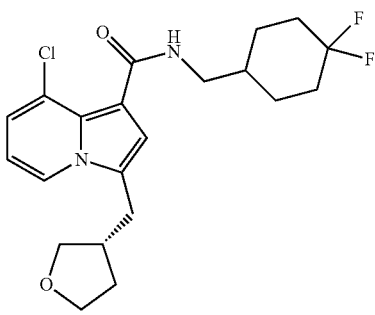 [SMILES: O=C(NCC1CCC(F)(F)CC1)c1cc(C[C@@H]2CCOC2)n2cccc(Cl)c12]

A racemic mixture of 8-chloro-N-((4, 4-difluorocyclohexyl)methyl)-3-((tetrahydrofuran-2-yl)methyl)indolizine-1-carboxamide was separated from chiral HPLC to get (R)-8-chloro-N-((4,4-difluorocyclohexyl)methyl)-3-((tetrahydrofuran-3-yl)methyl)indolizine-1-carboxamide.

$^1$H NMR (500 MHz, DMSO-d$_6$) δ 8.19 (d, J=7.0 Hz, 1 H), 7.95 (t, J=6.0 Hz, 1 H), 6.99 (d, J=7.0 Hz, 1 H), 6.84 (s, 1H), 6.70 (t, J=7.0 Hz, 1 H), 4.73 (s, 1 H), 3.83-3.79 (m, 2 H), 3.69-3.65 (m, 1 H), 3.42-3.39 (m, 1 H), 3.29 (d, J=6.0 Hz, 2 H), 2.92-2.90 (m, 2 H), 2.65-2.62 (m, 1 H), 2.07-1.97 (m, 3 H), 1.89-1.85 (m, 2 H), 1.64-1.58 (m, 5 H) ppm; m/z: 427.1 [M+H]$^+$

Example 76

IL-1β Release Assay: The activation of P2X7 by ATP leads to a fast transient activation of cells resulting in influx of Ca$^{2+}$ followed by conversion of pro-IL-1β to active IL-1β. The functional activity of P2X7 compounds was measured by the release of mature IL-1β in the culture medium of THP-1 cells, detected by sandwich ELISA. Cells were maintained in complete growth medium (RPMI 1640+10% HI-FCS+2 mM L-glutamine+1×PS). Every 3 days, the medium was renewed by diluting the cells 1/3 to 1/4 as cell density did not exceed 0.5 million cells per ml (seeding cell density @1×10$^5$/ml). THP-1 cells were harvested from the flask in 50 ml by centrifugation for 3 min at 100 g. The cells were resuspended to 2×10$^5$ cells/ml in medium supplemented with 0.5 μM PMA and incubated. The cells were washed and resuspended to 1.5×10$^5$ cells/ml in medium complemented with 10 ng/ml LPS, and the cells were primed for 4 h at 37° C., 5% CO$_2$. After addition of 20 μL of prediluted test compounds, blank, standard and control reagents, cells were incubated for a further 20 min at 37° C. and stimulated with 0.8 mM BzATP for 30 minutes. The cells were centrifuged, supernatant was collected and the presence of mature IL-1β was detected using Dual human IL-1b kit following manufacturer's instruction. The tetrahydrobenzodiazepine analogs effectively modulated the activity of P2X7 in the cells as measured by the levels of pro-inflammatory cytokine IL-13, which is released by the activation of P2X7 receptor.

Pore Permeation Assay

Agonist-induced pore formation was determined by measuring cellular uptake of YO PRO fluorescence dye in HEK293 transfected with human P2X7 receptor. A HEK293 cell over expressing human P2X7 was harvested using HQTase reagent to detach the cells from T75 cm flask. The harvested cells are centrifuged @1200 rpm for 5 min at room temperature. The viability of cells was determined by Trypan blue dye and the cells are plated @10,000 cell/well in 50 ul volume in a 384 W BD Poly lysine coated plate and incubated overnight at 37 C. After overnight incubation, the culture medium was replaced with 35 ul/well assay buffer (5 mM KCl, 0.1 mM CaCl2, 5 mM Glucose, 10 mM HEPES buffer pH7.4 containing 125 mM NaCl. The serial dilution of compounds was performed using Bravo liquid handling instrument and the compounds were added using Bravo to the cell assay plate starting at 2.5 uM with three dilutions for 10 points. The positive control inhibitor compound was added to column 23. The plate was shaken slowly on a plate shaker for 10 seconds. The cells were incubated with the compound for 20 minutes at room temperature. After the incubation period, YO PRO dye (1 uM) along with BzATP (10 uM) were added to cells at 10 ul/well. The plate was centrifuged at 1000 rpm for 5 seconds and incubated at room temperature for 30 minutes. The uptake of YO PRO dye into the cells was measured using Envision Fluorescence plate reader instrument (Perkin Elmer).

The data is interpreted according to the following:

| | |
|---|---|
| E | >1 μM; |
| D | 500-999 nM; |
| C | 101-500 nM; |
| B | 10-100 nM; |
| A | <10 nM. |

| Compound number | hP2X7 IC50 | hTHP-1/IL-ib IC50 |
|---|---|---|
| 1 | B | C |
| 2 | A | B |
| 3 | C | |
| 4 | E | |
| 5 | B | C |
| 6 | B | B |
| 7 | C | |
| 8 | B | C |
| 9 | C | C |
| 10 | B | B |
| 11 | A | B |
| 12 | B | C |
| 13 | B | B |
| 14 | B | B |
| 15 | C | C |
| 16 | B | C |
| 17 | A | B |
| 18 | B | B |
| 19 | C | |
| 20 | B | |
| 21 | C | C |
| 22 | B | B |
| 23 | B | B |
| 24 | A | A |
| 25 | C | |
| 26 | C | |
| 27 | B | |
| 28 | D | |
| 29 | C | C |
| 30 | B | C |
| 31 | B | B |
| 32 | A | B |
| 33 | B | |
| 34 | B | |
| 35 | B | B |
| 36 | B | B |
| 37 | B | B |
| 38 | B | |
| 39 | B | C |
| 40 | B | B |
| 41 | C | B |
| 42 | C | |
| 43 | B | C |
| 44 | C | |
| 45 | B | C |
| 46 | C | |
| 47 | B | B |
| 48 | B | B |
| 49 | C | |
| 50 | B | C |
| 51 | B | C |
| 52 | B | B |
| 53 | B | B |
| 54 | A | B |
| 55 | C | |
| 56 | B | |
| 57 | C | C |
| 58 | C | |
| 59 | | E |
| 60 | C | B |
| 61 | B | B |
| 62 | A | B |
| 63 | A | A |
| 64 | B | C |
| 65 | B | B |
| 66 | B | C |
| 67 | B | B |
| 68 | B | |
| 69 | C | C |
| 70 | B | B |
| 71 | B | B |
| 72 | B | B |
| 73 | B | B |
| 74 | E | |
| 75 | B | |

Example 77

Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I,

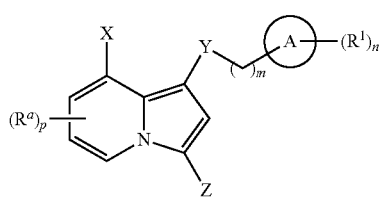

I or a pharmaceutically acceptable salt thereof, wherein:
X is -halogen, -haloalkyl, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$; or X is a C$_{1-6}$ aliphatic, C$_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
Y is O, S, SO$_2$, SO, C(O), CO$_2$, C(O)N(R), NRC(O), NRC(O)N(R), NRSO$_2$, or N(R);
Ring A is C$_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; or a 6-18 membered bicyclic, fused bicyclic, spiro bicyclic, or polycyclic ring having 0-4 heteroatoms independently selected from nitrogen, oxygen, or sulfur, each of which is optionally substituted;
each R$^1$ is independently —R, halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$; or
two R$^1$ groups, together with the atom or atoms to which each is attached, may form a fused or spiro ring selected from C$_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
Z is —R, halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$,
each R$^a$ is independently —R, halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
each R is independently hydrogen, C$_{1-6}$ aliphatic, C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
m is 1 or 2;
n is 0, 1, 2, or 3; and
p is 0, 1, or 2.

2. The compound of claim 1, wherein X is -halogen, -haloalkyl, or an optionally substituted C$_{1-6}$ aliphatic.

3. The compound of claim 1, wherein Y is C(O), CO$_2$, C(O)NH, NHC(O), or NHSO$_2$.

4. The compound of claim 3, wherein Y is

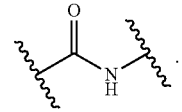 [SMILES: *NC(*)=O]

5. The compound of claim 1, wherein Ring A is phenyl, cyclopropyl, cyclobutyl, cyclopentyl, cyclohexyl, or cycloheptyl.

6. The compound of claim 5, wherein Ring A is

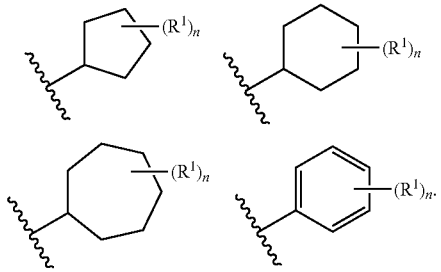

7. The compound of claim 6, wherein each R¹ is independently methyl, ethyl, n-propyl, i-propyl, n-butyl, s-butyl, t-butyl, straight chain or branched pentyl, straight chain or branched hexyl, OH, F, Cl, Br, I, or CF₃; or two R¹ groups, together with the atom or atoms to which each is attached, may form a fused or spiro ring selected from cyclopropyl, cyclobutyl, cyclopentyl, cyclohexyl, and cycloheptyl.

8. The compound of claim 5, wherein Ring A is

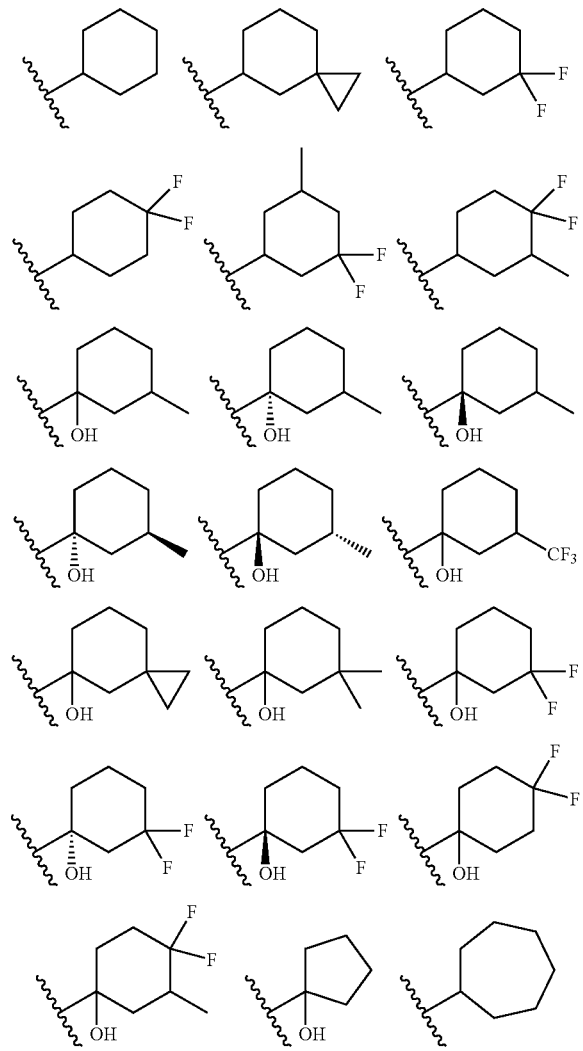

-continued

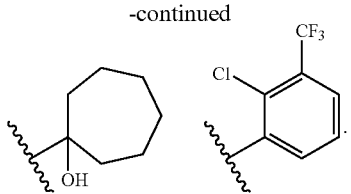

9. The compound of claim 1, wherein Z is H or I.

10. The compound of claim 1, wherein Z is $C_{1-6}$ aliphatic, a 3-8 membered saturated or partially unsaturated carbocyclic ring, or a 3-7 membered heterocylic ring having 1-4 heteroatoms independently selected from nitrogen, oxygen, or sulfur; each of which is optionally substituted.

11. The compound of claim 10, wherein Z is

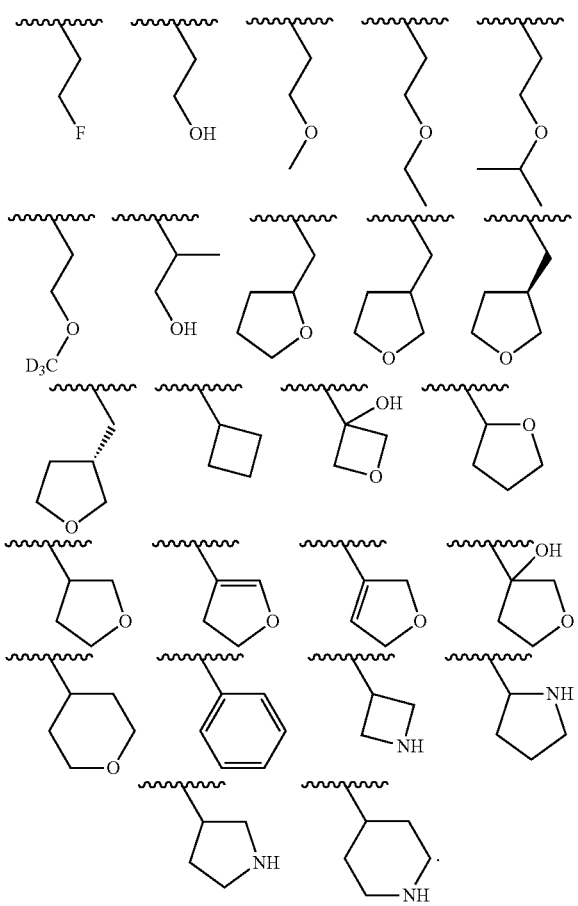

12. The compound of claim 1, of formula III:

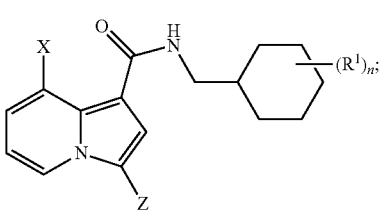

or a pharmaceutically acceptable salt thereof.

13. The compound of claim 1, of formula V:
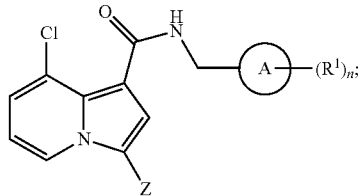
or a pharmaceutically acceptable salt thereof.
14. The compound of claim 1, selected from
1
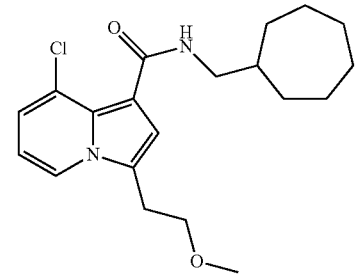
2
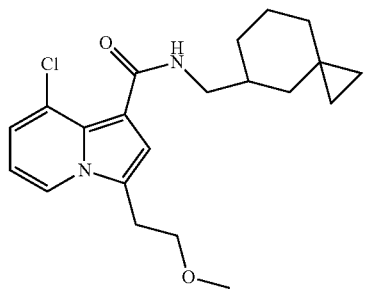
3
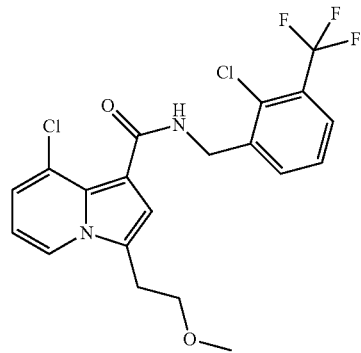
-continued
4
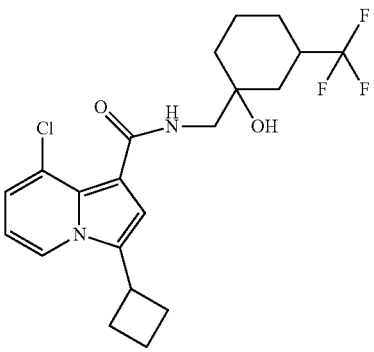
5
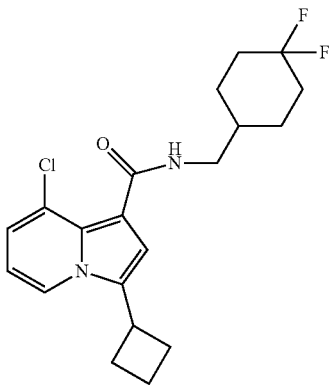
6
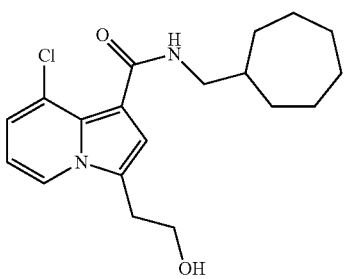
7
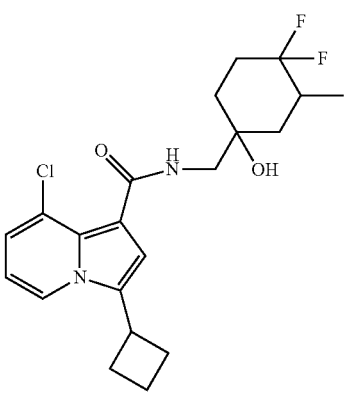

123
-continued
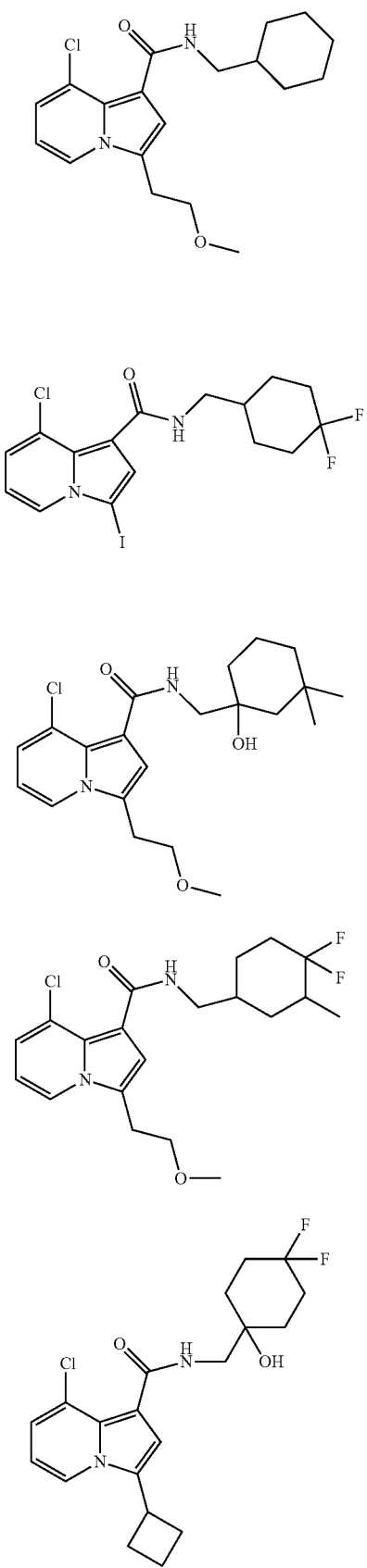
124
-continued
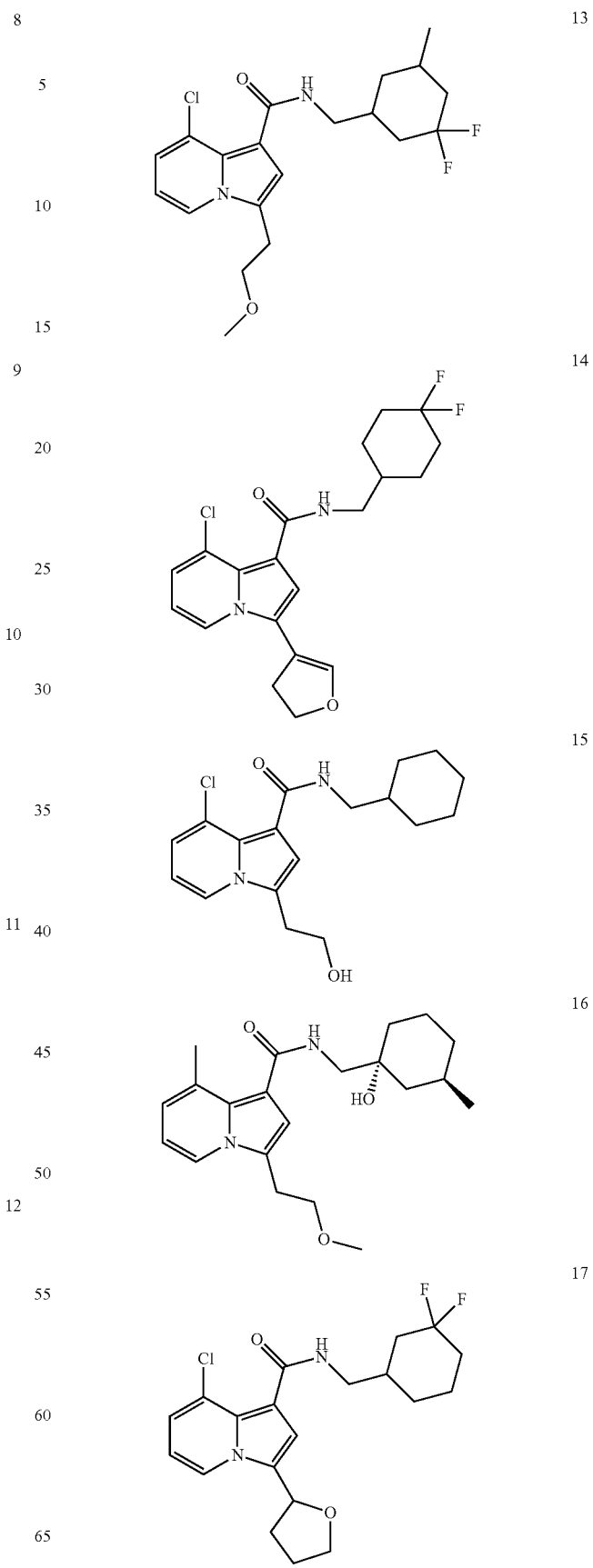

-continued
18
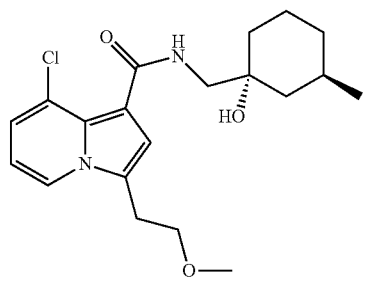
19
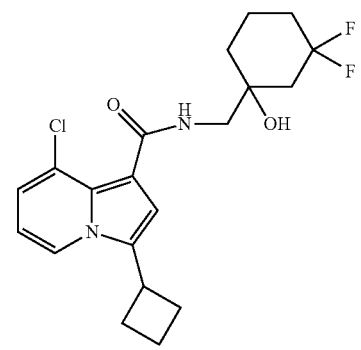
20
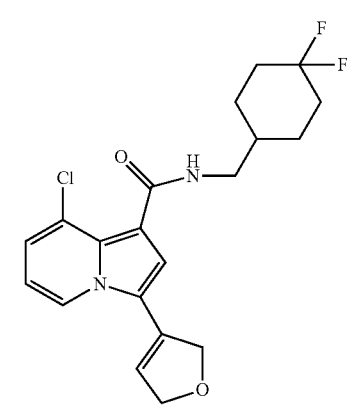
21
-continued
22
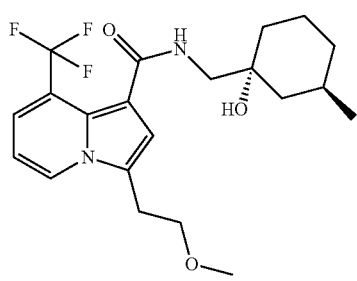
23
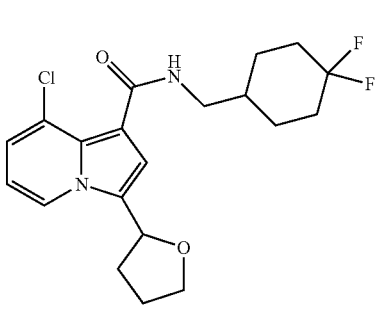
24
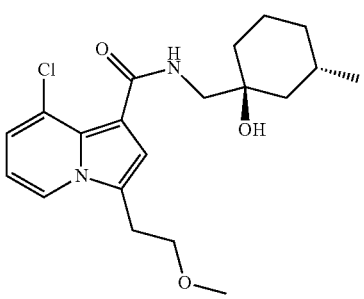
25
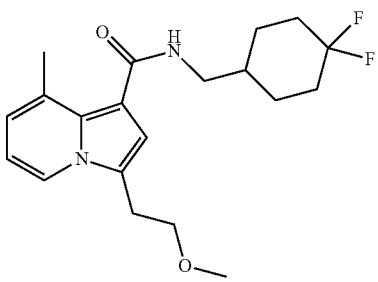
26
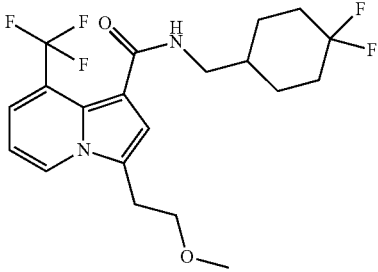

27
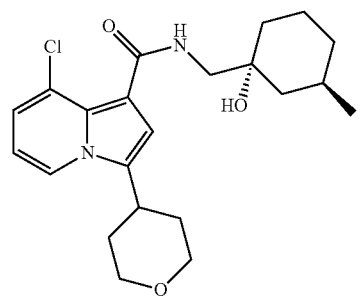
28
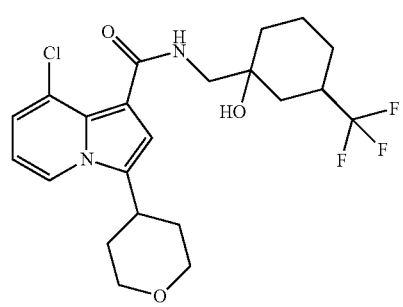
29
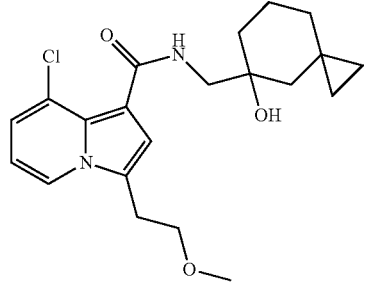
30
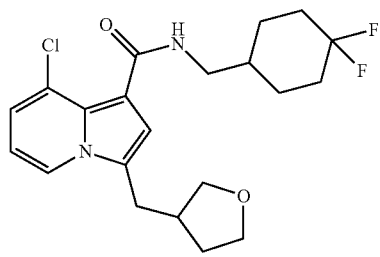
31
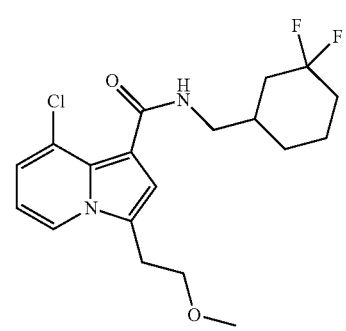
32
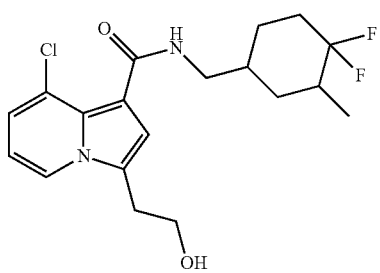
33
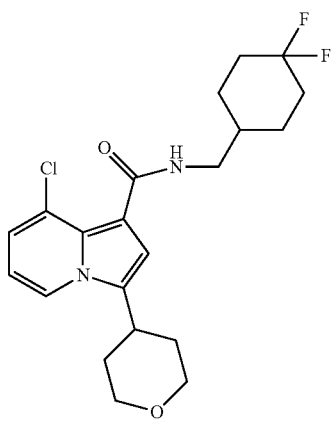
34
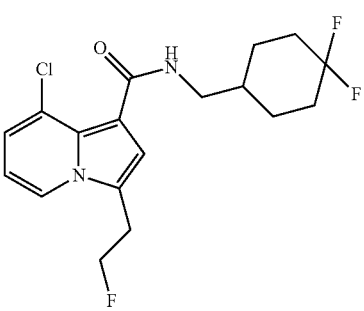
35
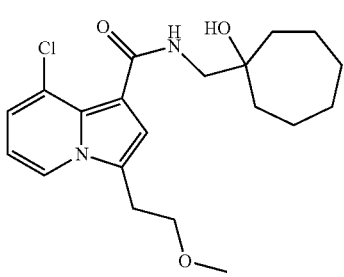
36
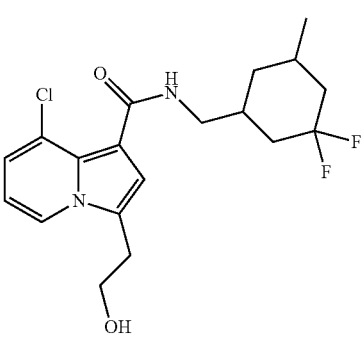

| 37 | 42 |
|---|---|
| 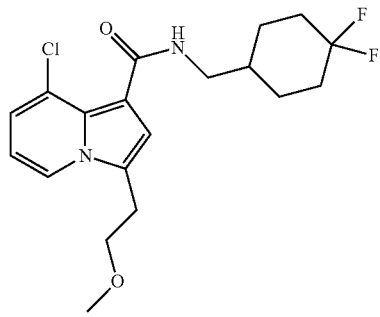 | 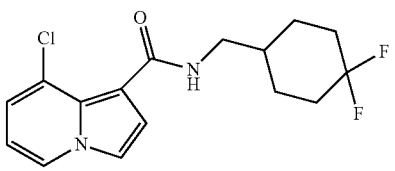 |
| 38 | 43 |
| 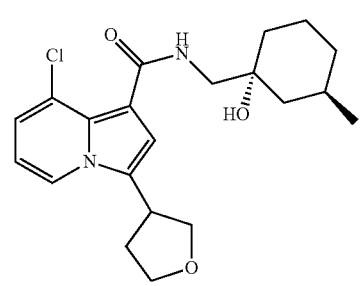 | 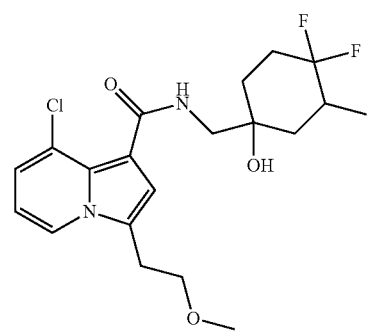 |
| 39 | 44 |
| 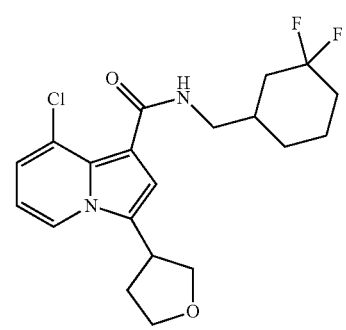 | 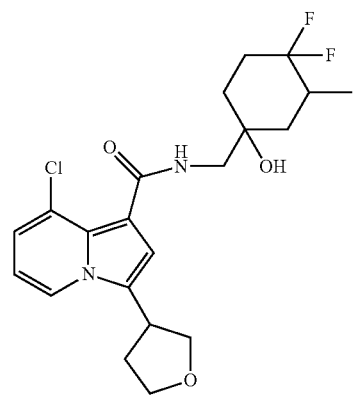 |
| 40 | 45 |
| 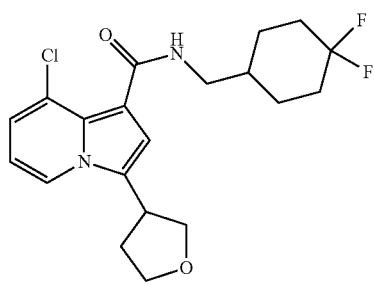 | 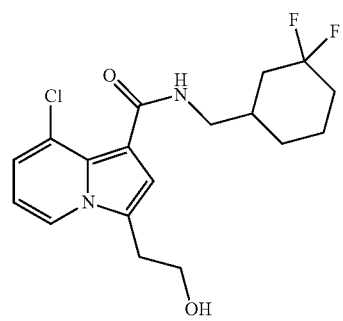 |
| 41 | 46 |
| 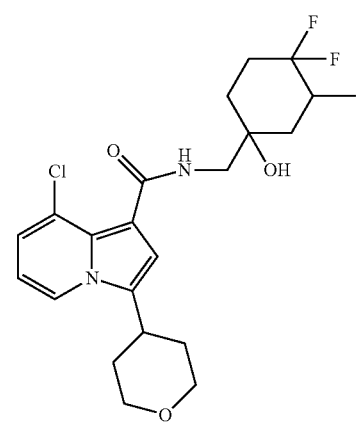 | 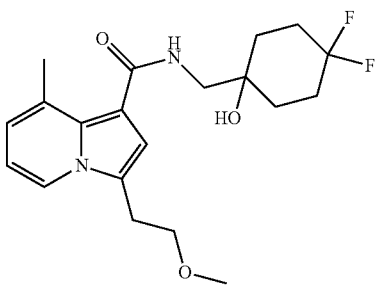 |

47
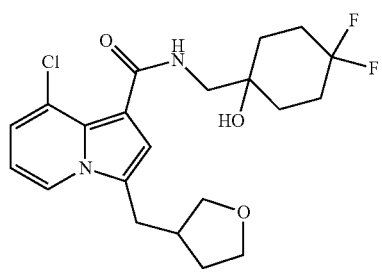
48
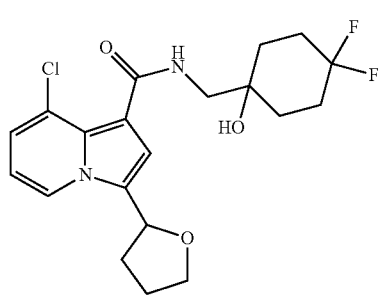
49
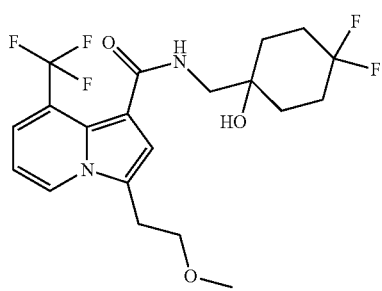
50
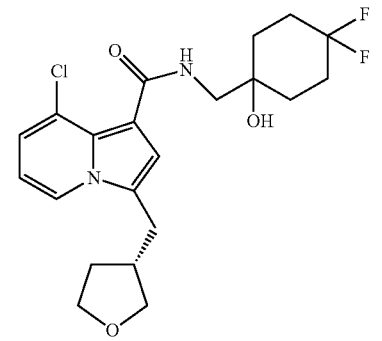
51
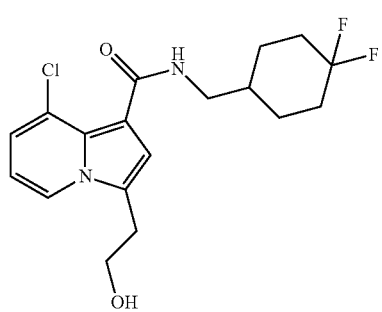
52
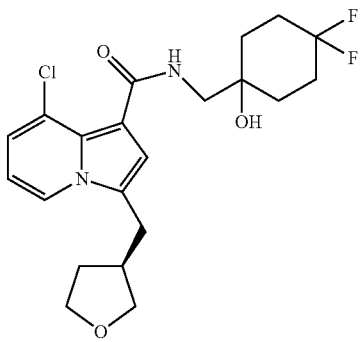
53
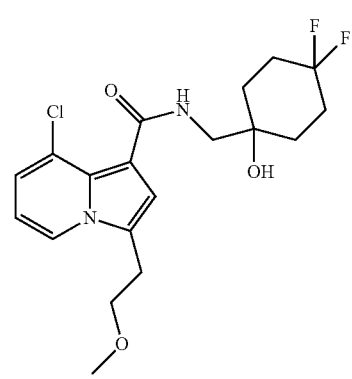
54
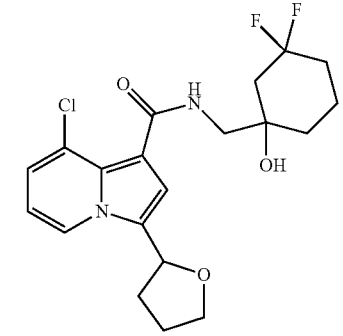
55
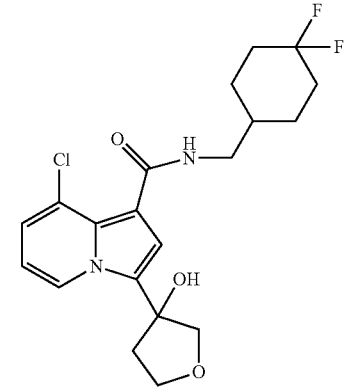

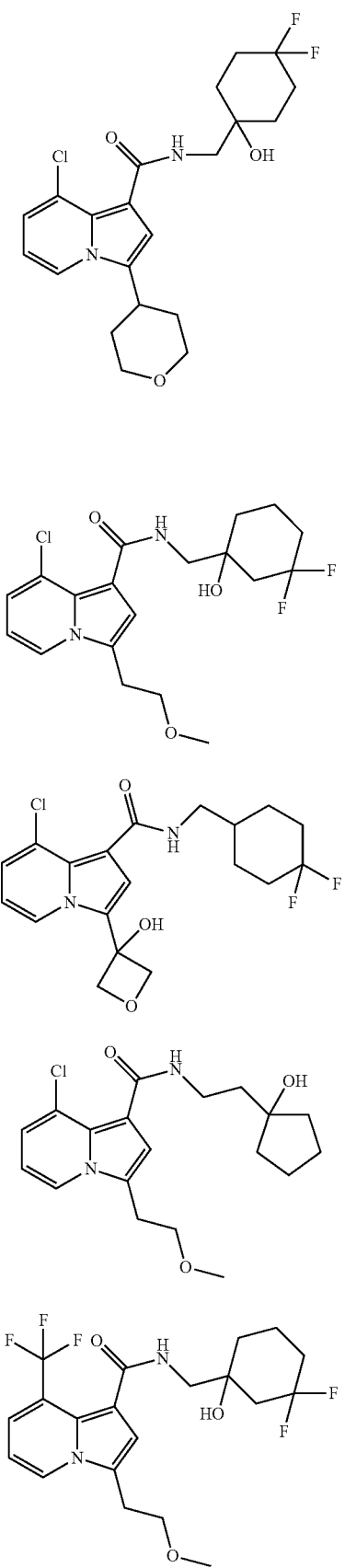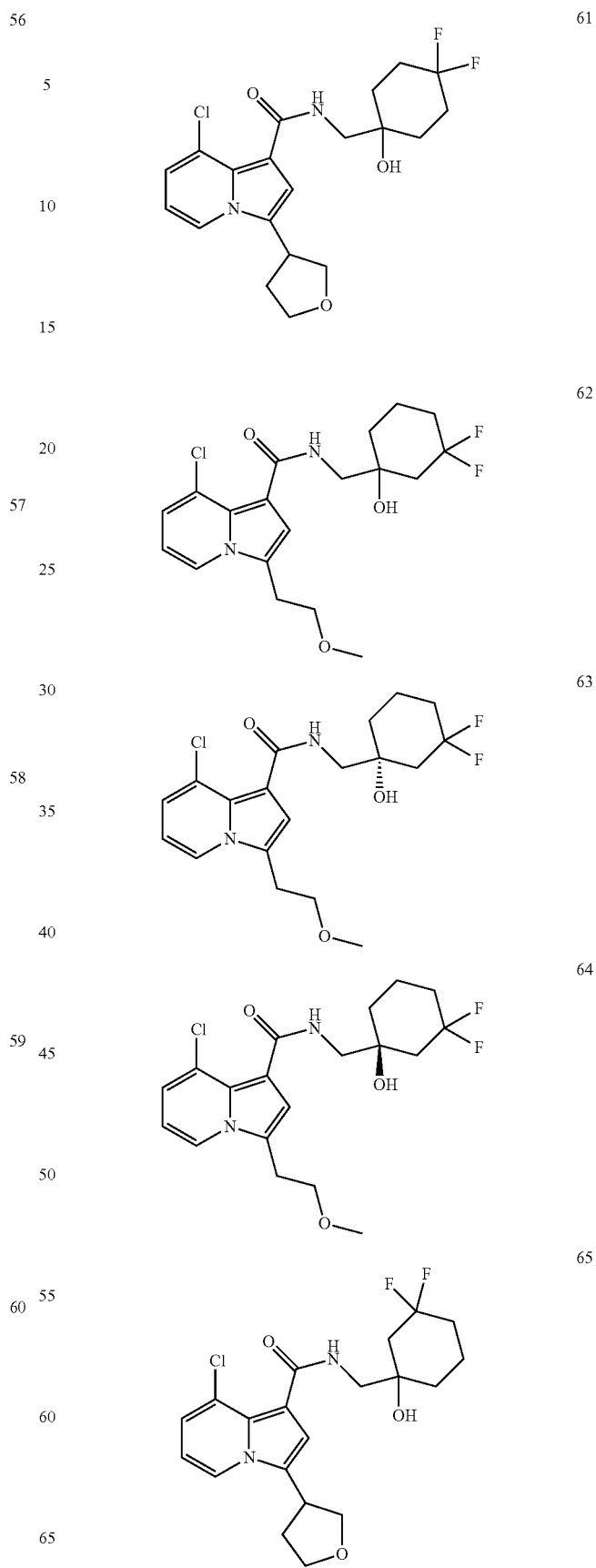

66
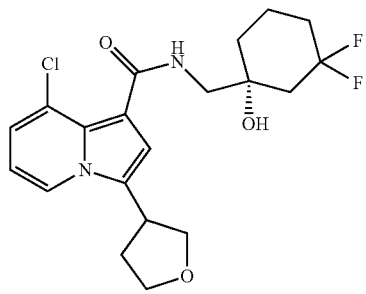
67
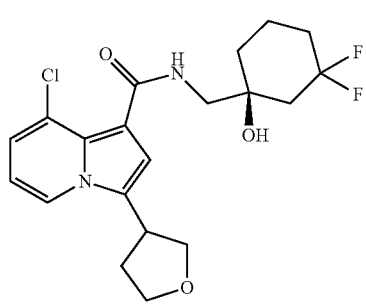
68
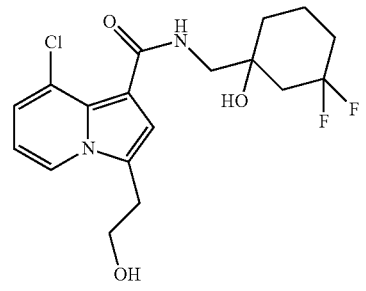
69
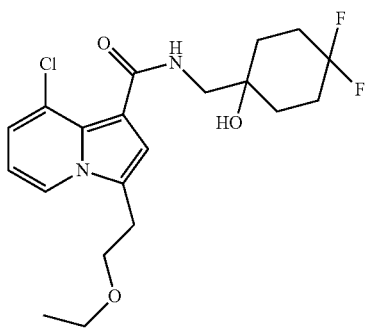
70
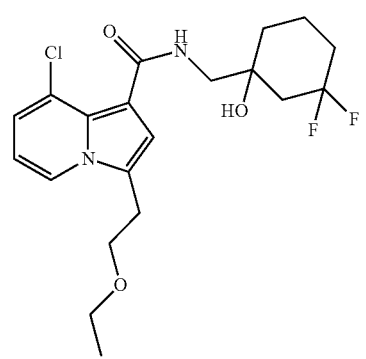
71
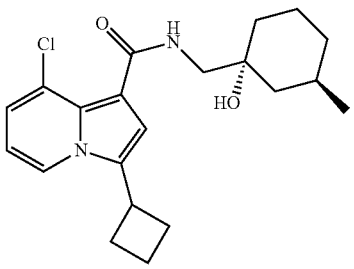
72
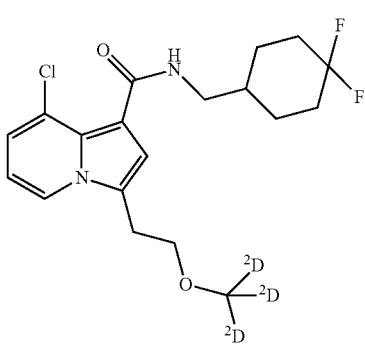
73
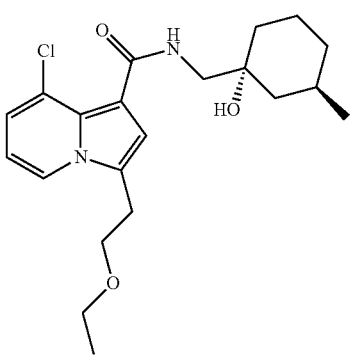
74
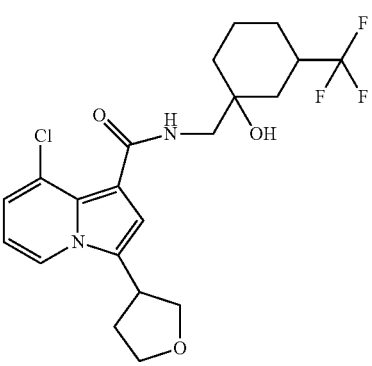
75
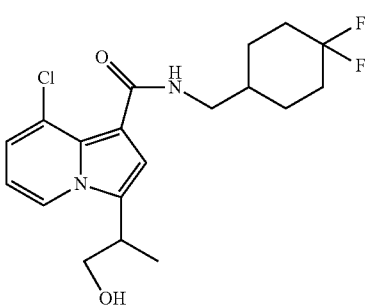

76
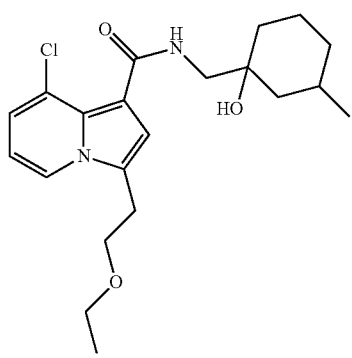
77
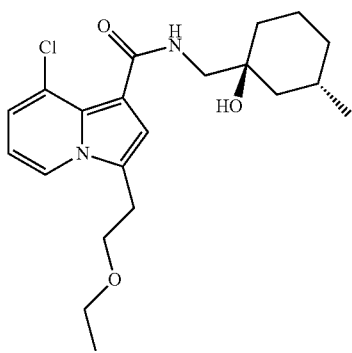
78
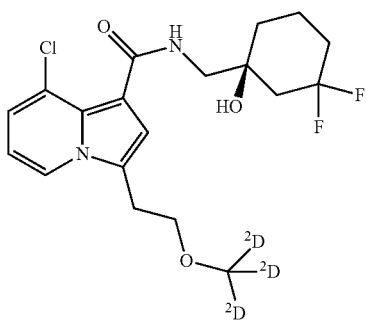
79
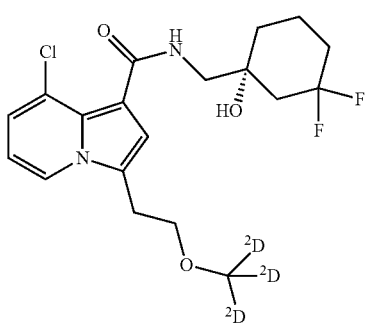
80
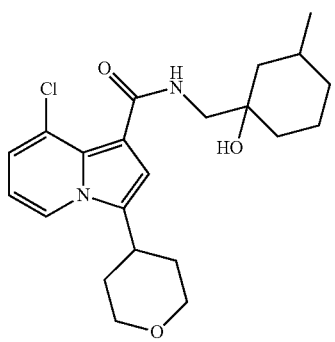
81
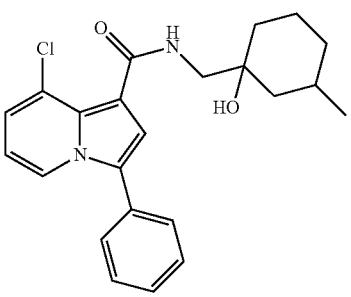
82
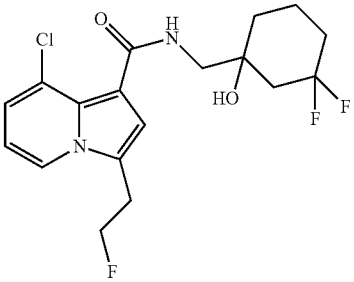
83
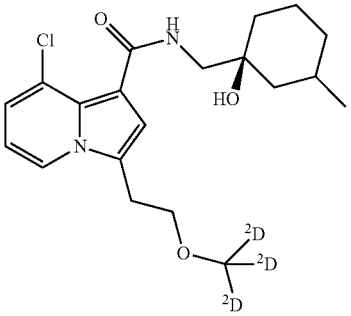
84
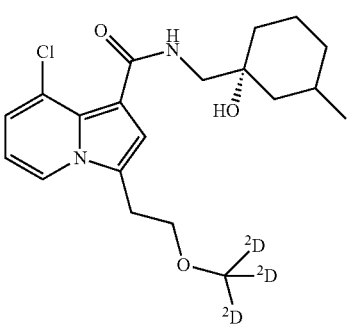

-continued

85 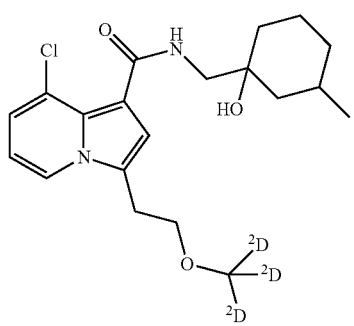

86 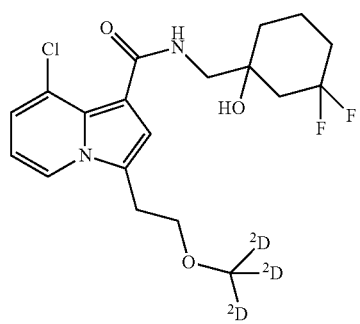

87 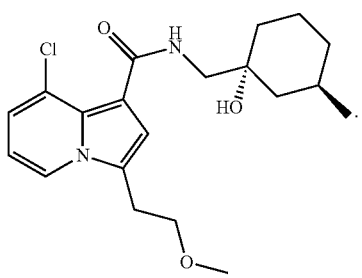

15. A pharmaceutical composition comprising a compound of claim 1, and a pharmaceutically acceptable adjuvant, carrier, or vehicle.

16. A process for manufacturing a compound of formula I, comprising the steps of:

reacting a compound of formula A:

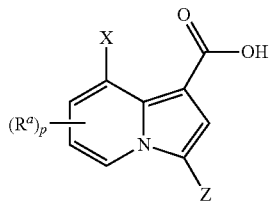

A wherein X, Z, $R^a$, and p are as defined in claim 1;

with a compound of formula B:

B wherein Ring A, $R^1$, m, and n are as defined in claim 1;

to yield a compound of formula I:

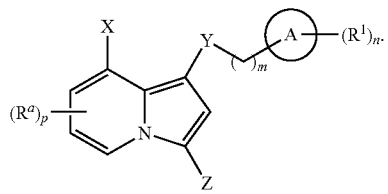

I

* * * * *